(12) United States Patent
Chui et al.

(10) Patent No.: US 6,986,992 B2
(45) Date of Patent: Jan. 17, 2006

(54) P450 SINGLE NUCLEOTIDE POLYMORPHISM BIOCHIP ANALYSIS

(75) Inventors: Buena Chui, Chandler, AZ (US); Robert Elghanian, Skokie, IL (US); Vineet Gupta, Reading, MA (US); Krishnamurthy Jayaraman, Hoffman Estates, IL (US); Gretchen Kiser, Mesa, AZ (US); Changming Li, Schaumburg, AZ (US); Chang-Gong Liu, Cherry Hill, NJ (US); Kenneth R. Luehrsen, Half Moon Bay, CA (US); Abhijit Mazumder, Buffalo Grove, IL (US); Ramesh Ramakrishnan, Vernon Hills, IL (US); Arkadiy Silbergleyt, Chandler, AZ (US); Todd Tuggle, Oceanside, CA (US); Carl Yamashiro, Chandler, AZ (US); Handy Yowanto, Walnut, CA (US); Ekaterina Pestova, Downers Grove, IL (US); David R. Fermin, Minneapolis, MN (US); David G. Wang, Deerfield, IL (US); Zhijie John Gu, San Diego, CA (US)

(73) Assignee: Amersham Biosciences AB, Uppsala (SE)

( * ) Notice: Subject to any disclaimer, the term of this patent is extended or adjusted under 35 U.S.C. 154(b) by 176 days.

(21) Appl. No.: 10/114,908

(22) Filed: Apr. 1, 2002

(65) Prior Publication Data

US 2004/0229222 A1 Nov. 18, 2004

Related U.S. Application Data

(60) Provisional application No. 60/280,583, filed on Mar. 30, 2001.

(51) Int. Cl.
*C12Q 1/68* (2006.01)

(52) U.S. Cl. .......................................... 435/6; 435/91.2
(58) Field of Classification Search .................... 435/6, 435/91.2
See application file for complete search history.

(56) References Cited

U.S. PATENT DOCUMENTS

| | | | |
|---|---|---|---|
| 4,656,127 A | 4/1987 | Mundy | |
| 4,778,756 A | 10/1988 | Yoshida et al. | |
| 4,851,331 A | 7/1989 | Vary et al. | |
| 5,137,806 A | 8/1992 | LeMaistre et al. | |
| 5,268,465 A | 12/1993 | Bredt et al. | |
| 5,498,539 A | 3/1996 | Harrison et al. | |
| 5,578,458 A | 11/1996 | Caskey et al. | |
| 5,582,970 A | 12/1996 | Wallace | |
| 5,595,890 A | 1/1997 | Newton et al. | |
| 5,639,611 A | 6/1997 | Wallace et al. | |
| 5,665,539 A | 9/1997 | Sano et al. | |
| 5,710,028 A | 1/1998 | Eyal et al. | |
| 5,824,476 A | 10/1998 | Wallace | |
| 5,846,710 A | 12/1998 | Bajaj | |
| 5,856,092 A | 1/1999 | Dale et al. | |
| 5,856,130 A | 1/1999 | Bandman et al. | |
| 5,888,819 A | 3/1999 | Goelet et al. | |
| 5,891,628 A | 4/1999 | Reeders et al. | |
| 5,912,120 A | 6/1999 | Goldstein et al. | |
| 5,912,340 A | 6/1999 | Kutyavin et al. | |
| 5,942,422 A | * 8/1999 | Rothstein ................... | 435/91.1 |
| 5,981,176 A | 11/1999 | Wallace | |
| 6,001,611 A | 12/1999 | Will | |
| 6,004,744 A | 12/1999 | Goelet et al. | |
| 6,013,431 A | 1/2000 | Söderlund et al. | |
| 6,015,675 A | 1/2000 | Caskey et al. | |
| 6,153,379 A | 11/2000 | Caskey et al. | |
| 6,183,958 B1 | 2/2001 | Stanton, Jr. | |
| 6,287,778 B1 | 9/2001 | Huang et al. | |
| 6,307,039 B1 | 10/2001 | Southern et al. | |
| 2003/0049657 A1 | * 3/2003 | Cherry ......................... | 435/6 |
| 2003/0104372 A1 | * 6/2003 | Ahmadian et al. ............. | 435/6 |

FOREIGN PATENT DOCUMENTS

| | | |
|---|---|---|
| EP | 0 371 437 A2 | 6/1990 |
| WO | WO 92/15712 | 9/1992 |
| WO | WO 97/12896 | 4/1997 |
| WO | WO 00/06779 | 2/2000 |
| WO | WO 01/54814 A2 | 8/2001 |
| WO | WO 0107665 | 2/2002 |

OTHER PUBLICATIONS

Dubiley et al. (Nucleic Acids Research, 1999, vol. 27, No. 18, e19).*
Ingelman–Sundberg et al. (TiPS, Aug. 1999, vol. 20, pp. 342–349).*
Stoilov et al. (Human Molecular Genetics, 1997, vol. 6, No. 4, pp. 641–647).*
Sitbon et al. (Thrombosis and Haemostasis, 77(4)701–3, 1997).*

(Continued)

*Primary Examiner*—Juliet C. Switzer
(74) *Attorney, Agent, or Firm*—Royal N. Ronning, Jr.; Yonggang Ji; Stephen G. Ryan

(57) ABSTRACT

This invention relates to methods and compositions for determining single nucleotide polymorphisms (SNPs) in P450 genes. In preferred embodiments, self extension of interrogation probes is prevented by using novel non self-extension probes and/or methods, thereby improving the specificity and efficiency of P450 SNP detection in target samples with minimal false positive results. The invention thus describes a variety of methods to decrease self-extension of interrogation probes. In addition, this invention provides a unique collection of P450 SNP probes on one assay, primer sequences for specific amplification of each of the seven P450 genes and amplicon control probes to evaluate whether the intended p450 gene targets were amplified successfully. The invention also describes a variety of array platforms for performing the assays of the invention; for example: CodeLink™, eSensor™, multiplex arrays with cartridges etc., all described herein.

2 Claims, 44 Drawing Sheets

OTHER PUBLICATIONS

Panchuk–Voloshina et al. (The Journal of Histochemistry & Cytochemistry, vol. 47(9):1179–1188).*

Pirrung et al. (Bioorganic & Medicinal Chemistry Letters 11(2001) 2437–2440).*

Marez, D., et al., "Polymorphism of the Cytochrome P450 CYP2D6 Gene in a European Population: Characterization of 48 Mutations." Pharmacogenics (1997) 7: 193–202.

Kimura, S., et al., "The Human Desbrisoquine 4–Hydroxylase (CYP2D6) Locus: Sequence and Identification of the Polymorphic CYP2." Am. J. Hum. Genet. (1989) 45:889–904.

Kimura, S., et al., "cDNA and Amino Acid Sequences of Two Members of the Human p450 IIC Gene Subfamily." Nucleic Acid Res. (1987) 15(23): 10053–4.

Heim, M., et al., "Evolution of a Highly Polymorphic Human Cytochrome P450 Gene Cluster: CYP2D6." Genomics (1992) 14:49–58.

Marez–Allorge., D., et al. "A rare G2061 insertion affecting the open reading frame of CYP2D6 and responsible for the poor metabolizer phenotype." Pharmacogenetics (1999) 9:3): 393–396.

Yokoto, H., et al., "Evidence for a new variant CYP2D6 in a Japanese population associated with lower in vivo rates." Pharmacogenetics (1993) 3(5): 256–263.

Sachse, C., et al., "A rare insertion of T226 in exon 1 of CYP2D6 causes a frameshift and is associated with the poor metabolizer." Pharmacogenetics, (1996) 6(3):269–272.

Sachse, C., et al., "Functional Significance of a C—A Polymorphism in Intron 1 of the Cytochrome P450 CYP 1A2 Gene Tested with Caffeine." Br. J. Clin. Pharmacol. (1999) 47: 445–449.

Romkes, M., et al., "Cloning and Expression of Complementary DNAs for Multiple Members of the Human Cytochrome P450–IIC." Biochemistry (1991) 30: 3247–3255.

DeMorias, S.M., et al., "The Major Genetic Defect Responsible for the Polymorphism of S–mephenytoin Metabolism in Humans." J. Biol. Chem. (1994) Jun. 3;269(22): 15419–22.

DeMorias, S.M., et al., "Identification of a New Genetic Defect Responsible for the Polymorphism of (S)–mephenytoin Metabolism in Japanese." Mol. Pharmacol. (1994) Oct.:46)4): 594–8.

Ibeanu, G., et al., "An Additional Defective Allele, CYP2C19*5, Contributes to the S–mephenytoin Poor Metabolizer Phenotype in Caucasians." Pharmacogenetics (1998) 8:129–135.

Ibeanu, G., et al., "Identification of New Human CYP2C19*6 and CYP2C19*2B) in a Caucasian Poor Metabolizer of Mephenytoin." J. Pharmacol. Exp. Ther. (1998) 286(3): 1490–1495.

Hu Y., et al., "Genetic Polymorphism of Human CYP2E1: Characterization of Two Variant Alleles." Mol Pharmacology (1997) 51: 370–376.

Fairbrother K., et al., Detection and Characterization of Novel Polymorphisms in the CYP2E1 Gene Pharmacogenetics (1998) 8:543–552.

Richardson, T.H., et al., A Universal Approach to the Expression of Human and Rabbit Cytochrome P450s of the 2C subfamily in *Escherichia coli* Arch BioChem BioPhys (1995) Oct. 20, 323(1): 87–96.

McBride, O.W., et al., A Taq I Polymorphism in the Human P450 IIE1 Gene on Chromosome 10 (CYP2E) Nucleic Acid Research (1987) 15 (23): 10021.

Perrson, I., et al., "Genetic Polymorphism of Cytochrome P450 2E1 in a Swedish Population: Relationship to incidence of lung cancer." FEBS Lett. (1993) 319(3): 207–211.

Umeno M., et al., Human Ethanol–Inducible P450 IIE1: Complete Gene Sequence, Promoter Characterization, Chromosome mapping, and cDNA–Directed Expression Biochemistry (1988) 27: 9006–9013.

Hayashi S., et al., Genetic Polymorphisms in the 5'–Flanking Region Change Transcriptional Regulation of the Human Cytochrome p450 IIE1 Gene J. Biochem (1991) 110: 559–565.

Kawajiri K., et al., Structure and Drug Inducibility of the Human Cytochrome P450c Gene Eur. J. Biochem (1986) 159: 219–225.

Smart J., et al., Variation in Induced CYP1A1 levels: Relationship to CYP1A1, Ah receptor and GSTM1 Polymorphisms Pharmacogenetics (2000) 10: 11–24.

Ikeya K., et al., Human CYP1A2: Sequence, Gene Structure, Comparison with the Mouse and Rat Orthologous Gene, and Differences in Liver 1A2 mRNA Expression Mol Endocrinology (1989) 3 (9): 1399–1408.

Huang J., et al., Detection of a Novel Cytochrome P450 1A2 Polymorphism (F21L) in Chinese Drug Metabolism and Disposition (1999) 27 (1): 98–101.

Stoilov I., et al., Sequence Analysis and Homology Modeling Suggest that Primary Congenital Glaucoma on 2p21 Results from Mutations Disrupting Either the Hinge Region or the Conserved Core Structures of Cytochrome P450 1B1 Am J. Hum Genet (1998) 62: 573–584.

Sullivan–Klose, T.H., et al., The Role of the CYP2C9–Leu359 Allelic Variant in the Tolbutamide Polymorphism, Pharmacogenetics (1996) 6, 341–349.

Aoyama, T., et al., Cytochrom P450 hPNC3, a Novel Cytochrome P450 IIIA Gene Product that is Differently Expressed in Adult Human Liver cDNA and Deduced Amino Acid Sequence and Distinct Specificities of cDNA–expressed hPCN1 and hPCN3 for the Metabolism of Steroid Hormones and Cyclosporine J. Biol Chem. (1989) Jun. 25; 264(18): 10388–95.

Jaiswal, A.K., et al., Human P1–450 Gene Sequence and Correlation of mRNA with Genetic Differences in Benzo[a]pyrene Metabolism Nucleic Acid Res (1985) 13(12): 4503–4520.

Hashimoto, H., et al., Gene Structure of CYP3A4, and Adult–specific Form of Cytochrome P450 in Human Livers, and its Transcriptional Control Eur J. Biochem (1993) 218 (2): 585–595.

Cascorbi, I., et al., A C4887A Polymorphism in Exon 7 of Human CYP1A1: Population Frequency, Mutation Linkages, and Impact on Lung Cancer Susceptibility. Cancer Res (1996) Nov. 1; 56(21): 4965–9.

Leathart, J.B., et al., CYP2D6 Phenotype–Genotype Relationships in African–Americans and Caucasians in Los Angeles Pharmacogenetics (1998) Dec.; 8(6): 529–41.

Chida, M., et al., "Detection of three genetic polymorphisms in the 5'–flanking region and intron 1 of human CYP1A2 in the Japanese population." Jpn J Cancer Res (1999) Sep.;90(9):899–902.

Kutyavin, I.V., et al., "Oligonucleotides Containing 2–Aminoadenaine and 2–Thiothymine Act as Selectively Binding Complementary Agents." (1996) Biochemistry 27:35(34):11170–6.

Woo, J., et al., "G/C–modified oligodeoxynucleotides with selective complementarity: synthesis and hybridization properties." Nucleic Acids Research, 1996, vol. 24, No. 13, 2470–2475.

Pastinen, T., et al., "A system for specific, high throughput genotyping by allele specific primer extension on microarrays." Genome Research, 10:1031–42 (2000).

Ayyadevara, S., et al., "Discrimination of Primer 3'–Nucleotide Mismatch by Taq DNA Polymerase during Polymerase Chain Reaction." Analytical Biochemistry 284, 11–18 (2000).

Cases, et al, "Evaluation of Different Amplification Protocols for Use in Primer–Extension Preamplification." BioTechniques 20:219–225 (Feb. 1996).

Compagno, D., et al., "Antisense Oligonucleotides Containing Modified Bases Inhibit in Vitro Translation of *Leishmania amazonensis* mRNAs by Invading the Mini–exon Hairpin." Journal of Biological Chemistry. vol. 274, No. 12, Mar. 19, 1999, 8191–8198.

Huang, M.M., "Extension of base mispairs by Taq DNA polymerase: implications for single nucleotide discrimination in PCR." Nucleic Acids Research, vol. 20, No. 17, 4567–4573 (1992).

Moran, S., et al., "Non–hydrogen boding 'terminator' nucleosides increase the 3'–end homogeneity of enzymatic RNA and DNA synthesis." Nucleic Acids Research, 1996, vol. 24, No. 11, 2044–2052.

Nyrén, Pål, et al., "Detection of Single–Base Changes Using a Bioluminometric Primer Extension Assay." Analytical Biochemistry 244, (1997) 367–373, Article No. AB969913.

Stump, M.D., et al., "The use of modified primers to eliminate cycle sequencing artifacts." Nucleic Acids Research. 1999. vol. 27, No. 23, 4642–4648.

Svyänen, A.–C., et al., "A Primer–Guided Nucleotide Incorporation Assay in the Genotyping of Apolipoprotein E." Genomics 8, 684–692 (1990).

Svyänen, A.–C., "Detection of point mutations in human genes by the solid–phase minisequencing method." Clinica Chimica Acta, International Journal of Clinical Chemistry and Medical Biochemistry, 226 (1994) 225–236.

Tindall, K.R., et al., "Fidelity of DNA Synthesis by the *Thermus aquaticus* DNA Polymerase." Biochemistry 1988, 27, 6008–6013.

Zhang, L., et al., "Whole genome amplification from a single cell: Implications for genetic analysis." Proc. Natl. Acad. Sci. USA, vol. 89, 5847–5851, Jul. 1992.

Dertinger, D., et al., "Using Phosphorothioate–Substituted RNA to Investigate the Thermodynamic Role of Phosphates in a Sequence Specific RNA–Protein Complex" Biochemistry 2000, 39, 55–63.

Smith, S.A., et al., "Probing Contacts to the DNA Backbone in the trp Repressor–Operator Sequence–Specific Protein–Nucleic Acid Complex Using Diastereomeric Methylphosphonate Analogues." Biochemistry, 1997; 36, 6046–6058.

Sutter, T.R., et al., "Complete cDNA Sequence of the Human Dioxin–inducible mRNA Identifies a New Gene Subfamily of Cytochrome P450 that Maps to Chromosome 2." J Biol Chem (1994) 269(18):13092–13099.

* cited by examiner

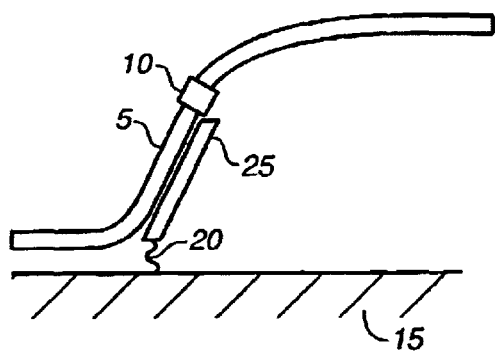
FIG._1A
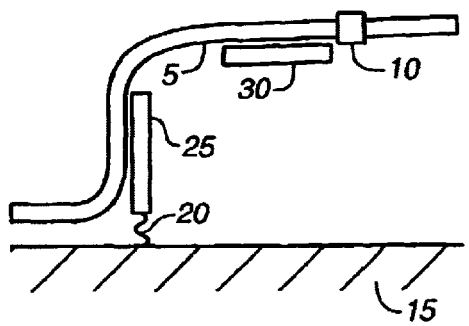
FIG._1B
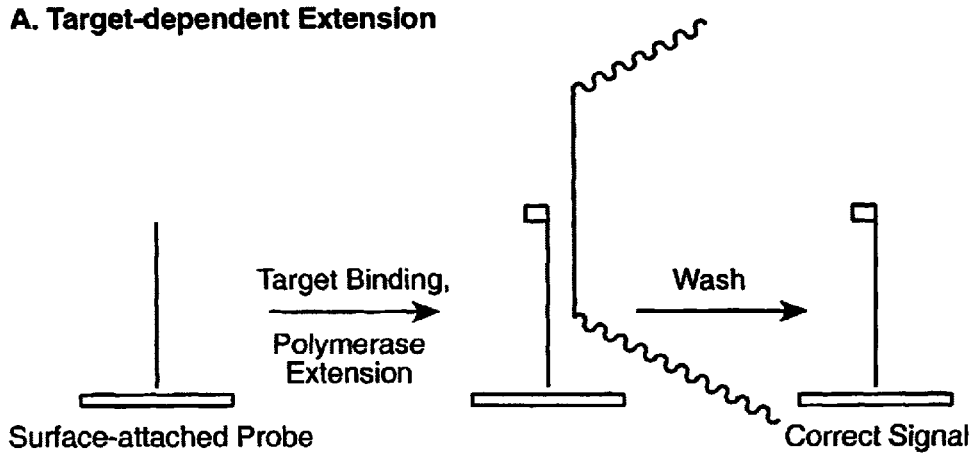
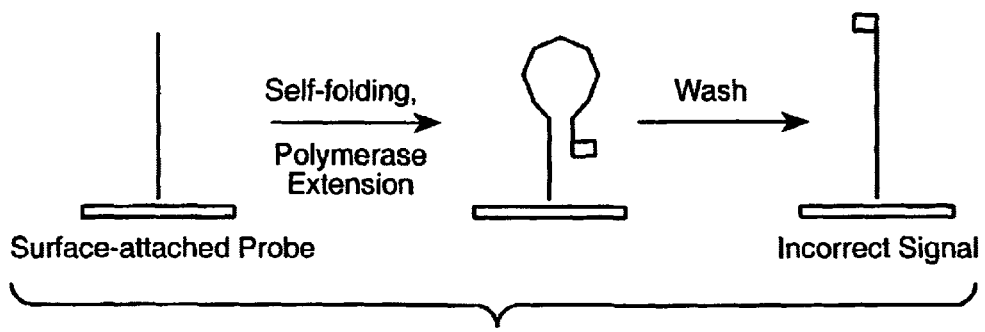
FIG._2

P450 SNP CHARACTERIZATION LIST

| SNP ID | GENE | POSITION | FROM TRANSLATION START | SEQ. SOURCE | EXON/INTRON LOCATION | MUTATION | CONSEQUENCE | ENZYME_EFFECT (IN VIVO) |
|---|---|---|---|---|---|---|---|---|
| 2D6_1618 | CYP 2D6 | 1618 | -1 | GB [M33388] | 5' FLANK | | N/A | |
| 2D6_1638 | CYP 2D6 | 1638 | 19 | GB [M33388] | EXON 1 | G>A | V 7 M | |
| 2D6_1650 | CYP 2D6 | 1650 | 31 | GB [M33388] | EXON 1 | G>A | V 11 M | |
| 2D6_1696 | CYP 2D6 | 1696 | 77 | GB [M33388] | EXON 1 | G>A | R 26 H | |
| 2D6_1701 | CYP 2D6 | 1701 | 82 | GB [M33388] | EXON 1 | C>T | R 28 C | |
| 2D6_1719 | CYP 2D6 | 1719 | 100 | GB [M33388] | EXON 1 | C>T | P 34 S | |
| 2D6_1743 | CYP 2D6 | 1743 | 124 | GB [M33388] | EXON 1 | G>A | G 42 R | |
| 2D6_1757 | CYP 2D6 | 1757 | 138 | GB [M33388] | EXON 1 | insT | FRAMESHIFT | NO ACTIVITY |
| 2D6_2502 | CYP 2D6 | 2502 | 883 | GB [M33388] | INTRON 1 | G>C | SPLICE DEFECT | |
| 2D6_2576 | CYP 2D6 | 2576 | 957 | GB [M33388] | EXON 2 | C>T | A 85 V | |
| 2D6_2593 | CYP 2D6 | 2593 | 974 | GB [M33388] | EXON 2 | C>A | L 91 M | |
| 2D6_2603 | CYP 2D6 | 2603 | 984 | GB [M33388] | EXON 2 | A>G | H 94 R | |
| 2D6_2616 | CYP 2D6 | 2616 | 997 | GB [M33388] | EXON 2 | C>G | SILENT | |
| 2D6_2642 | CYP 2D6 | 2642 | 1023 | GB [M33388] | EXON 2 | C>T | T 107 I | |
| 2D6_2658 | CYP 2D6 | 2658 | 1039 | GB [M33388] | EXON 2 | C>T | SILENT | |
| 2D6_3278 | CYP 2D6 | 3278 | 1659 | GB [M33388] | EXON 3 | G>A | V 136 R | |
| 2D6_3280 | CYP 2D6 | 3280 | 1661 | GB [M33388] | EXON 3 | G>C | SILENT | |
| 2D6_3323 | CYP 2D6 | 3323 | 1704 | GB [M33388] | EXON 3 | C>G | Q 151 E | |
| 2D6_3326 | CYP 2D6 | 3326 | 1707 | GB [M33388] | EXON 3 | T>del | FRAMESHIFT | NO ACTIVITY |
| 2D6_3343 | CYP 2D6 | 3343 | 1724 | GB [M33388] | EXON 3 | C>T | SILENT | |
| 2D6_3368 | CYP 2D6 | 3368 | 1749 | GB [M33388] | EXON 3 | A>G | N 166 D | |
| 2D6_3377 | CYP 2D6 | 3377 | 1758 | GB [M33388] | EXON 3 | G>T | G 169 STOP | |
| 2D6_3465 | CYP 2D6 | 3465 | 1846 | GB [M33388] | EXON 4 | G>A | SPLICE DEFECT | |
| 2D6_3477 | CYP 2D6 | 3477 | 1858 | GB [M33388] | EXON 4 | C>T | R 143 C | |
| 2D6_3488 | CYP 2D6 | 3488 | 1869 | GB [M33388] | EXON 4 | T>C | | |
| 2D6_3562 | CYP 2D6 | 3562 | 1943 | GB [M33388] | EXON 4 | G>A | R 201 H | |
| 2D6_3592 | CYP 2D6 | 3592 | 1973 | GB [M33388] | EXON 4 | insG | FRAMESHIFT? | |
| 2D6_3595 | CYP 2D6 | 3595 | 1976 | GB [M33388] | EXON 4 | G>A | G 212 E | |
| 2D6_3597 | CYP 2D6 | 3597 | 1978 | GB [M33388] | EXON 4 | C>T | SILENT | |
| 2D6_3598 | CYP 2D6 | 3598 | 1979 | GB [M33388] | EXON 4 | T>C | | NORMAL |

FIG._3A

P450 SNP CHARACTERIZATION LIST

| SNP ID | GENE | POSITION | FROM TRANS-LATION START | SEQ. SOURCE | EXON/INTRON LOCATION | MUTATION | CONSEQUENCE | ENZYME_EFFECT (IN VIVO) |
|---|---|---|---|---|---|---|---|---|
| 2D6_4089 | CYP 2D6 | 4089 | 2470 | GB [M33388] | EXON 5 | T>C | SILENT | |
| 2D6_4099 | CYP 2D6 | 4099 | 2480 | GB [M33388] | EXON 5 | C>T | SILENT | |
| 2D6_4102 | CYP 2D6 | 4102 | 2483 | GB [M33388] | EXON 5 | G>T | A 237 S | NORMAL |
| 2D6_4168 | CYP 2D6 | 4168 | 2549 | GB [M33388] | EXON 5 | A>del | FRAMESHIFT | NO ACTIVITY |
| 2D6_4194 | CYP 2D6 | 4194 | 2575 | GB [M33388] | EXON 5 | C>A | SILENT | |
| 2D6_4206 | CYP 2D6 | 4206 | 2587 | GB [M33388] | EXON 5 | GACT>del | FRAMESHIFT | NO ACTIVITY |
| 2D6_4232 | CYP 2D6 | 4232 | 2613 | GB [M33388] | EXON 5 | AGA>del | K 281 DEL | DECREASED |
| 2D6_4469 | CYP 2D6 | 4469 | 2850 | GB [M33388] | EXON 6 | C>T | R 296 C | |
| 2D6_4472 | CYP 2D6 | 4472 | 2853 | GB [M33388] | EXON 6 | A>C | I 297 L | |
| 2D6_4554 | CYP 2D6 | 4554 | 2935 | GB [M33388] | EXON 6 | A>C | H 324 P | NONE |
| 2D6_4557 | CYP 2D6 | 4557 | 2938 | GB [M33388] | EXON 6 | C>T | P 325 L | |
| 2D6_4558 | CYP 2D6 | 4558 | 2939 | GB [M33388] | EXON 6 | G>A | SILENT | |
| 2D6_4802 | CYP 2D6 | 4802 | 3183 | GB [M33388] | EXON 7 | G>A | V 338 M | |
| 2D6_4817 | CYP 2D6 | 4817 | 3198 | GB [M33388] | EXON 7 | C>G | R 343 G | |
| 2D6_4896 | CYP 2D6 | 4896 | 3277 | GB [M33388] | EXON 7 | T>C | I 369 T | |
| 2D6_4907 | CYP 2D6 | 4907 | 3288 | GB [M33388] | EXON 7 | G>A | G 373 S | NORMAL |
| 2D6_5447 | CYP 2D6 | 5447 | 3828 | GB [M33388] | EXON 8 | G>A | SILENT | |
| 2D6_5472 | CYP 2D6 | 5472 | 3853 | GB [M33388] | EXON 8 | G>A | E 410 K | |
| 2D6_5496 | CYP 2D6 | 5496 | 3877 | GB [M33388] | EXON 8 | G>C | E 418 Q | |
| 2D6_5506 | CYP 2D6 | 5506 | 3887 | GB [M33388] | EXON 8 | T>C | SILENT | |
| 2D6_5661 | CYP 2D6 | 5661 | 4042 | GB [M33388] | EXON 9 | G>A | R 440 H | |
| 2D6_5734 | CYP 2D6 | 5734 | 4115 | GB [M33388] | EXON 9 | C>T | SILENT | |
| 2D6_5799 | CYP 2D6 | 5799 | 4180 | GB [M33388] | EXON 9 | G>C | S 486 T | *2, *4, |
| 2E1_1532 | CYP 2E1 | 1532 | -1293 | GB [J02843] | 5' FLANK | G>C | | |
| 2E1_1627 | CYP 2E1 | 1627 | -1198 | GB [J02843] | 5' FLANK | G>C | | |
| 2E1_1772 | CYP 2E1 | 1772 | -1053 | GB [J02843] | 5' FLANK | C>T | | |
| 2E1_1800 | CYP 2E1 | 1800 | -1025 | GB [J02843] | 5' FLANK | T>C | | |
| 2E1_2019 | CYP 2E1 | 2019 | -806 | GB [J02843] | 5' FLANK | T>C | | |
| 2E1_2473 | CYP 2E1 | 2473 | -352 | GB [J02843] | 5' FLANK | A>G | | |
| 2E1_2492 | CYP 2E1 | 2492 | -333 | GB [J02843] | 5' FLANK | T>A | | |

FIG._3B

P450 SNP CHARACTERIZATION LIST

| SNP ID | GENE | POSITION | FROM TRANS-LATION START | SEQ. SOURCE | EXON/INTRON LOCATION | MUTATION | CONSEQUENCE | ENZYME_EFFECT (IN VIVO) |
|---|---|---|---|---|---|---|---|---|
| 2E1_2754 | CYP 2E1 | 2754 | -71 | GB J02843 | 5' FLANK | G>T | | |
| 2E1_3104 | CYP 2E1 | 3104 | 280 | GB J02843 | INTRON A | NONE | | |
| 2E1_3085 | CYP 2E1 | 3085 | 261 | GB J02843 | INTRON A | NONE | | |
| 2E1_3956 | CYP 2E1 | 3956 | 1132 | GB J02843 | EXON 2 | G>A | R 76 H | REDUCED |
| 2E1_7592 | CYP 2E1 | 7592 | 4768 | GB J02843 | EXON 4 | G>A | V 179 I | NORMAL |
| 2E1_10456 | CYP 2E1 | 10456 | 7632 | GB J02843 | INTRON F | T>A | | |
| 2E1_12720 | CYP 2E1 | 12720 | 9896 | GB J02843 | INTRON G | C>G | | |
| 2E1_12847 | CYP 2E1 | 12847 | 10023 | GB J02843 | EXON 8 | G>A | V 389 I | NORMAL |
| 2E1_12945 | CYP 2E1 | 12945 | 10121 | GB J02843 | EXON 8 | C>T | | |
| 3A4_816 | CYP 3A4 | 816 | -392 | GB D11131 | 5' FLANK | A>G | | |
| 3A4_918 | CYP 3A4 | 918 | -290 | GB D11131 | 5' FLANK | A>G | | |
| 1A1_1213 | CYP 1A1 | 1213 | -3229 | GB X04300 | 5' FLANK | G>A | | |
| 1A1_1223 | CYP 1A1 | 1223 | -3219 | GB X04300 | 5' FLANK | C>T | | |
| 1A1_6568 | CYP 1A1 | 6568 | 2453 | GB X04300 | EXON 7 | C>A | T 461 N | |
| 1A1_6570 | CYP 1A1 | 6570 | 2455 | GB X04300 | EXON 7 | A>G | I 462 V | |
| 1A1_7320 | CYP 1A1 | 7320 | 3205 | GB X04300 | 3' FLANK | T>C | | |
| 1A1_7916 | CYP 1A1 | 7916 | 3800 | GB X04300 | 3' FLANK/FLOATER | T>C | | |
| 1B1_3793 | CYP 1B1 | 3793 | -13 | GB U56438 | INTRON 1 (not translated) | | N/A | |
| 1B1_3947 | CYP 1B1 | 3947 | 142 | GB U56438 | EXON 2 | C>G | R 48 G | |
| 1B1_3976 | CYP 1B1 | 3976 | 171 | GB U56438 | EXON 2 | G>C | W 57 C | |
| 1B1_3987 | CYP 1B1 | 3987 | 182 | GB U56438 | EXON 2 | G>A | G 61 E | |
| 1B1_4035 | CYP 1B1 | 4035 | 230 | GB U56438 | EXON 2 | T>C | L 77 P | GLAUCOMA |
| 1B1_4160 | CYP 1B1 | 4160 | 355 | GB U56438 | EXON 2 | G>T | A 119 S | |
| 1B1_4306 | CYP 1B1 | 4306 | 501 | GB U56438 | EXON 2 | insT | FRAMESHIFT | |
| 1B1_4646 | CYP 1B1 | 4646 | 841 | GB U56438 | EXON 2 | G>T | E 281 X | |
| 1B1_4668 | CYP 1B1 | 4668 | 863 | GB U56438 | EXON 2 | insC | FRAMESHIFT | |
| 1B1_7930 | CYP 1B1 | 7930 | 4125 | GB U56438 | EXON 3 | G>T | G 365 W | |
| 1B1_7940 | CYP 1B1 | 7940 | 4135 | GB U56438 | EXON 3 | G>A | R 368 H | GLAUCOMA |
| 1B1_7957 | CYP 1B1 | 7957 | 4152 | GB U56438 | EXON 3 | G>A | D 374 N | GLAUCOMA |

*FIG._3C*

P450 SNP CHARACTERIZATION LIST

| SNP ID | GENE | POSITION | FROM TRANS-LATION START | SEQ. SOURCE | EXON/INTRON LOCATION | MUTATION | CONSEQUENCE | ENZYME_EFFECT (IN VIVO) |
|---|---|---|---|---|---|---|---|---|
| 1B1_7973 | CYP 1B1 | 7973 | 4168 | GB [U56438] | EXON 3 | C>T | P 379 L | |
| 1B1_7996 | CYP 1B1 | 7996 | 4191 | GB [U56438] | EXON 3 | G>A | E 387 K | |
| 1B1_8006 | CYP 1B1 | 8006 | 4201 | GB [U56438] | EXON 3 | G>A | R 390 H | |
| 1B1_8131 | CYP 1B1 | 8131 | 4326 | GB [U56438] | EXON 3 | C>G | L 432 V | |
| 1B1_8147 | CYP 1B1 | 8147 | 4342 | GB [U56438] | EXON 3 | C>T | P 437 L | |
| 1B1_8184 | CYP 1B1 | 8184 | 4379 | GB [U56438] | EXON 3 | T>C | 449 SILENT | |
| 1B1_8195 | CYP 1B1 | 8195 | 4390 | GB [U56438] | EXON 3 | A>G | N 453 V | |
| 1B1_8242 | CYP 1B1 | 8242 | 4437 | GB [U56438] | EXON 3 | C>T | R 469 W | |
| 1B1_8587 | CYP 1B1 | 8587 | 4782 | GB [U56438] | EXON 3 | C>G | | |
| 1B1_8807 | CYP 1B1 | 8807 | 5002 | GB [U56438] | EXON 3 | T>A | | |
| 1B1_9164 | CYP 1B1 | 9164 | 5359 | GB [U56438] | 3' FLANK | T>G | | |
| 1A2_2640 | CYP 1A2 | 2640 | -164 | GB [M31664] | INTRON A (5' FLANK) | C>A | | HIGHER INDUCIBILITY |
| 1A2_2866 | CYP 1A2 | 2866 | 63 | GB [M31664] | EXON 1 | C>G | F 21 L | |
| 2C19_99 | CYP 2C19 | 99 | 99 | GB [NM_000769] | EXON 1 | C>T | | |
| 2C19_276 | CYP 2C19 | 276 | 276 | GB [NM_000769] | EXON 2 | G>C | E 92 D | |
| 2C19_395 | CYP 2C19 | 395 | 395 | GB [NM_000769] | EXON 3 | G>A | R 132 Q | |
| 2C19_430 | CYP 2C19 | 430 | 430 | GB [NM_000769] | EXON 3 | C>T | | |
| 2C19_636 | CYP 2C19 | 636 | 636 | GB [NM_000769] | EXON 4 | G>A | STOP CODON | |
| 2C19_681 | CYP 2C19 | 681 | 681 | GB [NM_000769] | EXON 5 | G>A | SPLICE DEFECT | |

FIG._3D

| ALLELE / HAPLOTYPE FAM | IUPAC CODE | ALLELE_1 | ALLELE_2 | SNP_SOURCE INFO | |
|---|---|---|---|---|---|
| | | | | | Error / Corrections |
| *28 | R | G | A | Marez, D.: Pharmacogenetics 1997 | |
| *35 | R | G | A | Marez, D.: Pharmacogenetics 1997 | |
| *21 | R | G | A | Marez, D.: Pharmacogenetics 1997 | |
| *22 | Y | C | T | Marez, D.: Pharmacogenetics 1997 | |
| *4, *10 (*36), *14, *37 | Y | C | T | Marez, D.: Pharmacogenetics 1997 | |
| *12 | R | G | A | Marez, D.: Pharmacogenetics 1997 | |
| *15 | | | T | Sachse C.: Pharmacogenetics 1996 | |
| *11 | S | G | C | Marez, D.: Pharmacogenetics 1997 | |
| *23 | Y | C | T | Marez, D.: Pharmacogenetics 1997 | |
| *4 | M | C | A | Marez, D.: Pharmacogenetics 1997 | |
| *4 | R | A | G | Marez, D.: Pharmacogenetics 1997 | |
| *2, *4 | S | C | G | Marez, D.: Pharmacogenetics 1997 | |
| *17 | Y | C | T | Marez, D.: Pharmacogenetics 1997 | |
| *2, *4, *10 (*36), *37 | R | G | A | Marez, D.: Pharmacogenetics 1997 | |
| *29 | S | G | C | Marez, D.: Pharmacogenetics 1997 | |
| *2, *4, *8, *10 (*36), *11, *12, *19, *28, *29, *30, *31, *32, *35, *37 | S | C | G | Marez, D.: Pharmacogenetics 1997 | |
| *28 | | T | DEL | Marez, D.: Pharmacogenetics 1997 | |
| *6 | Y | C | T | Marez, D.: Pharmacogenetics 1997 | |
| *2 | R | A | G | Marez, D.: Pharmacogenetics 1997 | |
| *3 | K | G | T | Marez, D.: Pharmacogenetics 1997 | |
| *8, *14 | R | G | A | Marez, D.: Pharmacogenetics 1997 | |
| *4 | Y | C | T | Marez, D.: Pharmacogenetics 1997 | |
| *4 | Y | T | C | Marez, D.: Pharmacogenetics 1997 | |
| *1 | R | G | A | Sachse C.: Pharmacogenetics 1996 | |
| *37 | Y | T | C | Marez, D.: Pharmacogenetics 1997 | |
| *20 | | INS | G | Marez-Allorge D.: Pharmacogenetics 1999 | |
| *6 | R | G | A | Marez, D.: Pharmacogenetics 1997 | |
| *1, *20 | Y | C | T | Marez, D.: Pharmacogenetics 1997 | |
| *20 | Y | T | C | Marez-Allorge D.: Pharmacogenetics 1999 | |

FIG._3E

| ALLELE / HAPLOTYPE FAM | IUPAC CODE | ALLELE_1 | ALLELE_2 | SNP_SOURCE INFO |
|---|---|---|---|---|
| *2 | Y | T | C | Marez, D.: Pharmacogenetics 1997 |
|  | Y | C | T | Marez, D.: Pharmacogenetics 1997 |
| *33 | K | G | T | Marez, D.: Pharmacogenetics 1997 |
| *3 |  | A | DEL | Marez, D.: Pharmacogenetics 1997 |
| *1, *2 | M | C | A | Marez, D.: Pharmacogenetics 1997 |
| *35 |  | GACT | DEL | Leathart JB.: Pharmacogenetics 1998 |
|  |  | AGA | DEL | Marez, D.: Pharmacogenetics 1997 |
| *9 | Y | C | T | Marez, D.: Pharmacogenetics 1997 |
| *2,*4, *8, *11, *12, *14, *17, *19, *20, *28, *29, *30, *31, *32, *34, *35 | M | A | C | Marez, D.: Pharmacogenetics 1997 |
| *24 | M | A | C | Marez, D.: Pharmacogenetics 1997 |
| *7 | Y | C | T | Marez, D.: Pharmacogenetics 1997 |
| *4 | R | G | A | Marez, D.: Pharmacogenetics 1997 |
| *2 | R | G | A | Marez, D.: Pharmacogenetics 1997 |
| *29 | S | C | G | Marez, D.: Pharmacogenetics 1997 |
| *25 | Y | T | C | Marez, D.: Pharmacogenetics 1997 |
| *28 | R | G | A | Marez, D.: Pharmacogenetics 1997 |
| *6 | R | G | A | Marez, D.: Pharmacogenetics 1997 |
| *1 | R | G | A | Marez, D.: Pharmacogenetics 1997 |
| *27, *32 | R | G | A | Marez, D.: Pharmacogenetics 1997 |
| *4 | S | G | C | Marez, D.: Pharmacogenetics 1997 |
| *4 | Y | T | C | Yokota, H.: Pharmacogenetics 1993 |
| *31 | R | G | A | Marez, D.: Pharmacogenetics 1997 |
| *2 | Y | C | T | Marez, D.: Pharmacogenetics 1997 |
| *6, *8, *10 (*36), *11, *12, *14, *17, *19, *20, *28, *29, *30, *31, *32, *33 | S | G | C | Marez, D.: Pharmacogenetics 1997 |
| *5A, *5B | S | G | C | Hayashi, S.: J. BioChem 1991 |
|  | S | G | C | Hayashi, S.: J. BioChem 1991 |
| *5A, *5B | Y | C | T | Hayashi, S.: J. BioChem 1991 |
|  | Y | T | C | Hayashi, S.: J. BioChem 1991 |
| *7C | R | A | G | Fairbrother, KS.: Pharmacogenetics 1998 |
| *7ALL | W | T | A | Fairbrother, KS.: Pharmacogenetics 1998 |

FIG._3F

| ALLELE / HAPLOTYPE FAM | IUPAC CODE | ALLELE_1 | ALLELE_2 | SNP_SOURCE INFO |
|---|---|---|---|---|
|  | K | G | T | Fairbrother, KS.: Pharmacogenetics 1998 |
|  | G | G |  | Error / Corrections |
|  | T | T |  | Error / Corrections |
| *2 | R | G | A | Hu, Y.: Mol Pharmacology 1997 |
|  | R | G | A | Fairbrother, KS.: Pharmacogenetics 1998 |
| *5A, *6 | W | T | A | Perrson, I.: FEBS Lett 1993 |
|  | S | C | G | McBride, OW.: Nucleic Acid Res 1987 |
| *3 | R | G | A | Hu, Y.: Mol Pharmacology 1997 |
|  | Y | C | T | GeneBank SNP database, [D50111] |
|  | R | A | G | HGBASE, [SNP000000637] |
|  | R | A | G | OMIM, [124010.0001] |
| *4 | R | G | A | Smart and Daly: Pharmacogenetics 1999 |
| *2B, *2C | Y | C | T | Smart and Daly: Pharmacogenetics 1999 |
| *3 | M | C | A | Cacorbi, I.: Cancer Res 1996 |
|  | R | A | G | Hayashi, S.: J. BioChem 1991 |
|  | Y | T | C | HGBASE, [SNP000026686] |
| *2 | Y | T | C | GeneBank SNP database, [D12525] |
| *11 | S | C | G | Stoilov, I.: Am. J. Human Genetics 1998 |
| *12 | S | G | C | Stoilov, I.: Am. J. Human Genetics 1998 |
|  | R | G | A | Stoilov, I.: Am. J. Human Genetics 1998 |
| *2 | Y | T | C | Stoilov, I.: Am. J. Human Genetics 1998 |
| *13 | K | G | T | Stoilov, I.: Am. J. Human Genetics 1998 |
| *14 |  |  |  | Stoilov, I.: Am. J. Human Genetics 1998 |
| *15 | K | G | T | Stoilov, I.: Am. J. Human Genetics 1998 |
| *18 | K | G | T | Beijani: Hum Mol Genetics 2000 |
|  | R | G | A | Stoilov, I.: Am. J. Human Genetics 1998 |
|  | R | G | A | Beijani: Hum Mol Genetics 2000 |
| *19 | Y | C | T | Beijani: Am J. Hum Genetics 1998 |
|  |  |  |  | Stoilov, I.: Am. J. Human Genetics 1998 |

FIG._3G

| ALLELE / HAPLOTYPE FAM | IUPAC CODE | ALLELE_1 | ALLELE_2 | SNP_SOURCE INFO |
|---|---|---|---|---|
| *20 | R | G | A | Stoilov, I.: Am. J. Human Genetics 1998 |
|  | R | G | A | Stoilov, I.: Am. J. Human Genetics 1998 |
| *3 | S | C | G | Stoilov, I.: Am. J. Human Genetics 1998 |
|  | Y | C | T | Stoilov, I.: Am. J. Human Genetics 1998 |
|  | Y | T | C | Stoilov, I.: Am. J. Human Genetics 1998 |
| *4 | R | A | G | Stoilov, I.: Am. J. Human Genetics 1998 |
| *25 | Y | C | T | Stoilov, I.: Am. J. Human Genetics 1998 |
|  | S | C | G | HGBASE, [SNP000000547] |
|  | W | T | A | HGBASE, [SNP000001727]/ NCBI [rs2672] |
|  | K | T | G | NCBI, [rs109161] |
| *1F | M | C | A | Sachse, C.: Br J Clin Pharmacol 1999 |
| *2 | S | C | G | Huang, JD : Drug Metab Dispos 1999 |
|  | Y | C | T | Richardson, TH: Arch Biochem Biophys 1995 |
| *2B | S | G | C | Ibeanu, GC: J. Pharmacol Exp Ther 1998 |
| *6 | R | G | A | Ibeanu, GC: J. Pharmacol Exp Ther 1998 |
|  | Y | C | T | HGBASE, [SNP000000186] |
| *3 | R | G | A | De Morais, SM: Mol Pharmacol 1994 |
| *2A | R | G | A | De Morais, SM: J Biol Chem 1994 |

FIG._3H

CYP2D6 and its Pseudogenes: Similarity by Region
S. Kimura et. al. *Am J Hum Genet* (1989) 45:889-904

| | Length, bp | | | Similarity, % | | |
|---|---|---|---|---|---|---|
| | CYP2D6 | CYP2D7 | CYP2D8 | D6/D7 | D7/D8 | D6/D8 |
| UPSTREAM | 774 | 777 | | 97 | | |
| EXON 1 | 189 | | | | | |
| INTRON 1 | 268 | 186 | 265 | | 92 | 89 |
| EXON 2 | 703 | 269 | 183 | 97 | 94 | 93 |
| INTRON 2 | 172 | 701 | 186 | 98 | 90 | 89 |
| EXON 3 | 550 | 172 | 265* | 95 | 94 | 91 |
| INTRON 3 | 153 | 528 | 1620* | 74 | 78 | 77 |
| EXON 4 | 88 | 153 | 172 | 98 | 93 | 92 |
| INTRON 4 | 161 | 88 | 546 | 98 | 91 | 93 |
| EXON 5 | 433 | 161 | 153 | 98 | 89 | 91 |
| INTRON 5 | 177 | 425 | 88 | 94 | 85 | 86 |
| EXON 6 | 190 | 177 | 161 | 99 | 93 | 92 |
| INTRON 6 | 142 | 192 | 449 | 97 | 84 | 83 |
| EXON 7 | 207 | 142 | 177 | 94 | 92 | 96 |
| INTRON 7 | 188 | 194 | 186 | 82 | 87 | 90 |
| EXON 8 | 454 | 188 | 142 | 98 | 94 | 95 |
| INTRON 8 | 142 | 454 | 204 | 98 | 91 | 91 |
| EXON 9 | 98 | 142 | 185 | 99 | 96 | 96 |
| 3'-FLANKING | 252 | 98 | 449 | 100 | 97 | 97 |
| | 180 | 252 | 142 | 94 | | |
| | 538 | 180 | 96 | | 95 | 92 |
| | | 528 | 181 | 97 | | |
| | | | 181 | | | |

* 3 Alu Repeats Insertion

FIG. 4

P450 PRIMER LIST 02/22/01

| GENE SEQ ID | START POSITION | DIRECTION | SEQ_SOURCE | EXON/INTRON LOCATION | SEQUENCE |
|---|---|---|---|---|---|
| CYP 2D6 | 1278 | FORWARD | GB [M33388] | 5' FLANK | CCCAGAAGGCTTTGCAGGCTTCA |
| CYP 2D6 | 5799 | REVERSE | GB [M33388] | EXON 9 | CTCACCAGGAAAGCAAAGACACCAT |
| CYP 2E1 | 1487 | FORWARD | GB [J02843] | 5' FLANK | TGAAGCCTCTGCCAGAGGCCAA |
| CYP 2E1 | 4022 | REVERSE | GB [J02843] | EXON 2 | GAGAACTCGTCCTTGTAGTCCAGCA |
| CYP 2E1 | 7445 | FORWARD | GB [J02843] | INTRON 3 | CACCTTCTCACAGGCCTTGGTGAA |
| CYP 2E1 | 10689 | REVERSE | GB [J02843] | INTRON 6 | CACCCTGTGCCTCTGAGGTTGAA |
| CYP 2E1 | 12667 | FORWARD | GB [J02843] | INTRON 8 | CCTGACCCCTGACTGCTTTCTATCTAA |
| CYP 2E1 | 13030 | REVERSE | GB [J02843] | INTRON 8 | AGGAGTGTGGGCTGCTCCTCAA |
| CYP 3A4 | 747 | FORWARD | GB [D11131] | 5' FLANK | CTGTAGGTGTGGCTTGTTGGGATGAA |
| CYP 3A4 | 941 | REVERSE | GB [D11131] | 5' FLANK | CACACCACTCACTGACCTCCTTTGA |
| CYP 1A1 | 7080 | FORWARD | GB [X04300] | EXON 7 | CTCTGGTTACAGGAAGCTATGGGTCAA |
| CYP 1A1 | 8206 | REVERSE | GB [X04300] | 3' FLANK | CATGCAAGCTCAATGCAGGCTAGAATAGAA |
| CYP 1B1 | 3698 | FORWARD | GB [U56438] | INTRON 1 | CTCTCCACCCAACGGCACTCA |
| CYP 1B1 | 4704 | REVERSE | GB [U56438] | EXON 2 | GCAGAGAGGATAAAGGCGTCCATCA |
| CYP 1B1 | 7883 | FORWARD | GB [U56438] | EXON 3 | ATCCTGATGTGCAGACTCGAGTGCA |
| CYP 1B1 | 9235 | REVERSE | GB [U56438] | EXON 3 | CAAGCAAAAGAGGTACAACATCACCTTGGA |
| CYP 1A2 | 2595 | FORWARD | GB [M31664] | 5' FLANK | CCAGCTCTCAGATTCTGTGATGCTCAA |
| CYP 1A2 | 2972 | REVERSE | GB [M31664] | EXON 1 | GGGTCAGCACATGCCCGAGCAA |
| CYP 2C19 | 197 | FORWARD | GB [NM_000769] | EXON 2 | CTCTGTATTTGGCCTTGGAACGCATG |
| CYP 2C19 | 787 | REVERSE | GB [NM_000769] | EXON 5 | TCCCGAGGCTTGTTGATGTCCATC |

FIG._5A

P450 PRIMER LIST 02/22/01

| PRIMER LENGTH | Tm | BLAST RESULTS |
|---|---|---|
| 23 | 71 | ACCEPTABLE |
| 25 | 67 | ACCEPTABLE |
| 22 | 71 | ACCEPTABLE |
| 25 | 65 | ACCEPTABLE |
| 24 | 69 | ACCEPTABLE |
| 23 | 68 | ACCEPTABLE |
| 27 | 66 | ACCEPTABLE |
| 22 | 68 | ACCEPTABLE |
| 26 | 69 | ACCEPTABLE |
| 25 | 67 | ACCEPTABLE |
| 27 | 67 | ACCEPTABLE |
| 30 | 70 | ACCEPTABLE |
| 21 | 68 | ACCEPTABLE |
| 25 | 69 | ACCEPTABLE |
| 25 | 70 | ACCEPTABLE |
| 30 | 70 | ACCEPTABLE |
| 27 | 69 | ACCEPTABLE |
| 22 | 74 | ACCEPTABLE |
| 26 | 70 | ACCEPTABLE |
| 24 | 70 | ACCEPTABLE |

*FIG._5B*

P450 COMPILED PROBE LIST/ BETA

| PROBE ID | SEQUENCE |
|---|---|
| CYP1A1_V_2_70.6568.A.S | GCAAGCGGAAGTGTATCGGTGAGAA |
| CYP1A1_V_2_70.6568.C.S | GCAAGCGGAAGTGTATCGGTGAGAC |
| CYP1A1_60.6570.A.A | TCCCAGCGGGCAAT |
| CYP1A1_60.6570.G.A | TCCCAGCGGGCAAC |
| CYP1A1_V_2_60.7320.C.A | ATAAGGGTCTTACAAGGCCG |
| CYP1A1_V_2_60.7320.T.A | AATAAGGGTCTTACAAGGCCA |
| CYP1A2_60+1.2640.A.A | CATCTACCATGCGTCCTGTG |
| CYP1A2_60+1.2640.C.A | ATCTACCATGCGTCCTGGG |
| CYP1A2_V2.2866.C.S | TGGCCTCTGCCATCTTCT |
| CYP1A2_V2.2866.G.S | TGGCCTCTGCCATCTTG |
| CYP1A2_V3.2866.C.S | TGGCCTCTGCCATCTTCT |
| CYP1A2_V3.2866.G.S | TGGCCTCTGCCATCTTGT |
| CYP1B1_60.3793.C.A | CCATGCTGGGGACAGAG |
| CYP1B1_60.3793.T.A | CCATGCTGGGGACAGAA |
| CYP1B1_60.3947.C.S | GAGGCGGCAGCTCC |
| CYP1B1_60.3947.G.S | GAGGCGGCAGCTCG |
| CYP1B1_60.3976.C.S | GCCCGTTTGCGTGC |
| CYP1B1_60.3976.G.S | GCCCGTTTGCGTGG |
| CYP1B1_60.3987.A.A | GCCGCCGCGTTTT |
| CYP1B1_60.3987.G.A | GCCGCCGCGTTTC |
| 1B1_4035.C.S | CGTTCGCTCGCCC |
| 1B1_4035.T.S | CTCGTTCGCTCGCCT |
| CYP1B1_60+2-1.4160.G.A | GAAGGAGGCGAAGGCCG |
| CYP1B1_60+2-1.4160.T.A | GAAGGAGGCGAAGGACG |
| 1B1_V2.4306.A.A | TCAGCACGTGGCCCT |
| 1B1_V2.4306.T.A | CAGCACGTGGCCCAG |
| CYP1B1_60+1.4646.G.S | AGTTCTTGAGGCACTGCGA |
| CYP1B1_60+1.4646.T.S | CAAGTTCTTGAGGCACTGCTA |
| 1B1_4668.C.A | TCGCGGGGGGG |
| 1B1_4668.G.A | TCGCGGGGGGC |
| CYP1B1_60.7930.G.S | GAATTGGATCAGGTCGTGG |
| CYP1B1_60.7930.T.S | AGAATTGGATCAGGTCGTGT |
| 1B1_V2.7940.A.A | TGGTIACCCATACAAGGCAGAT |
| 1B1_V2.7940.G.A | GGTIACCCATACAAGGCAGACG |
| CYP1B1_60+1.7957.A.S | CGTCTGCCTTGTATGGGTAA |
| CYP1B1_60+1.7957.G.S | CGTCTGCCTTGTATGGGTGA |
| CYP1B1_60.7973.C.A | GGAAGGCCAGGACATAGG |
| CYP1B1_60.7973.T.A | AGGAAGGCCAGGACATAGA |
| CYP1B1_60.7996.A.S | TATGTCCTGGCCTTCCTTTATA |
| CYP1B1_60.7996.G.S | GTCCTGGCCTTCCTTTATG |
| CYP1B1_60+1.8131.C.S | GTCTGTGAATCATGACCCACT |
| CYP1B1_60+1.8131.G.S | GTCTGTGAATCATGACCCAGT |
| CYP1B1_60+1*.8184.C.A | GTCCTTGITGATGAGGCCGT |
| CYP1B1_60+1*.8184.T.A | GTCCTTGITGATGAGGCCAT |
| CYP1B1_60.8195.A.A | TGCTGGTCAGGTCCTTGT |
| CYP1B1_60.8195.G.A | GCTGGTCAGGTCCTTGC |
| CYP1B1_60.8242.C.S | TTCAGTGGGCAAAAGGC |
| CYP1B1_60.8242.T.S | TTTTCAGTGGGCAAAAGGT |

*FIG._6A*

P450 COMPILED PROBE LIST/ BETA

| PROBE ID | SEQUENCE |
|---|---|
| CYP1B1_60.8587.C.S | TCAATTAGCGTTTAAGGTGAGC |
| CYP1B1_60.8587.G.S | TCAATTAGCGTTTAAGGTGAGG |
| CYP1B1_60.8807.A.S | CCCAAACACTTACACCAAACA |
| CYP1B1_60.8807.T.S | ACCCAAACACTTACACCAAACT |
| CYP1B1_60+1.9164.G.S | GAGTATAGTGGGGTTCCATGAGT |
| CYP1B1_60+1.9164.T.S | GAGTATAGTGGGGTTCCATGATT |
| CYP2C19EXONS_70.276.C.A | GAAATGGCCTCTTCCAGAAAACTCG |
| CYP2C19EXONS_70.276.G.A | GGAAATGGCCTCTTCCAGAAAACTCC |
| CYP2C19EXONS_70.395.A.A | CTCCTCTTCCCCATCCCAAAATTCT |
| CYP2C19EXONS_70.395.G.A | CCTCTTCCCCATCCCAAAATTCC |
| CYP2C19EXONS_70.430.C.A | GCGGGCTTCCTCTTGAACACG |
| CYP2C19EXONS_70.430.T.A | AGCGGGCTTCCTCTTGAACACA |
| CYP2C19EXONS_60.636.A.S | GATTGTAAGCACCCCCTGA |
| CYP2C19EXONS_60.636.G.S | TTGTAAGCACCCCCTGG |
| CYP2C19EXONS_60.681.A.S | CCACTATCATTGATTATTTCCCA |
| CYP2C19EXONS_60.681.G.S | CCACTATCATTGATTATTTCCCG |
| CYP2D6_70.1638.A.S | AGGCAGITATGGGGCTAGAAGCACTGA |
| CYP2D6_70.1638.G.S | GGCAGITATGGGGCTAGAAGCACTGG |
| CYP2D6_70.1650.A.A | AGGAGCAGGAAGATGGCCACTATCAT |
| CYP2D6_70.1650.G.A | GGAGCAGGAAGATGGCCACTATCAC |
| CYP2D6_70.1696.A.S | GGACCTGATGCACCGGCA |
| CYP2D6_70.1696.G.S | GGACCTGATGCACCGGCG |
| CYP2D6_70.1701.C.A | TGIGTAGCGTGCAGCCCAGCG |
| CYP2D6_70.1701.T.A | GTGIGTAGCGTGCAGCCCAGCA |
| CYP2D6_60.1719.C.A | GGGGGCCTGGTGG |
| CYP2D6_60.1719.T.A | AGGGGGCCTGGTGA |
| CYP2D6_70.1743.A.S | CCCCCTGCCACTGCCCA |
| CYP2D6_70.1743.G.S | CCCCTGCCACTGCCCG |
| 2D6H.1757.G.S | CCCTGCCACTGCCCIGGCTGGGCAACCTG |
| 2D6H.1757.T.S | CCCTGCCACTGCCCIGGCTGGGCAACCTT |
| 2D6H_V2.1757.G.S | CCTGCCACTGCCCIGGCTGGGCAACCTGCT |
| 2D6H_V2.1757.T.S | CCTGCCACTGCCCIGGCTGGGCAACCTTCT |
| CYP2D6_60+1.2502.C.A | CGGCGCCGCAAGT |
| CYP2D6_60+1.2502.G.A | CGGCGCCGCAACT |
| CYP2D6_60+1.2502.C.S | TGACCCTCCCTCTGCACT |
| CYP2D6_60+1.2502.G.S | TGACCCTCCCTCTGCAGT |
| CYP2D6_60.2576.C.S | GCTCAATGGGCTGGC |
| CYP2D6_60.2576.T.S | GTGCTCAATGGGCTGGT |
| CYP2D6_60.2593.A.A | CGCCGIGGGTCACCAT |
| CYP2D6_60.2593.C.A | CGCCGIGGGTCACCAG |
| CYP2D6_70+*.2603.A.S | GAGGCGITGGTGACCCACG |
| CYP2D6_70+*.2603.G.S | CGAGGCGITGGTGACCCG |
| CYP2D6_60+2-1.2616.C.A | GCGGTCGGCGGT |
| CYP2D6_60+2-1.2616.G.A | GGCGGTCGGCCGT |
| CYP2D6_60+1.2642.C.S | GCCTGTGCCCATCACC |
| CYP2D6_60+1.2642.T.S | CGCCTGTGCCCATCATC |
| CYP2D6_60+2.2642.C.A | CCIAAACCCAGGATCTGGGTG |
| CYP2D6_60+2.2642.T.A | CCIAAACCCAGGATCTGGATG |

*FIG._6B*

P450 COMPILED PROBE LIST/ BETA

| PROBE ID | SEQUENCE |
|---|---|
| CYP2D6_70+1.2658.C.A | TGGGAACGCGGCCCGA |
| CYP2D6_70+1.2658.T.A | TGGGAACGCGGCCCAA |
| CYP2D6_60+1.3278.A.S | CAGAGGCGCTTCTCCAT |
| CYP2D6_60+1.3278.G.S | CAGAGGCGCTTCTCCGT |
| CYP2D6_60.3280.C.S | CAGAGGCGCTTCTCCITC |
| CYP2D6_60.3280.G.S | CAGAGGCGCTTCTCCITG |
| CYP2D6_70+1.3323.C.S | TGGGCAAGAAGTCGCTGGAGCA |
| CYP2D6_70+1.3323.G.S | TGGGCAAGAAGTCGCTGGAGGA |
| 2D6H.3326.G.A | GCIGCCTCCTCGGTCACCCC |
| 2D6H.3326.T.A | GCIGCCTCCTCGGTCACCCA |
| 2D6H_V2.3326.G.A | GCIGCCTCCTCGGTCACCCCT |
| 2D6H_V2.3326.T.A | GCIGCCTCCTCGGTCACCCAC |
| CYP2D6_70.3343.C.A | CGGCACAAAGGCAGGCG |
| CYP2D6_70.3343.T.A | GCGGCACAAAGGCAGGCA |
| CYP2D6_70.3368.A.S | TGTGCCGCCTTCGCCA |
| CYP2D6_70.3368.G.S | GTGCCGCCTTCGCCG |
| CYP2D6_70.3377.G.S | CGCCTTCGCCIACCACTCCG |
| CYP2D6_70.3377.T.S | CCGCCTTCGCCIACCACTCCT |
| CYP2D6_60.3465.A.S | CATCTCCCACCCCCAA |
| CYP2D6_60.3465.G.S | CATCTCCCACCCCCAG |
| CYP2D6_60.3477.C.A | AGAGICCGTTGGGGCG |
| CYP2D6_60.3477.T.A | AAGAGICCGTTGGGGCA |
| CYP2D6_60.3488.C.A | CGGCTTTGTCCAAGAGG |
| CYP2D6_60.3488.T.A | ACGGCTTTGTCCAAGAGA |
| CYP2D6_60.3562.A.A | CCAGCAGCCTGAGGAAGT |
| CYP2D6_60.3562.G.A | CAGCAGCCTGAGGAAGC |
| 2D6H.3592.A.S | TCAGGCTGCTGGACCTAGCTCAGGA |
| 2D6H.3592.G.S | CAGGCTGCTGGACCTAGCTCAGGGA |
| CYP2D6_60.3595.A.S | TGGACCTAGCTCAGGAGGA |
| CYP2D6_60.3595.G.S | GGACCTAGCTCAGGAGGG |
| CYP2D6_70.3597.C.S | GCTGCTGGACCTAGCTCAGGAGGIAC |
| CYP2D6_70.3597.T.S | GCTGCTGGACCTAGCTCAGGAGGIAT |
| CYP2D6_60.3598.C.A | CCCGACTCCTCCTTCG |
| CYP2D6_60.3598.T.A | GCCCGACTCCTCCTTCA |
| CYP2D6_70.4099.C.S | TCCTCCTGCAIATCCCAGCGC |
| CYP2D6_70.4099.T.S | GTCCTCCTGCAIATCCCAGCGT |
| 2D6H_V2.4168.A.S | CTGGATGAGCTGCTAACTGAGCACAGG |
| 2D6H_V2.4168.G.S | CTGGATGAGCTGCTAACTGAGCACGGG |
| 2D6H_V3.4168.A.S | GCTGGATGAGCTGCTAACTGAGCACA |
| 2D6H_V3.4168.G.S | GCTGGATGAGCTGCTAACTGAGCACGG |
| CYP2D6_70.4194.A.S | GGGACCCAGCCCAGCCA |
| CYP2D6_70.4194.C.S | GGGACCCAGCCCAGCCC |
| 2D6H.4206.G.S | GCCCAGCCICCCCGAGACCTGAGG |
| 2D6H.4206.T.S | GCCCAGCCICCCCGAGACCTGACT |
| 2D6H.4232.A.A | TGGCAGCCACTCTCACCTTCT |
| 2D6H.4232.G.A | TGGCAGCCACTCTCACCTC |
| CYP2D6_60.4469.C.S | GCTTCAATGATGAGAACCTGC |
| CYP2D6_60.4469.T.S | AGCTTCAATGATGAGAACCTGT |

FIG._6C

P450 COMPILED PROBE LIST/ BETA

| PROBE ID | SEQUENCE |
|---|---|
| CYP2D6_70.4472.A.A | GCAGAGAACAGGTCAGCCACCACTAT |
| CYP2D6_70.4472.C.A | GCAGAGAACAGGTCAGCCACCACTAG |
| CYP2D6_V3.4554.C.A | TGGGCTCACGCTGCACATCIIGAGG |
| CYP2D6_V3.4554.A.A | GCTCACGCTGCACATCIIGAT |
| CYP2D6_V2.4554.C.A | GCTCACGCTGCACATCIIGAGG |
| CYP2D6_V2.4554.A.A | GCTCACGCTGCACATCIIGAT |
| CYP2D6_70.4557.C.S | GGCCTCCTGCTCATGATCCTACITCC |
| CYP2D6_70.4557.T.S | GGGCCTCCTGCTCATGATCCTACITCT |
| CYP2D6_70.4558.A.A | TGGGCTCACGCTGCACATCT |
| CYP2D6_70.4558.G.A | GGGCTCACGCTGCACATCC |
| CYP2D6_70.4802.A.S | GTGTCCAACAGGAGATCGACGACA |
| CYP2D6_70.4802.G.S | TGTCCAACAGGAGATCGACGACG |
| CYP2D6_70+*.4817.C.S | TCGACGACITGATAGGGCAGGTGCGG |
| CYP2D6_70+*.4817.G.S | ATCGACGACITGATAGGGCAGGTGGG |
| CYP2D6_70.4896.C.S | TGCAGCGCTTTGGGGACAC |
| CYP2D6_70.4896.T.S | GTGCAGCGCTTTGGGGACAT |
| CYP2D6_60.4907.A.S | GGACAICGTCCCCCTGA |
| CYP2D6_60.4907.G.S | GGACAICGTCCCCCTGG |
| CYP2D6_70.5447.A.A | AGACGGCCTCATCCTTCAGCACT |
| CYP2D6_70.5447.G.A | ACGGCCTCATCCTTCAGCACC |
| CYP2D6_70.5472.A.S | CTGAAGGATGAGGCCGTCTGGA |
| CYP2D6_70.5472.G.S | TGAAGGATGAGGCCGTCTGGG |
| CYP2D6_70.5496.C.S | CCTTCCGCTTCCACCCCC |
| CYP2D6_70.5496.G.S | CCTTCCGCTTCCACCCCG |
| CYP2D6_70+1.5506.C.S | CGCTTCCACCCCIAACACTTCCCG |
| CYP2D6_70+1.5506.T.S | CCGCTTCCACCCCIAACACTTCCTG |
| CYP2D6_70+1.5661.A.S | CCCCTCCCCACAGGCCAC |
| CYP2D6_70+1.5661.G.S | CCCTCCCCACAGGCCGC |
| CYP2D6_70.5734.C.A | CAGTGGGCACCGAGAAGCTG |
| CYP2D6_70.5734.T.A | TCCAGTGGGCACCGAGAAGCTA |
| CYP2E1_60-1+1.1532.C.A | CTGCACCTAACACTGCAGC |
| CYP2E1_60-1+1.1532.G.A | CTGCACCTAACACTGCACC |
| CYP2E1_60.1627.C.A | CATTCTATACTTGTATTTATACAAAAATGAGAG |
| CYP2E1_60.1627.G.A | CATTCTATACTTGTATTTATACAAAAATGAGAC |
| CYP2E1_V2.1772.C.A | TCTTAATTCATAGGTTGCAATTTTGTA |
| CYP2E1_V2.1772.T.A | TTCTTAATTCATAGGTTGCAATTTTATA |
| CYP2E1_V3.1800.T.S | TTGCAACCTATGAATTAAGAACTTCTA |
| CYP2E1_V3.1800.C.S | ATTGCAACCTATGAATTAAGAACTCC |
| CYP2E1_60+1.2019.C.A | GATTTGTTTTACATTAGGGTAAATTTGG |
| CYP2E1_60+1.2019.T.A | GGATTTGTTTTACATTAGGGTAAATTTAG |
| 2E1_2492.A.A | GTGGGGTGAGGTACCGT |
| 2E1_2492.T.A | GTGGGGTGAGGTACCGA |
| 2E1_2492.A.S | TGCCAAAGGGCAGGA |
| 2E1_2492.T.S | GTGCCAAAGGGCAGGT |
| 2E1_2473.A.A | GCCCTTTGGCACTGGT |
| 2E1_2473.G.A | CCCTTTGGCACTGGC |
| 2E1_2473.A.S | GGAGTTCCCCGTTGTCTAA |
| 2E1_2473.G.S | GGAGTTCCCCGTTGTCTAG |

*FIG._6D*

P450 COMPILED PROBE LIST/ BETA

| PROBE ID | SEQUENCE |
|---|---|
| CYP2E1_60.2754.G.S | GGGTCACCCTCCTTCTCAG |
| CYP2E1_60.2754.T.S | GGGTCACCCTCCTTCTCAT |
| CYP2E1_60+2.3956.A.S | GTGGGCTCGCAGCACA |
| CYP2E1_60+2.3956.G.S | TGGGCTCGCAGCGCA |
| CYP2E1_V2.3956.A.A | CCGTGCATCACCACCATGT |
| CYP2E1_V2.3956.G.A | GTGCATCACCACCATGCG |
| CYP2E1_60.10456.A.S | CACACCCAGCTGATTAAAAATTA |
| CYP2E1_60.10456.T.S | CACACCCAGCTGATTAAAAATTT |
| CYP2E1_60.12720.C.S | TCACTAAGCAACTCCTTCAACTC |
| CYP2E1_60.12720.G.S | TCACTAAGCAACTCCTTCAACTG |
| CYP2E1_60.12847.A.S | TTTCTCCTAGGGCACAGTCA |
| CYP2E1_60.12847.G.S | TCTCCTAGGGCACAGTCG |
| CYP2E1_60.12945.C.A | GGCTTGAAATAGTCACTGTACTTG |
| CYP2E1_60.12945.T.A | AATGGCTTGAAATAGTCACTGTACTTA |
| CYP3A4_60.816.A.S | GCCATAGAGACAAGGGCAA |
| CYP3A4_60.816.G.S | GCCATAGAGACAAGGGCAG |
| CYP3A4_60.918.A.S | CCAGTAACATTGATTGAGTTGTTTA |
| CYP3A4_60.918.G.S | CAGTAACATTGATTGAGTTGTTTG |
| Amplicon Control Probes | |
| 1A1.23F22R_A.X.A | GCAGGATCCCTTAGGCTTG |
| 1A1.23F22R_B.X.S | AGCCAGGAGGCCTGCTA |
| 1A2.5F3R_A.X.S | TATCCAGCTGGGAGCCAA |
| 1A2.5F3R_B.X.S | CCAGCCCCATGGCTCT |
| 1B1.2F4R_A.X.S | CACGACGACCCCGAGTT |
| 1B1.2F4R_B.X.S | CGGTGCGCACCGTT |
| 1B1.8F11R_A.X.A | TTGGGTTGGCCCTGAA |
| 1B1.8F11R_B.X.S | TGGGCTATGCAGGAGCTT |
| 2C19.3F6R_A.X.A | GCACAGCCCAGGATGAA |
| 2C19.3F6R_B.X.A | CATGCAGCACCACCATG |
| 2D6.1F1R_A.X.S | AGCCCATTTGGTAGTGAGGCAGG |
| 2D6.1F1R_B.X.S | GAGCCCATTTGGTAGTGAGGCAGA |
| 2E1.1F6R_A.X.A | AGGTGGTATTGAACAACCACAA |
| 2E1.1F6R_B.X.A | ATTCAGGTAATTCACAACAGGC |
| 2E1.8F19R_A.X.S | GACTGTGGCCGACCTGTT |
| 2E1.8F19R_B.X.S | GCACAGTGCAGAGCGCTT |
| 2E1.11F13R_A.X.S | CCAGATGAAAGCCCACATT |
| 2E1.11F13R_B.X.S | AAGCCCACATTTTGTTAACATG |
| 3A4.1F1R_A.X.S | GCTTGTTGGGATGAATTTCAA |
| 3A4.1F1R_B.X.S | CTGATAAGAACCCAGAACCCTT |

FIG._6E

Beta SNP Content List

| | | | | Comments |
|---|---|---|---|---|
| 1A1 | | | | |
| NONE | CYP 1A1 | 1213 | CYP1A1_V_2_60.1213.A.S | CYP1A1_V_2_60.1213.G.S | No Amplicon Coverage |
| NONE | CYP 1A1 | 1223 | CYP1A1_V_2_60.1223.C.A | CYP1A1_V_2_60.1223.T.A | No Amplicon Coverage |
| 23F22R | CYP 1A1 | 6568 | CYP1A1_V_2_70.6568.A.S | CYP1A1_V_2_70.6568.C.S | |
| 23F22R | CYP 1A1 | 6570 | CYP1A1_V_2_70.6570.A.A | CYP1A1_V_2_70.6570.G.A | Remove unneeded redundancy |
| 23F22R | CYP 1A1 | 7320 | CYP1A1_V_2_60.7320.C.A | CYP1A1_V_2_60.7320.T.A | |
| NONE | CYP 1A1 | 7547 | CYP1A1_60+1.7547.A.S | CYP1A1_60+1.7547.T.S | No Amplicon Coverage |
| 23F22R | CYP 1A1 | CNTRL | 1A1.23F22R_A.X.A | | Independent Amplicon Controls |
| 23F22R | CYP 1A1 | CNTRL | 1A1.23F22R_B.X.S | | Independent Amplicon Controls |
| 1A2 | | | | | |
| 5F3R | CYP 1A2 | 2640 | CYP1A2_60+1.2640.A.A | CYP1A2_60+1.2640.C.A | Redesign to overcome possible selfX |
| 5F3R | CYP 1A2 | 2640 | CYP1A2_60+#.2640.A.A | CYP1A2_60+#.2640.C.A | Remove unneeded redundancy |
| 5F3R | CYP 1A2 | 2866 | CYP1A2_V2.2866.C.S | CYP1A2_V2.2866.G.S | Redesign of one Probe (CYP1A2_V2.2866.GS = CYP1A2_60.2866.GS |
| | | | CYP1A2_V3.2866.C.S | CYP1A2_V3.2866.G.S | |
| 5F3R | CYP 1A2 | CNTRL | 1A2.5F3R_A.X.S | | Independent Amplicon Controls |
| 5F3R | CYP 1A2 | CNTRL | 1A2.5F3R_B.X.S | | Independent Amplicon Controls |
| 1B1 | | | | | |
| 2F4R | CYP 1B1 | 3793 | CYP1B1_60.3793.C.A | CYP1B1_60.3793.T.A | |
| 2F4R | CYP 1B1 | 3947 | CYP1B1_60.3947.C.S | CYP1B1_60.3947.G.S | |
| 2F4R | CYP 1B1 | 3976 | CYP1B1_60.3976.C.S | CYP1B1_60.3976.G.S | |
| 2F4R | CYP 1B1 | 3987 | CYP1B1_60.3987.A.A | CYP1B1_60.3987.G.A | |
| 2F4R | CYP 1B1 | 4035 | 1B1_4035.C.S | 1B1_4035.T.S | Newly Identified SNP |
| 2F4R | CYP 1B1 | 4160 | CYP1B1_60+2-1.4160.G.A | CYP1B1_60+2-1.4160.T.A | Redesigned to overcome GG self extension |
| 2F4R | CYP 1B1 | 4306 | 1B1_V2.4306.A.A | 1B1_V2.4306.T.A | Newly Identified SNP |
| 2F4R | CYP 1B1 | 4646 | CYP1B1_60+1.4646.G.S | CYP1B1_60+1.4646.T.S | |
| 2F4R | CYP 1B1 | 4668 | 1B1_4668.C.A | 1B1_4668.G.A | Newly Identified SNP |
| 2F4R | CYP 1B1 | CNTRL | 1B1.2F4R_A.X.S | | Independent Amplicon Controls |
| 2F4R | CYP 1B1 | CNTRL | 1B1.2F4R_B.X.S | | Independent Amplicon Controls |

FIG._7

| SNP_ID | PROBE ID |
|---|---|
| 2E1_1772 | CYP2E1_60.1772.C.A |
| 2E1_1772 | CYP2E1_60.1772.T.A |
| 2E1_2019 | CYP2E1_60.2019.C.S |
| 2E1_2019 | CYP2E1_60.2019.T.S |
| 2E1_2754 | CYP2E1_60.2754.G.S |
| 2E1_2754 | CYP2E1_60.2754.T.S |
| 2E1_3085 | CYP2E1_60.3085.A.A |
| 2E1_3085 | CYP2E1_60.3085.T.A |
| 2E1_3104 | CYP2E1_60.3104.A.A |
| 2E1_3104 | CYP2E1_60.3104.G.A |
| 2E1_7592 | CYP2E1_60.7592.A.S |
| 2E1_7592 | CYP2E1_60.7592.G.S |
| 2E1_10456 | CYP2E1_60.10456.A.S |
| 2E1_10456 | CYP2E1_60.10456.T.S |
| 2E1_12720 | CYP2E1_60.12720.C.S |
| 2E1_12720 | CYP2E1_60.12720.G.S |
| 2E1_12847 | CYP2E1_60.12847.A.S |
| 2E1_12847 | CYP2E1_60.12847.G.S |
| 2E1_12945 | CYP2E1_60.12945.C.A |
| 2E1_12945 | CYP2E1_60.12945.T.A |
| 2D6_4802 | CYP2D6_70.4802.A.S |
| 2D6_4802 | CYP2D6_70.4802.G.S |
| 2D6_4896 | CYP2D6_70.4896.C.S |
| 2D6_4896 | CYP2D6_70.4896.T.S |
| 2D6_4907 | CYP2D6_60.4907.A.S |
| 2D6_4907 | CYP2D6_60.4907.G.S |
| 2D6_4907 | CYP2D6_70.4907.A.S |
| 2D6_4907 | CYP2D6_70.4907.G.S |
| 2D6_5447 | CYP2D6_70.5447.A.A |
| 2D6_5447 | CYP2D6_70.5447.G.A |
| 2D6_5472 | CYP2D6_70.5472.A.S |
| 2D6_5472 | CYP2D6_70.5472.G.S |
| 2D6_3595 | CYP2D6_60.3595.A.A |
| 2D6_3595 | CYP2D6_60.3595.G.A |
| 2D6_3595 | CYP2D6_60.3595.A.S |
| 2D6_3595 | CYP2D6_60.3595.G.S |
| 2D6_3597 | CYP2D6_70.3597.C.S |
| 2D6_3597 | CYP2D6_70.3597.T.S |
| 2D6_3598 | CYP2D6_60.3598.C.A |
| 2D6_3598 | CYP2D6_60.3598.T.A |
| 2D6_4089 | CYP2D6_70.4089.C.S |
| 2D6_4089 | CYP2D6_70.4089.T.S |
| 2D6_4099 | CYP2D6_70.4099.C.S |
| 2D6_4099 | CYP2D6_70.4099.T.S |
| 2D6_4102 | CYP2D6_70.4102.G.A |
| 2D6_4102 | CYP2D6_70.4102.T.A |
| 2D6_2642 | CYP2D6_60.2642.C.S |
| 2D6_2642 | CYP2D6_60.2642.T.S |

FIG._8A

| SNP_ID | PROBE ID |
|---|---|
| 2D6_2642 | CYP2D6_70.2642.C.S |
| 2D6_2642 | CYP2D6_70.2642.T.S |
| 2D6_2658 | CYP2D6_70.2658.C.A |
| 2D6_2658 | CYP2D6_70.2658.T.A |
| 2D6_3278 | CYP2D6_60.3278.A.S |
| 2D6_3278 | CYP2D6_60.3278.G.S |
| 2D6_3280 | CYP2D6_60.3280.C.S |
| 2D6_3280 | CYP2D6_60.3280.G.S |
| 2D6_3343 | CYP2D6_70.3343.C.A |
| 2D6_3343 | CYP2D6_70.3343.T.A |
| 2D6_1618 | CYP2D6_70.1618.A.S |
| 2D6_1618 | CYP2D6_70.1618.G.S |
| 2D6_1638 | CYP2D6_70.1638.A.S |
| 2D6_1638 | CYP2D6_70.1638.G.S |
| 2D6_1650 | CYP2D6_70.1650.A.A |
| 2D6_1650 | CYP2D6_70.1650.G.A |
| 2D6_1696 | CYP2D6_70.1696.A.S |
| 2D6_1696 | CYP2D6_70.1696.G.S |
| 2D6_1701 | CYP2D6_70.1701.T.A |
| 2D6_1701 | CYP2D6_70.1701.C.A |
| 2D6_1719 | CYP2D6_60.1719.C.A |
| 2D6_1719 | CYP2D6_60.1719.T.A |
| 2D6_1743 | CYP2D6_70.1743.A.S |
| 2D6_1743 | CYP2D6_70.1743.G.S |
| 2D6_2502 | CYP2D6_60.2502.C.A |
| 2D6_2502 | CYP2D6_60.2502.G.A |
| 2D6_2576 | CYP2D6_60.2576.T.S |
| 2D6_2576 | CYP2D6_60.2576.C.S |
| 2D6_2593 | CYP2D6_60.2593.A.A |
| 2D6_2593 | CYP2D6_60.2593.C.A |
| 2D6_2603 | CYP2D6_70.2603.A.S |
| 2D6_2603 | CYP2D6_70.2603.G.S |
| 2D6_2616 | CYP2D6_60.2616.C.A |
| 2D6_2616 | CYP2D6_60.2616.G.A |
| 2D6_3368 | CYP2D6_70.3368.A.S |
| 2D6_3368 | CYP2D6_70.3368.G.S |
| 2D6_3377 | CYP2D6_70.3377.G.S |
| 2D6_3377 | CYP2D6_70.3377.T.S |
| 2D6_3465 | CYP2D6_60.3465.A.A |
| 2D6_3465 | CYP2D6_60.3465.G.A |
| 2D6_3465 | CYP2D6_60.3465.A.S |
| 2D6_3465 | CYP2D6_60.3465.G.S |
| 2D6_3465 | CYP2D6_70.3465.A.A |
| 2D6_3465 | CYP2D6_70.3465.G.A |
| 2D6_3465 | CYP2D6_70.3465.A.S |
| 2D6_3465 | CYP2D6_70.3465.G.S |
| 2D6_3477 | CYP2D6_60.3477.C.A |
| 2D6_3477 | CYP2D6_60.3477.T.A |

*FIG._8B*

| SNP_ID | PROBE ID |
|---|---|
| 2D6_3488 | CYP2D6_60.3488.C.A |
| 2D6_3488 | CYP2D6_60.3488.T.A |
| 2D6_3562 | CYP2D6_60.3562.A.A |
| 2D6_3562 | CYP2D6_60.3562.G.A |
| 2D6_4194 | CYP2D6_70.4194.A.S |
| 2D6_4194 | CYP2D6_70.4194.C.S |
| 2D6_4469 | CYP2D6_60.4469.C.S |
| 2D6_4469 | CYP2D6_60.4469.T.S |
| 2D6_4472 | CYP2D6_70.4472.A.A |
| 2D6_4472 | CYP2D6_70.4472.C.A |
| 2D6_4472 | CYP2D6_70.4472.A.S |
| 2D6_4472 | CYP2D6_70.4472.C.S |
| 2D6_4554 | CYP2D6_70.4554.A.A |
| 2D6_4554 | CYP2D6_70.4554.C.A |
| 2D6_4557 | CYP2D6_70.4557.C.S |
| 2D6_4557 | CYP2D6_70.4557.T.S |
| 2D6_4558 | CYP2D6_70.4558.A.A |
| 2D6_4558 | CYP2D6_70.4558.G.A |
| 2D6_5496 | CYP2D6_70.5496.C.S |
| 2D6_5496 | CYP2D6_70.5496.G.S |
| 2D6_5506 | CYP2D6_60.5506.C.A |
| 2D6_5506 | CYP2D6_60.5506.T.A |
| 2D6_5661 | CYP2D6_70.5661.A.S |
| 2D6_5661 | CYP2D6_70.5661.G.S |
| 2D6_5734 | CYP2D6_70.5734.C.A |
| 2D6_5734 | CYP2D6_70.5734.T.A |
| 2D6_5799 | CYP2D6_60.5799.C.S |
| 2D6_5799 | CYP2D6_60.5799.G.S |
| 2E1_1627 | CYP2E1_60.1627.C.A |
| 2E1_1627 | CYP2E1_60.1627.G.A |
| 3A4_816 | CYP3A4_60.816.G.S |
| 3A4_816 | CYP3A4_60.816.A.S |
| 3A4_918 | CYP3A4_60.918.A.S |
| 3A4_918 | CYP3A4_60.918.G.S |
| 2C19_430 | CYP2C19EXONS_70.430.C.A |
| 2C19_430 | CYP2C19EXONS_70.430.T.A |
| 2C19_636 | CYP2C19EXONS_60.636.A.S |
| 2C19_636 | CYP2C19EXONS_60.636.G.S |
| 2C19_681 | CYP2C19EXONS_60.681.A.S |
| 2C19_681 | CYP2C19EXONS_60.681.G.S |
| 1B1_4160 | CYP1B1_60.4160.G.A |
| 1B1_4160 | CYP1B1_60.4160.T.A |
| 1B1_7973 | CYP1B1_60.7973.C.A |
| 1B1_7973 | CYP1B1_60.7973.T.A |
| 1B1_7996 | CYP1B1_60.7996.A.S |
| 1B1_7996 | CYP1B1_60.7996.G.S |
| 1B1_8006 | CYP1B1_60.8006.A.S |
| 1B1_8006 | CYP1B1_60.8006.G.S |

*FIG._8C*

| SNP_ID | PROBE ID |
|---|---|
| 1B1_8195 | CYP1B1_60.8195.A.A |
| 1B1_8195 | CYP1B1_60.8195.G.A |
| 1B1_8242 | CYP1B1_60.8242.C.S |
| 1B1_8242 | CYP1B1_60.8242.T.S |
| 1B1_8587 | CYP1B1_60.8587.C.S |
| 1B1_8587 | CYP1B1_60.8587.G.S |
| 1A1_1223 | CYP1A1_60.1223.C.A |
| 1A1_1223 | CYP1A1_60.1223.T.A |
| 2D6_3326 | 2D6_66.3326.G.A |
| 2D6_3326 | 2D6_66.3326.T.A |
| 2D6_3326 | 2D6_66.3326.G.S |
| 2D6_3326 | 2D6_66.3326.T.S |
| 2D6_4168 | 2D6_66.4168.A.A |
| 2D6_4168 | 2D6_66.4168.C.A |
| 2D6_4168 | 2D6_66.4168.A.S |
| 2D6_4168 | 2D6_66.4168.C.S |
| 1A1_6568 | CYP1A1_60.6568.A.A |
| 1A1_6568 | CYP1A1_60.6568.C.A |
| 1A1_6568 | CYP1A1_60.6568.A.S |
| 1A1_6568 | CYP1A1_60.6568.C.S |
| 1A1_6570 | CYP1A1_60.6570.A.A |
| 1A1_6570 | CYP1A1_60.6570.G.A |
| 1A2_2640 | CYP1A2_60.2640.A.A |
| 1A2_2640 | CYP1A2_60.2640.C.A |
| 1A2_2866 | CYP1A2_60.2866.C.S |
| 1A2_2866 | CYP1A2_60.2866.G.S |
| 1B1_3793 | CYP1B1_60.3793.C.A |
| 1B1_3793 | CYP1B1_60.3793.T.A |
| 1B1_3793 | CYP1B1_60.3793.C.S |
| 1B1_3793 | CYP1B1_60.3793.T.S |
| 1B1_3947 | CYP1B1_60.3947.C.S |
| 1B1_3947 | CYP1B1_60.3947.G.S |
| 1B1_3976 | CYP1B1_60.3976.C.S |
| 1B1_3976 | CYP1B1_60.3976.G.S |
| 1B1_3987 | CYP1B1_60.3987.A.A |
| 1B1_3987 | CYP1B1_60.3987.G.A |
| 1B1_8807 | CYP1B1_60.8807.A.S |
| 1B1_8807 | CYP1B1_60.8807.T.S |
| 2C19_276 | CYP2C19EXONS_70.276.C.A |
| 2C19_276 | CYP2C19EXONS_70.276.G.A |
| 2C19_395 | CYP2C19EXONS_70.395.A.A |
| 2C19_395 | CYP2C19EXONS_70.395.G.A |
|  | CONTROL PROBES |
|  | PBR322WSNPS.4056.C.S |
|  | PBR322WSNPS.4056.T.S |
|  | WIAF-1648.107.A.A |
|  | WIAF-1648.107.G.A |

*FIG._8D*

| SNP_ID | PROBE ID |
|---|---|
| | WIAF-198.38.C.A |
| | WIAF-198.38.T.A |
| | 2D7PSEUDOGENECONTROL_60.111.C.A |
| | 2D7PSEUDOGENECONTROL_60.111.G.A |
| | 2D7PSEUDOGENECONTROL_60.111.C.S |
| | 2D7PSEUDOGENECONTROL_60.111.G.S |
| | 2D7APSEUDOGENECONTROL_60.23.A.A |
| | 2D7APSEUDOGENECONTROL_60.23.G.A |
| | 2D7APSEUDOGENECONTROL_60.2370.A.S |
| | 2D7APSEUDOGENECONTROL_60.2370.G.S |
| | 2D7APSEUDOGENECONTROL_60.2592.C.S |
| | 2D7APSEUDOGENECONTROL_60.2592.T.S |
| | 2D7APSEUDOGENECONTROL_60.3471.C.A |
| | 2D7APSEUDOGENECONTROL_60.3471.T.A |
| | 2D7PSEUDOGENECONTROL_60.600.G.S |
| | 2D7PSEUDOGENECONTROL_60.600.T.S |
| | 2D7PSEUDOGENECONTROL_60.1760.C.S |
| | 2D7PSEUDOGENECONTROL_60.1760.T.S |
| | 2D7PSEUDOGENECONTROL_60.2108.A.S |
| | 2D7PSEUDOGENECONTROL_60.2108.G.S |
| | 2D7B_60.3539.G.S |
| | 2D7B_60.3539.T.S |
| | 2D7B_60.3647.A.A |
| | 2D7B_60.3647.G.A |
| | 2D7B_60.3766.A.S |
| | 2D7B_60.3766.C.S |
| | 2D7B_60.4506.C.S |
| | 2D7B_60.4506.G.S |
| | 2D8_60.105.A.A |
| | 2D8_60.105.G.A |
| | 2D8_60.3080.A.S |
| | 2D8_60.3080.G.S |
| | 2D7PSEUDOGENECONTROL_60.1360.C.S |
| | 2D7PSEUDOGENECONTROL_60.1360.T.S |
| | 2D7PSEUDOGENECONTROL_60.3030.A.S |
| | 2D7PSEUDOGENECONTROL_60.3030.G.S |
| | 2D7PSEUDOGENECONTROL_60.3148.A.S |
| | 2D7PSEUDOGENECONTROL_60.3148.G.S |
| | 2D7B_60.442.C.A |
| | 2D7B_60.442.T.A |
| | 2D7B_60.652.G.S |
| | 2D7B_60.652.T.S |
| | 2D7B_60.1185.G.S |
| | 2D7B_60.1185.T.S |
| | 2D7B_60.1316.A.A |
| | 2D7B_60.1316.C.A |
| | 2D7B_60.1671.A.A |
| | 2D7B_60.1671.T.A |

*FIG._8E*

| SNP_ID | PROBE ID |
|---|---|
| | 2D7B_60.3172.C.S |
| | 2D7B_60.3172.G.S |
| | 2D8_60.3181.A.A |
| | 2D8_60.3181.G.A |
| | 2D8_60.4120.A.A |
| | 2D8_60.4120.G.A |
| | 2D8_60.4199.C.A |
| | 2D8_60.4199.T.A |
| | 2D8_60.4223.C.S |
| | 2D8_60.4223.T.S |
| | 2D8_60.4750.C.A |
| | 2D8_60.4750.G.A |

*FIG._8F*

| GENE | RELATED / MAPPED TOGETHER | DNA / mRNA / PARTIALS | ACCESSION # |
|---|---|---|---|
| 2D6 | 2D6 | gDNA | M33388 |
|  | 2D7 | gDNA | M33387 |
|  | 2D7A | gDNA | X58467 |
|  | 2D7B | gDNA | X58468 |
|  | 2D8 | gDNA | M33387 |
| 2E1 | 2E1 | gDNA | J02843 |
| 3A4 | 3A4 | Partial | D11131 |
|  |  | gDNA | AF209389 |
| 3A5 | 3A5 | gDNA | AC005020 |
|  |  | mRNA | NM_000777 |
|  | 3A5P | Splice Variant (mRNA) | L26985 |
| 1A1 | 1A1 | gDNA | X04300 |
|  |  | gDNA | X02612 |
|  |  | Partial | D12525 |
| 1A2 | 1A2 | Partial gDNA | M31664 |
|  |  | Partial gDNA | M31665 |
|  |  | Partial gDNA | M31666 |
|  |  | Partial gDNA | M31667 |
| 1B1 | 1B1 | gDNA | U56438 |
| 2C9 | 2C9 | mRNA | M61855 |
|  | 2C9 | Partial gDNA | L16877 |
|  | 2C9 | Partial gDNA | L16878 |
|  | 2C9 | Partial gDNA | L16879 |
|  | 2C9 | Partial gDNA | L16880 |
|  | 2C9 | Partial gDNA | L16881 |
|  | 2C9 | Partial gDNA | L16882 |
|  | 2C9 | Partial gDNA | L16883 |
|  | 2C19 | mRNA | NM_000769 |
|  | 2C19 | Draft gDNA (Exons 8-9) | AL133513 |
|  | 2C18 | mRNA | M61856 |
|  | 2C8 | mRNA | NM_000770 |
| 2C19 | 2C19 | mRNA | NM_000769 |
|  | 2C19 | Partial gDNA (Exons 8-9) | AL133513 |
|  | 2C9 | mRNA | M61855 |
|  | 2C9 | Partial gDNA | L16877 |
|  | 2C9 | Partial gDNA | L16878 |
|  | 2C9 | Partial gDNA | L16879 |
|  | 2C9 | Partial gDNA | L16880 |

*FIG._9A*

| GENE | RELATED / MAPPED TOGETHER | DNA / mRNA / PARTIALS | ACCESSION # |
|---|---|---|---|
| | 2C9 | Partial gDNA | L16881 |
| | 2C9 | Partial gDNA | L16882 |
| | 2C9 | Partial gDNA | L16883 |
| | | | |
| | 2C18 | mRNA | M61856 |
| | 2C8 | mRNA | NM_000770 |

FIG._9B

| AMPLICON | LENGTH | SNP_ID |
|---|---|---|
| 1A1_23F_22R | 1127 | 1A1_6568 |
| | | 1A1_6570 |
| | | 1A1_7320 |
| 1A2_05F_03R | 378 | 1A2_2640 |
| | | 1A2_2866 |
| 1B1_02F_04R | 1007 | 1B1_3793 |
| | | 1B1_3947 |
| | | 1B1_3976 |
| | | 1B1_3987 |
| | | 1B1_4160 |
| | | 1B1_4646 |
| 1B1_08F_11R | 1353 | 1B1_7930 |
| | | 1B1_7957 |
| | | 1B1_7973 |
| | | 1B1_7996 |
| | | 1B1_8006 |
| | | 1B1_8131 |
| | | 1B1_8147 |
| | | 1B1_8184 |
| | | 1B1_8195 |
| | | 1B1_8242 |
| | | 1B1_8587 |
| | | 1B1_8807 |
| | | 1B1_9164 |
| 2C19_03F_06R | ~6500 | 2C19_276 |
| | | 2C19_395 |
| | | 2C19_430 |
| | | 2C19_636 |
| | | 2C19_681 |
| 2D6_01F_01R | 4522 | 2D6_1618 |
| | | 2D6_1638 |
| | | 2D6_1650 |
| | | 2D6_1696 |
| | | 2D6_1701 |
| | | 2D6_1719 |

FIG._10A

| AMPLICON | LENGTH | SNP_ID |
|---|---|---|
| | | 2D6_1743 |
| | | 2D6_1757 |
| | | 2D6_2502 |
| | | 2D6_2576 |
| | | 2D6_2593 |
| | | 2D6_2603 |
| | | 2D6_2616 |
| | | 2D6_2642 |
| | | 2D6_2658 |
| | | 2D6_3278 |
| | | 2D6_3280 |
| | | 2D6_3323 |
| | | 2D6_3326 |
| | | 2D6_3343 |
| | | 2D6_3368 |
| | | 2D6_3377 |
| | | 2D6_3465 |
| | | 2D6_3477 |
| | | 2D6_3488 |
| | | 2D6_3562 |
| | | 2D6_3592 |
| | | 2D6_3595 |
| | | 2D6_3597 |
| | | 2D6_3598 |
| | | 2D6_4089 |
| | | 2D6_4099 |
| | | 2D6_4102 |
| | | 2D6_4168 |
| | | 2D6_4194 |
| | | 2D6_4206 |
| | | 2D6_4232 |
| | | 2D6_4469 |
| | | 2D6_4472 |
| | | 2D6_4554 |
| | | 2D6_4557 |
| | | 2D6_4558 |
| | | 2D6_4802 |
| | | 2D6_4817 |
| | | 2D6_4896 |
| | | 2D6_4907 |
| | | 2D6_5447 |
| | | 2D6_5472 |
| | | 2D6_5496 |
| | | 2D6_5506 |
| | | 2D6_5661 |
| | | 2D6_5734 |
| | | 2D6_5799 |

FIG._10B

The Codelink™ SNP Bioarray for Human Cytochrome P450 Genes
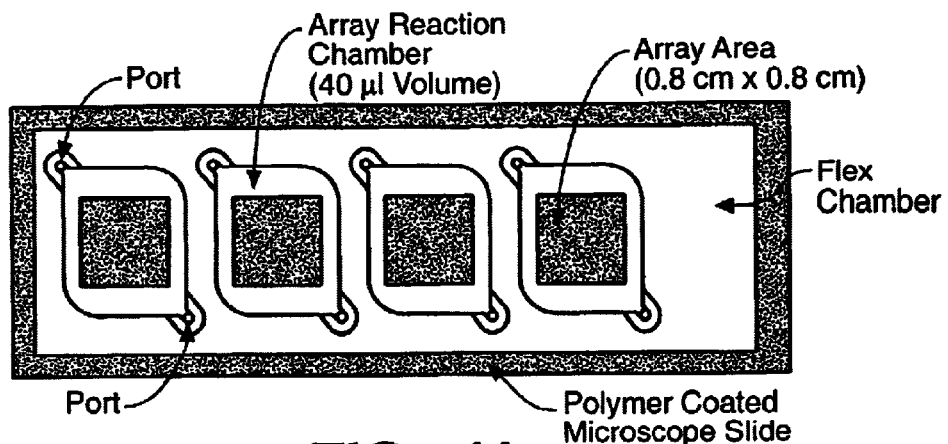
FIG._11
Layout of Primer Pairs in Primer Plates
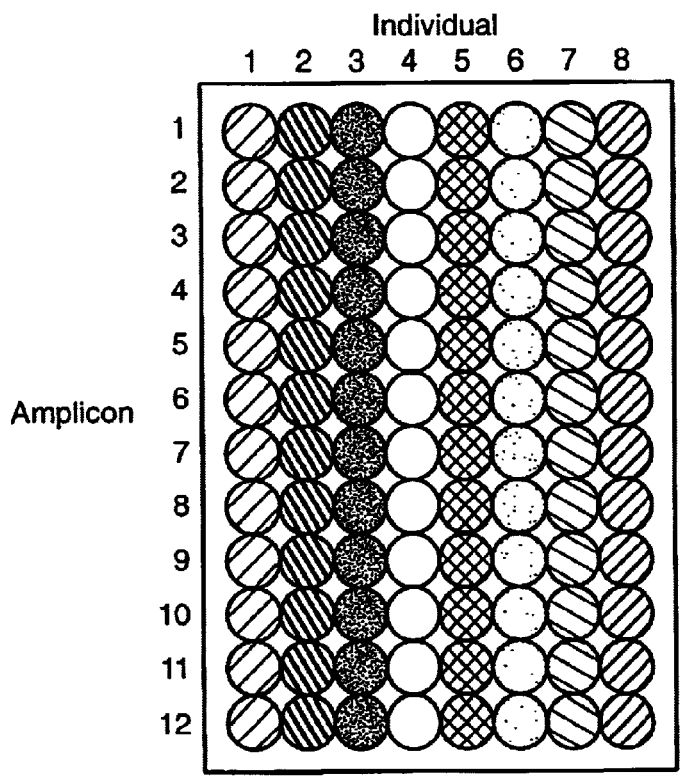
NOTE: Each sample individual will be aliquoted across 12 separate PCR reactions.
FIG._12

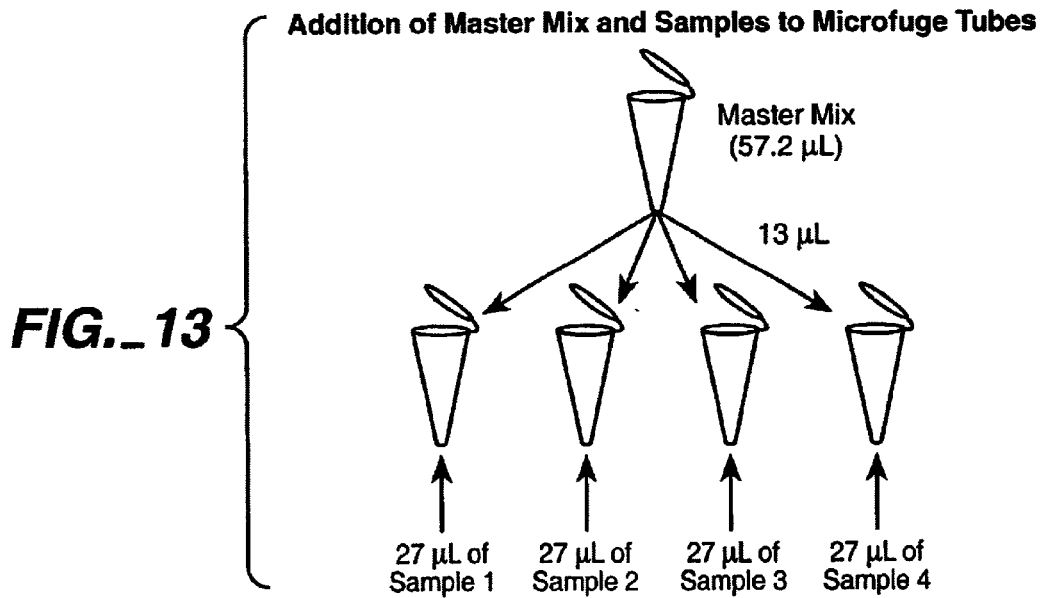
FIG._13
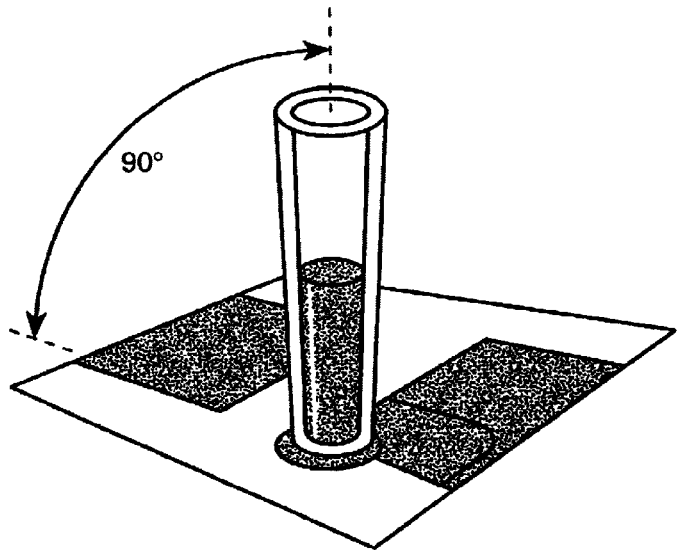
FIG._14
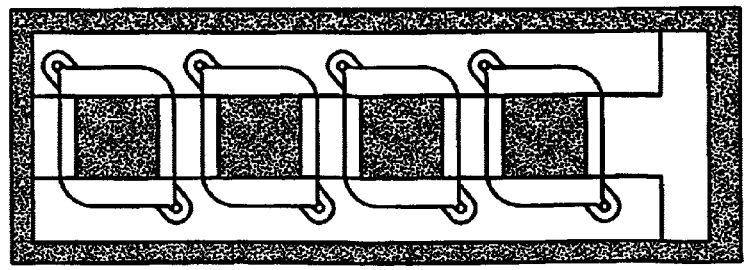
FIG._15

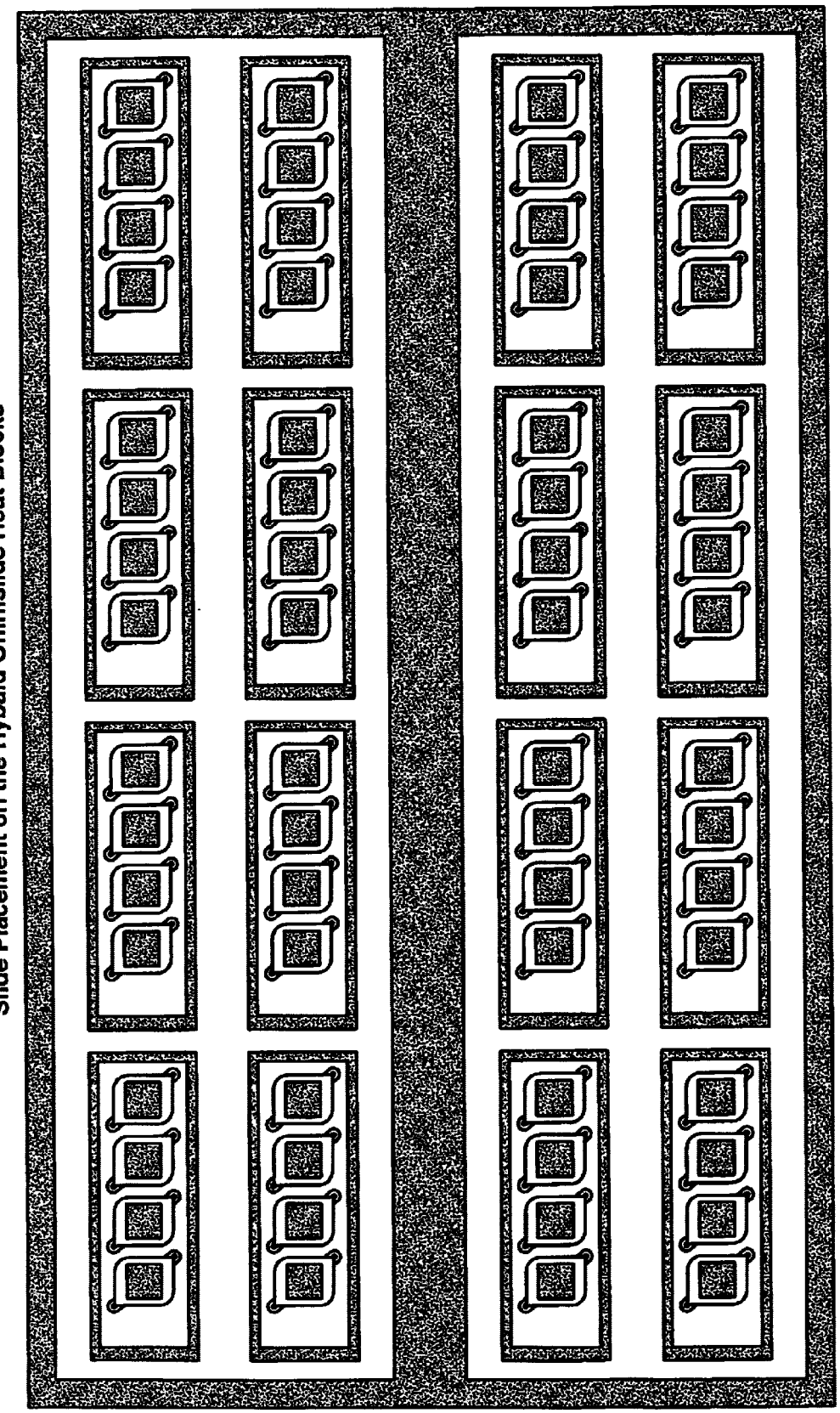
FIG._16

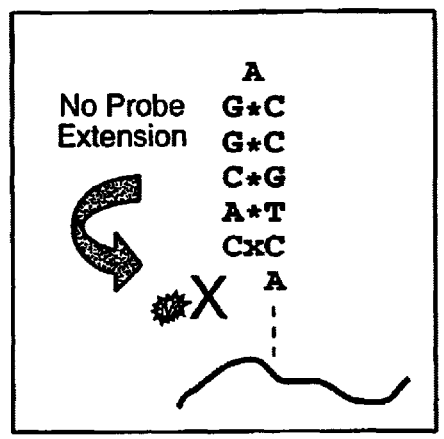
FIG._17
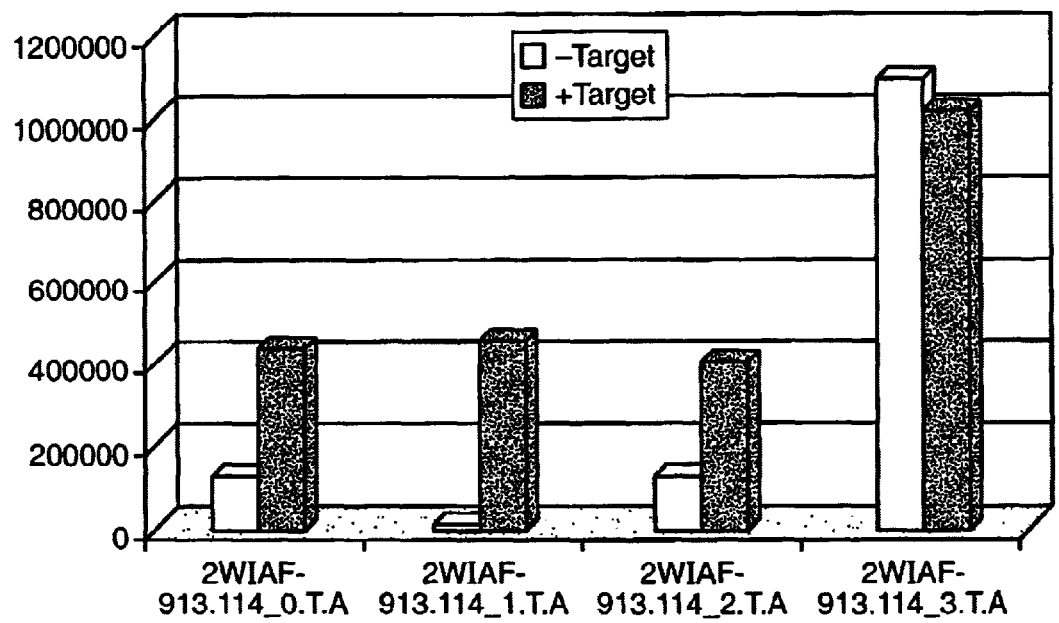
FIG._19

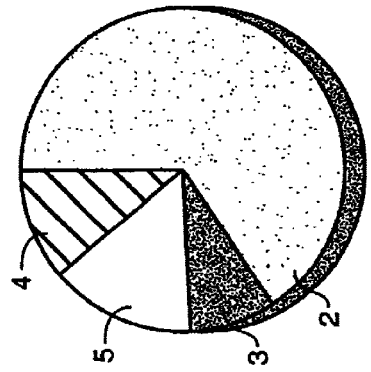

| Target-Independent Signal Strength | Probe | Probe Sequence (5' to 3') | Length / #GC | Predicted Stem-loop | Predicted Base Extended | Observed Base Extended |
|---|---|---|---|---|---|---|
| strong | 50APOE321.T.A | TACACTGCCAGGCA | 14/8 | <u>TGCCAGGCA</u> | G | G |
| strong | 60WIAF913.114.T.A | TCTCTGTCTGTCTCTTGGCA | 20/10 | <u>TGTCTGTCTCTTGGCA</u> | G | G |
| strong | 60POMCC7111G.111.C.A | AAGTGCTCCATGGAGTAGGAG | 21/11 | <u>CTCC</u>(8)<u>GGAC</u> | C | C |
| strong | 70POMCC7111G.111.C.S | CGCGAGGGCAAGCGC | 15/12 | <u>GCG</u>(8)<u>CGC</u> | G | G |
| strong | 70.LPL2.150.C.A | CCCAGAATGCTCACCAGCCTG | 21/13 | <u>CAGCCTG</u> | G | G |
| strong | 60WIAF266.173.C.S. | GCCAGGCAATTTATTTGC | 19/8 | <u>GCAA</u>(6)<u>TTGC</u> | C | C |
| strong | APOE182.A.A | CAGGCGGCCGCT | 12/10 | <u>GGGCGGCCGCT</u> | T | G>C |

Table: Examples of probe sequences that show a strong target-independent signal in the SBE assay. The predicted stem-loop region is underlined.

FIG._18

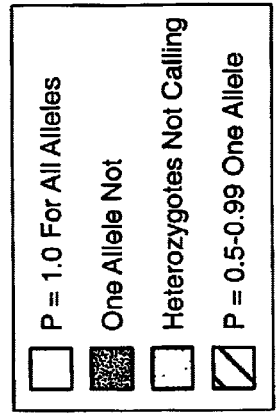

- ☐ P = 1.0 For All Alleles
- ▓ One Allele Not
- ☐ Heterozygotes Not Calling
- ▨ P = 0.5-0.99 One Allele

FIG._20

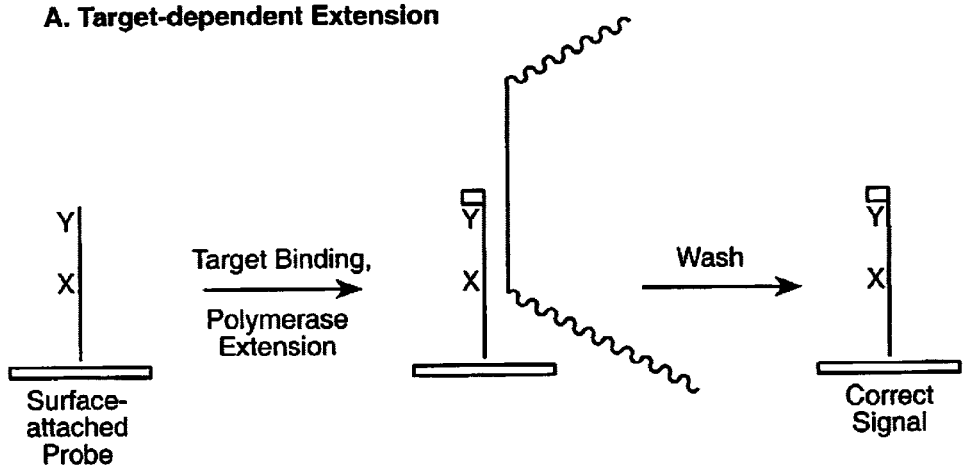
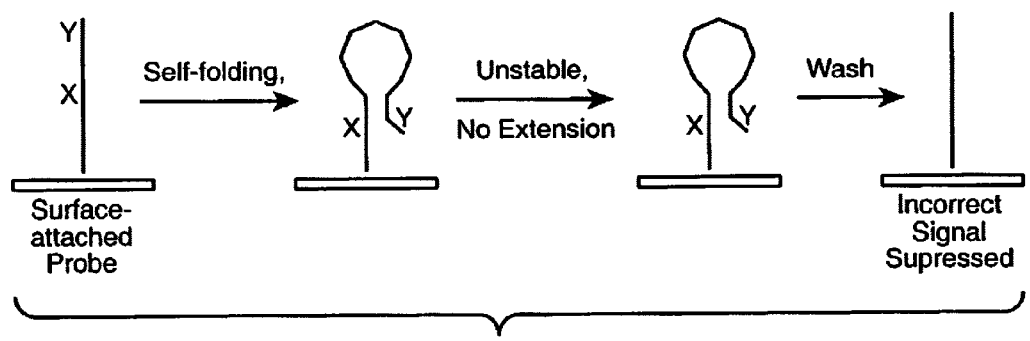
FIG._21

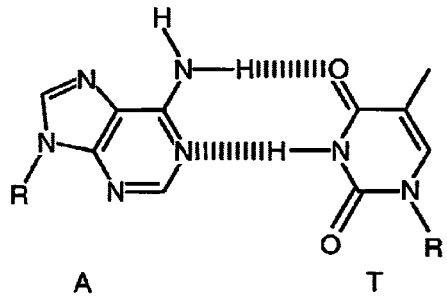

Natural A:T base pair, pairs equally well with target and itself

FIG._22A

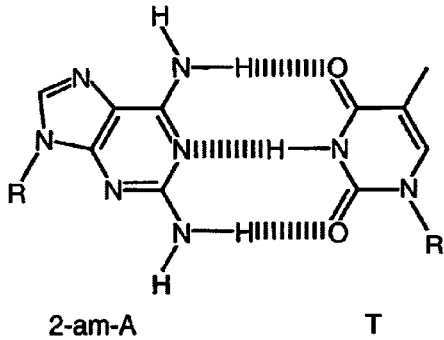

2-am-A:T base pair, (target-probe pair) forms a very stable base-pair

FIG._22C

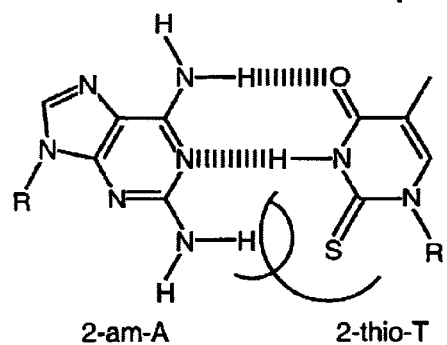

Non-natural 2-am-A:2-thioT base-pair, does not form a stable base-pair

FIG._22B

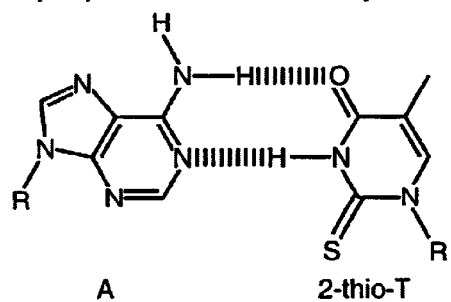

A:2-thio-T base pair, (target-probe pair) forms a stable base-pair

FIG._22D

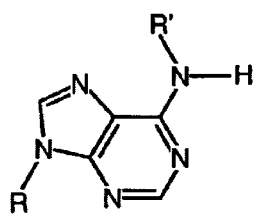

Exo-cyclic amine modified A

Modified A

FIG._23A

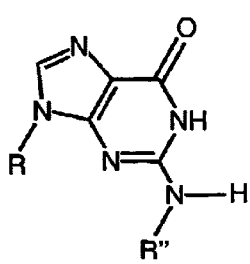

Exo-cyclic amine modified G

Modified G

FIG._23B

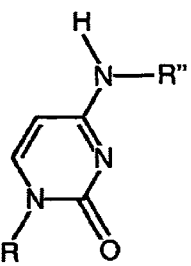

Exo-cyclic amine modified C

Modified C

FIG._23C

A. Target-dependent Extension
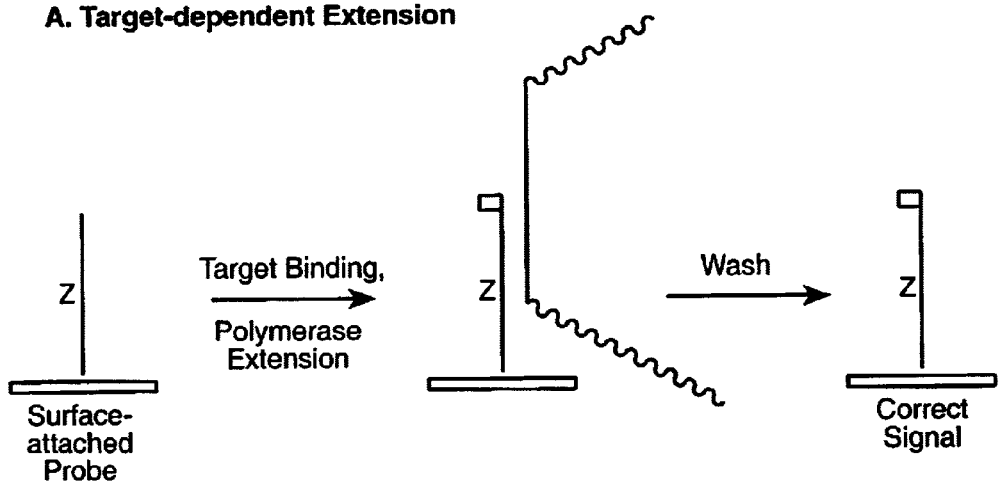
B. Target-independent Extension
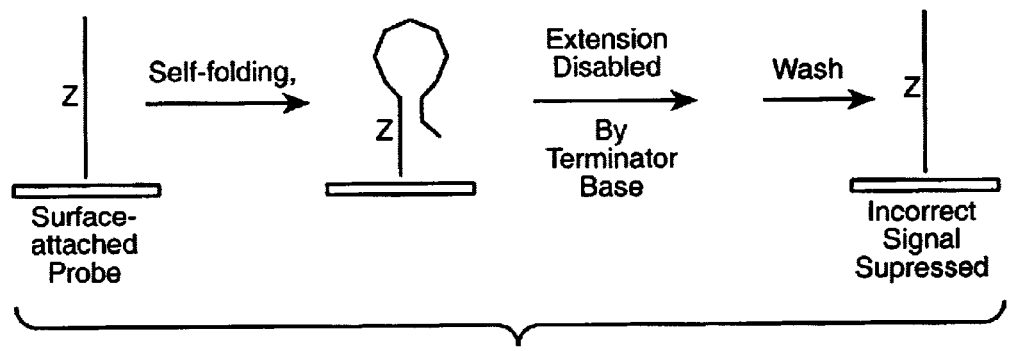
FIG._24
"Terminator" Base
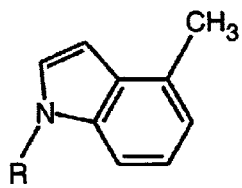
4-methyl-indole
FIG._25A
"Terminator" Nucleoside
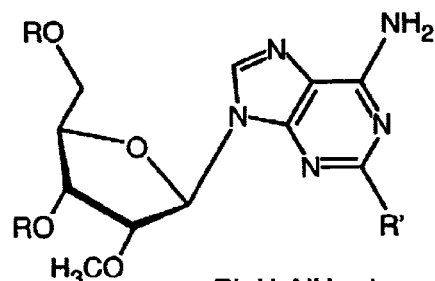
R'=H, $NH_2$ etc.
2'-O-methyl-2-amino-A
FIG._25B Table: List of modified bases / nucleosides used, Q = abasic nucleotide: no base-pairing ability, no stacking energy; placed immediately downstream of putative stem-loop; expect A to be incorporated when Q is in template (the "A rule").

I = 4-methylindole: A analog; placed immediately downstream of putative stem-loop; terminates DNA polymerase activity.

K = 5-nitroindole: universal base; placed immediately downstream of putative stem-loop; does not form base pairs but contributes stacking energy.

Z = 2-amino-A: placed within the stem of putative stem-loop; forms 3 hydrogen-bonds with T; no base pairing with 2-thio-dT.

X = 2-thio-dT: placed with stem of putative stem-loop; stable base pairs with A; no base pairing with 2-amino-A.

*FIG._26*

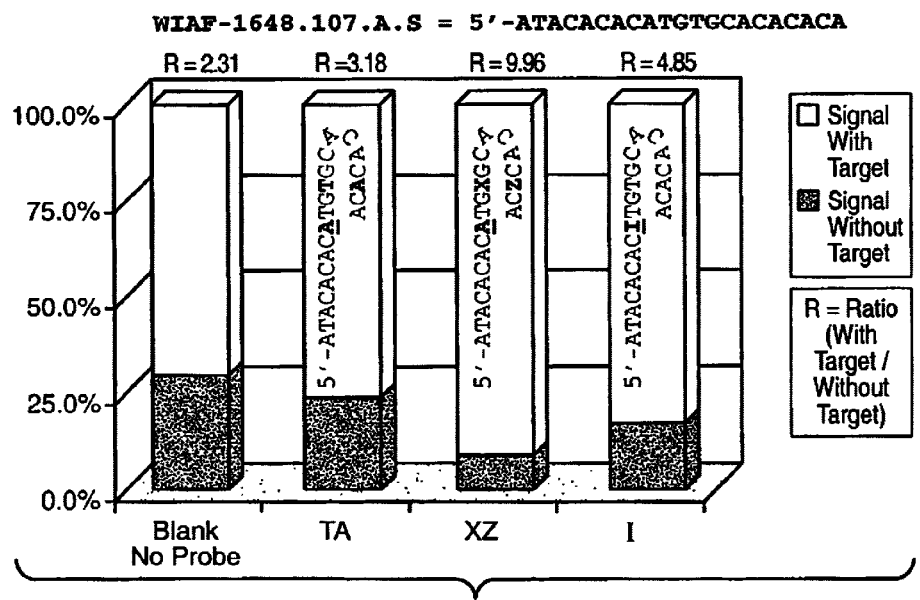

*FIG._27*

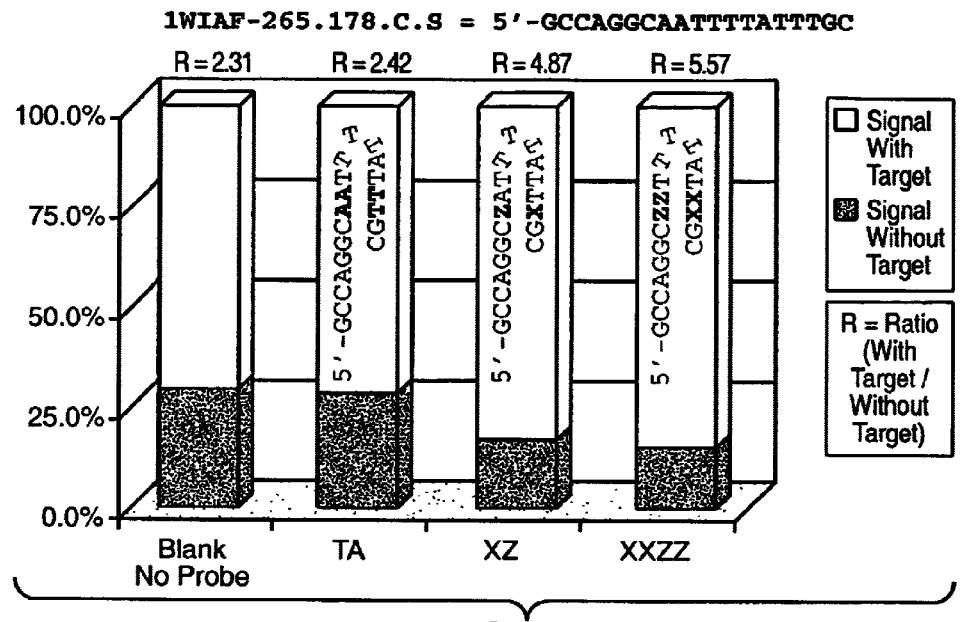
FIG._28
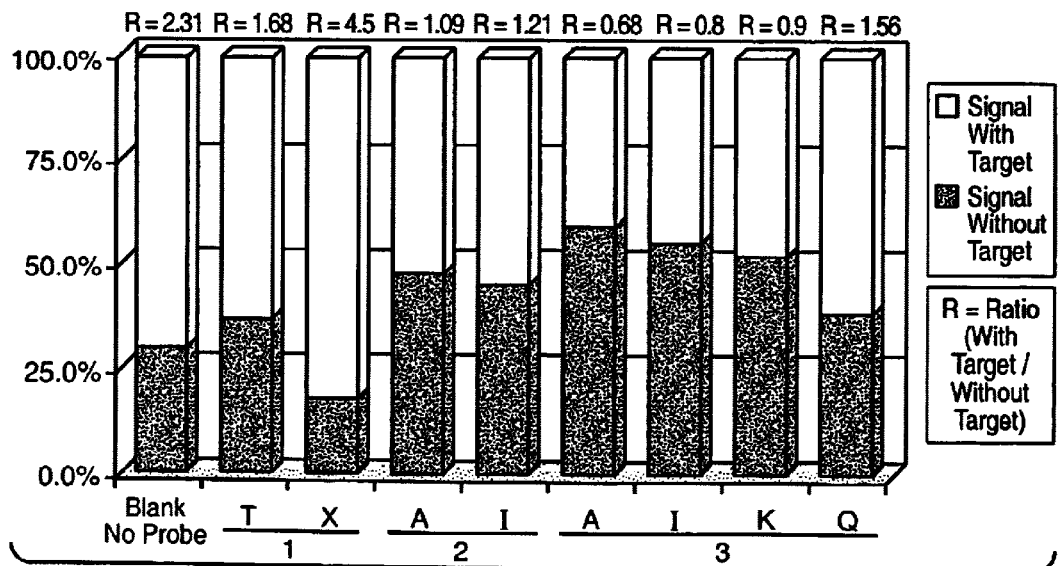
FIG._29

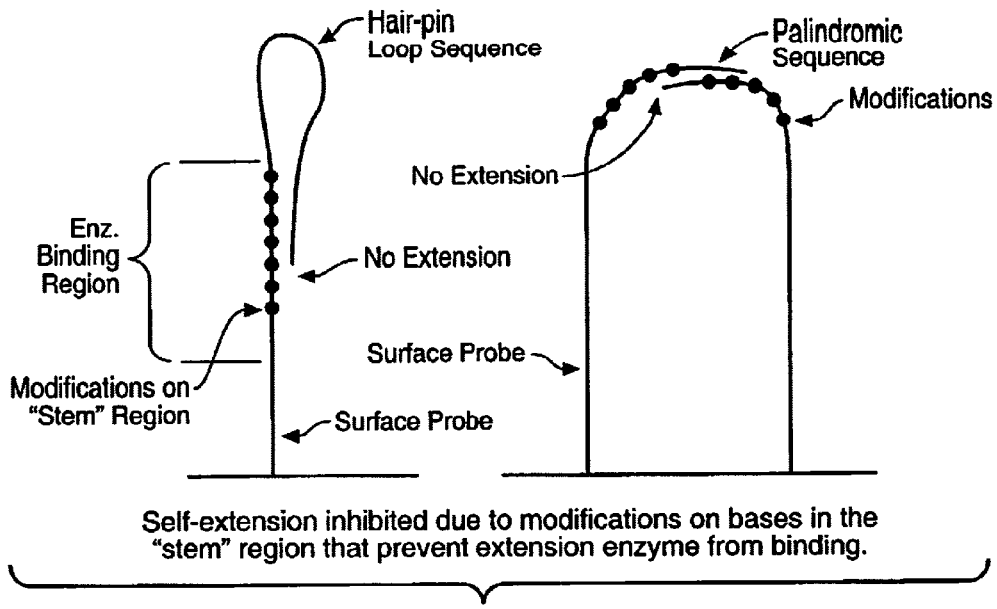
Self-extension inhibited due to modifications on bases in the "stem" region that prevent extension enzyme from binding.
FIG._30
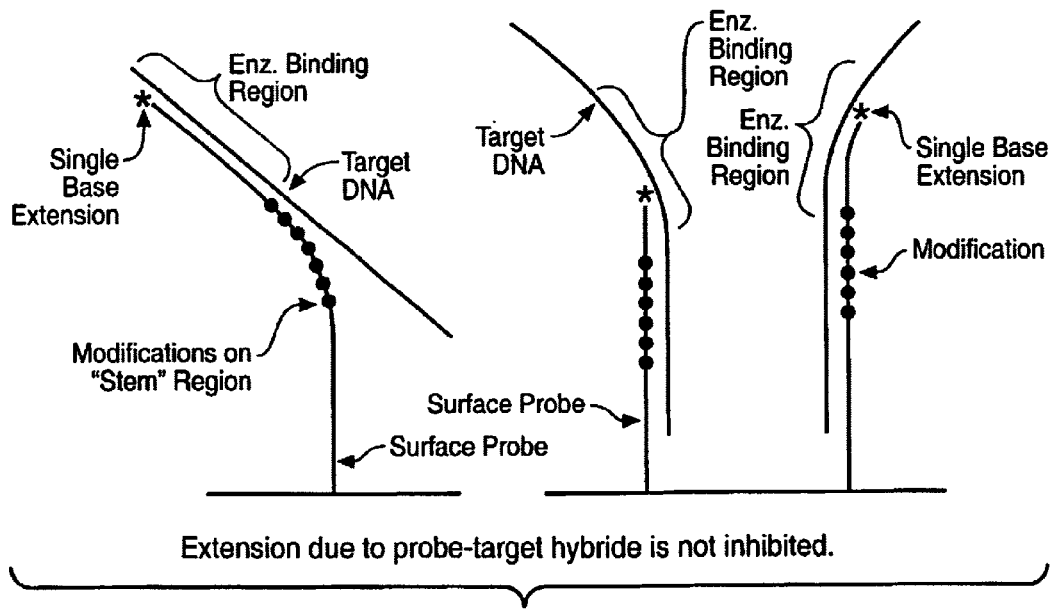
Extension due to probe-target hybride is not inhibited.
FIG._31

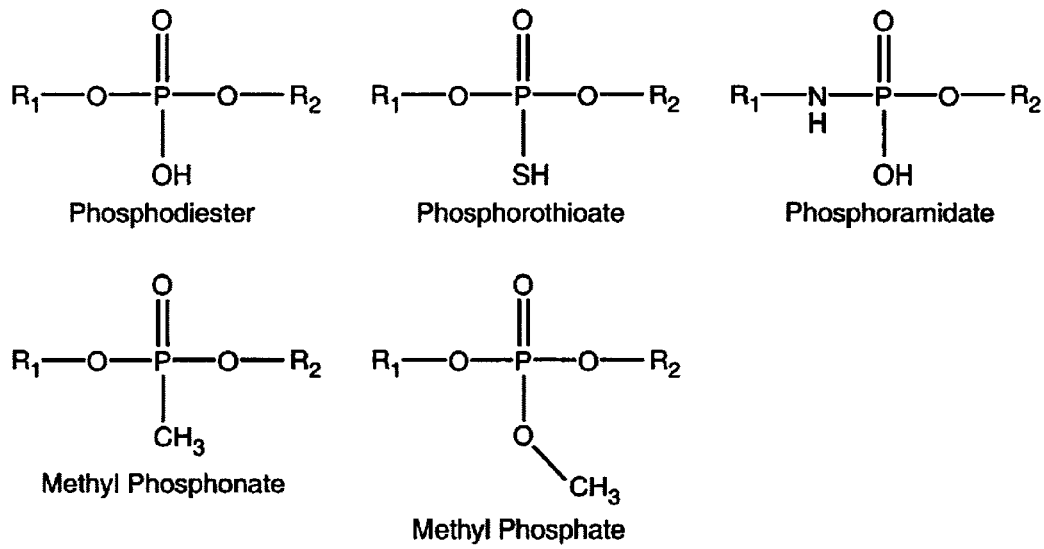
Modified nucleotide bases reduce the binding affinity of the SBE enzyme or extension enzyme.
*FIG._32A*
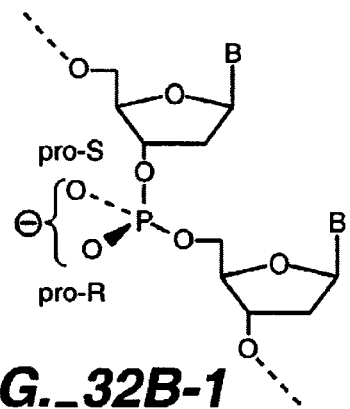
*FIG._32B-1*
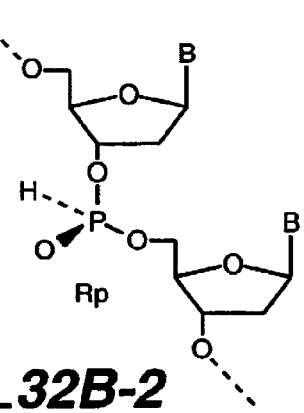
*FIG._32B-2*
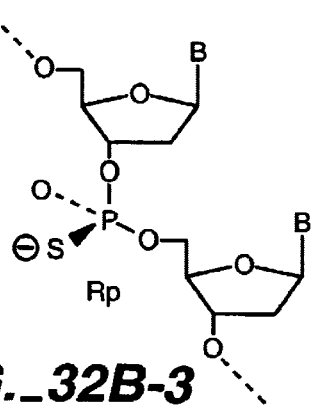
*FIG._32B-3*
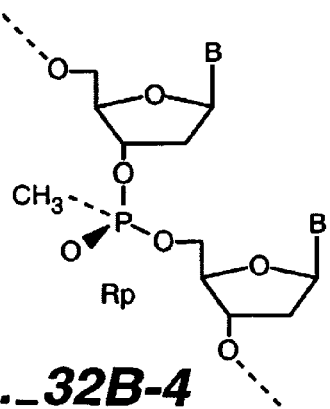
*FIG._32B-4*

Results From an Experiment Using Oligonucleotide Inhibitors to Prevent Self Extension of Probes in the SBE Assay.
FIG._33A
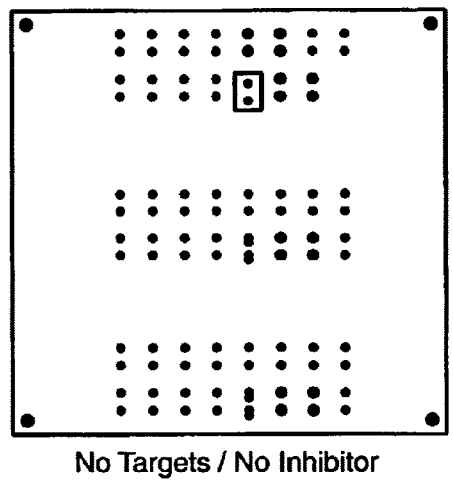
No Targets / No Inhibitor
FIG._33B
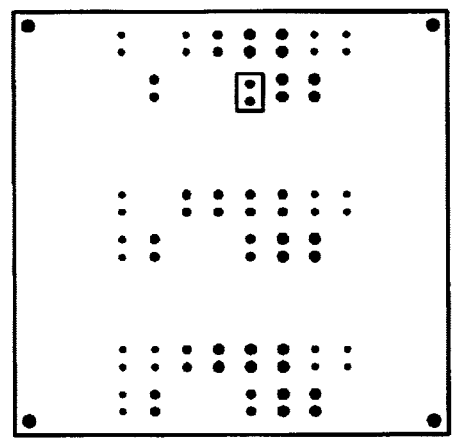
cRNA Targets / No Inhibitor
FIG._33C
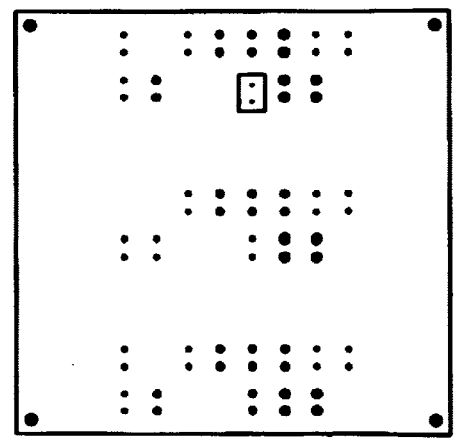
cRNA Targets / Apo E Inhibitor

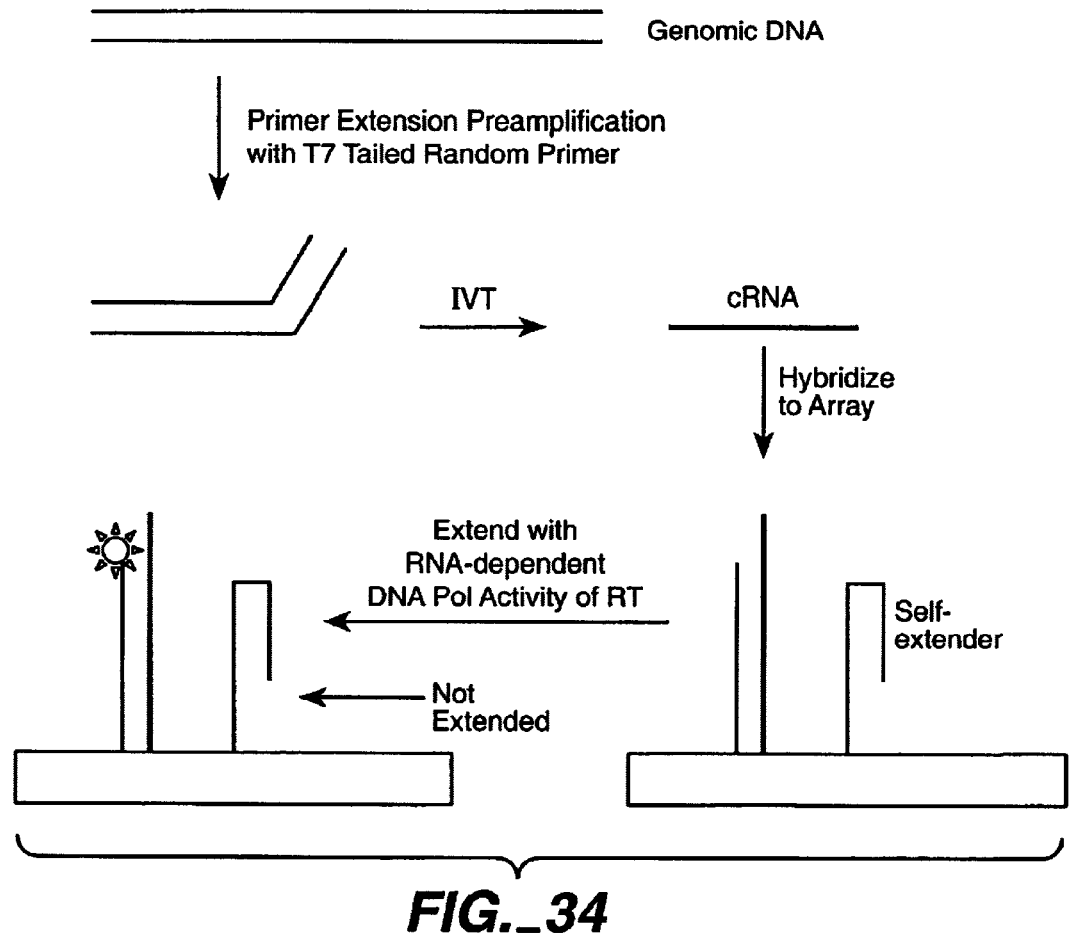
FIG._34

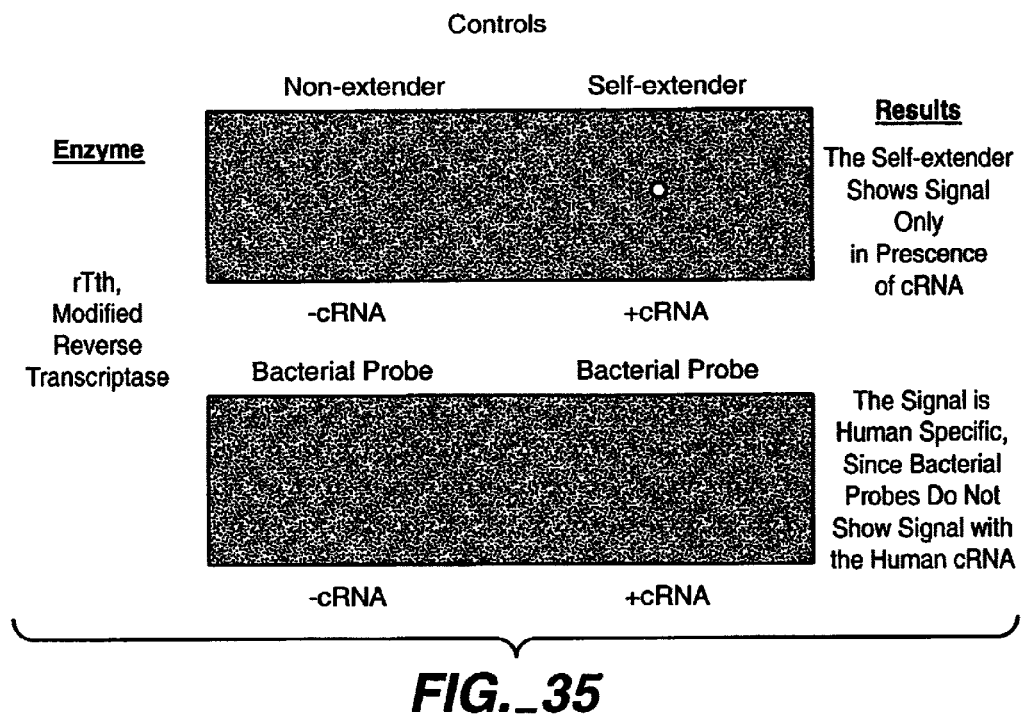
FIG._35
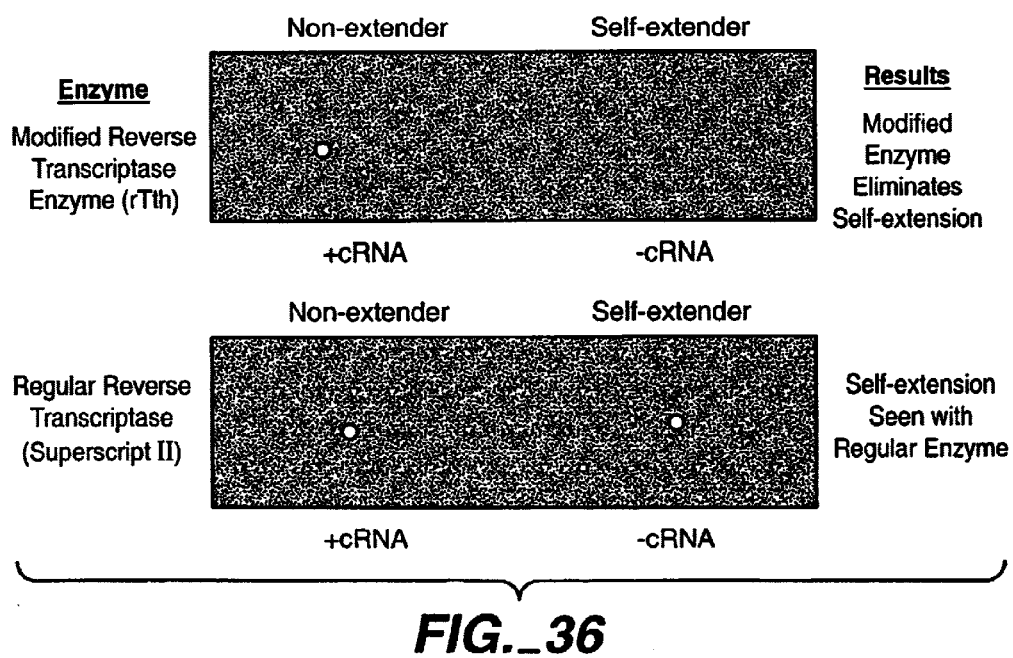
FIG._36

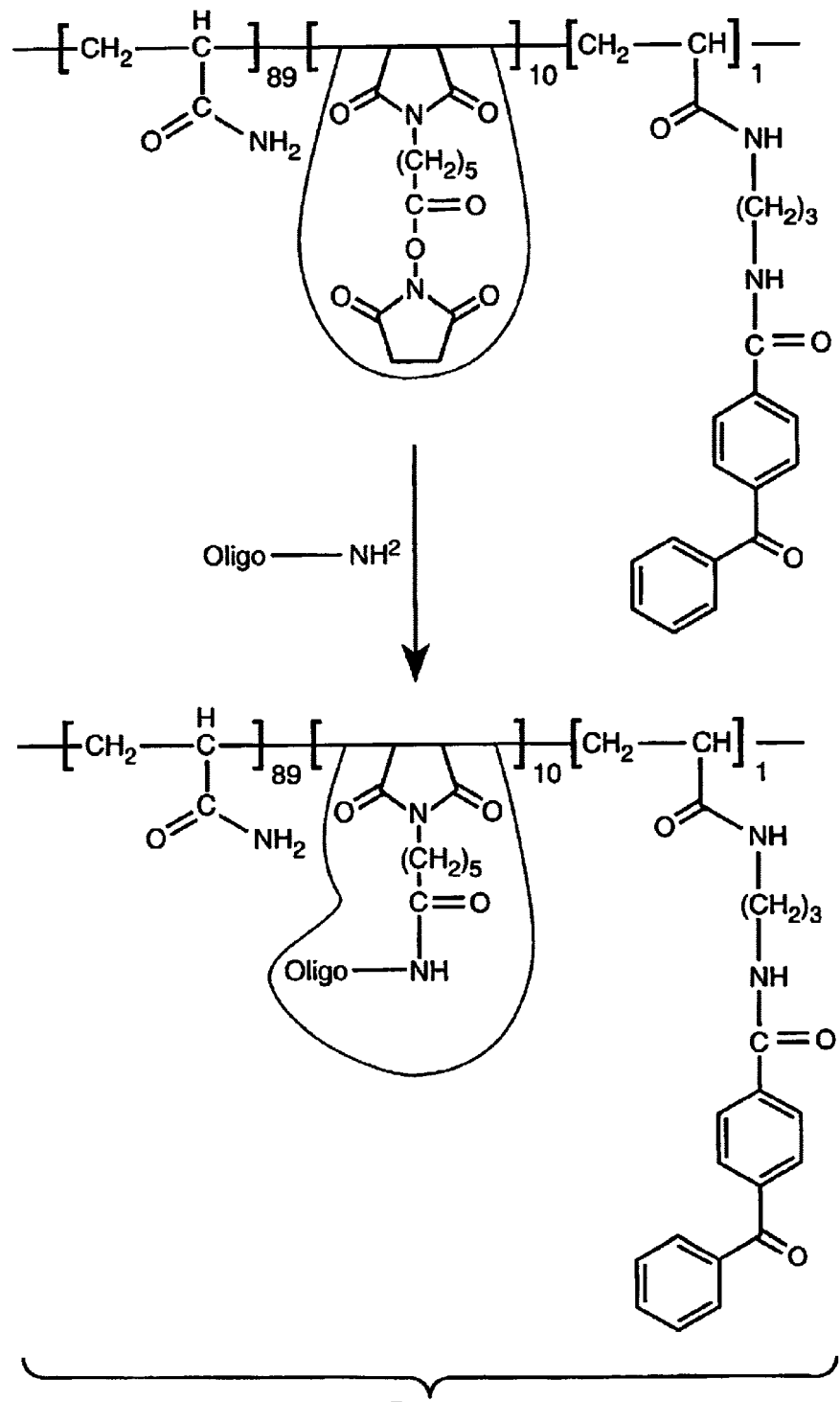
Reaction of Amino Oligonucleotides on the SurModics Surface
(An Example of Acyl Substitution Reaction on the Polymer Backbone)
FIG._37

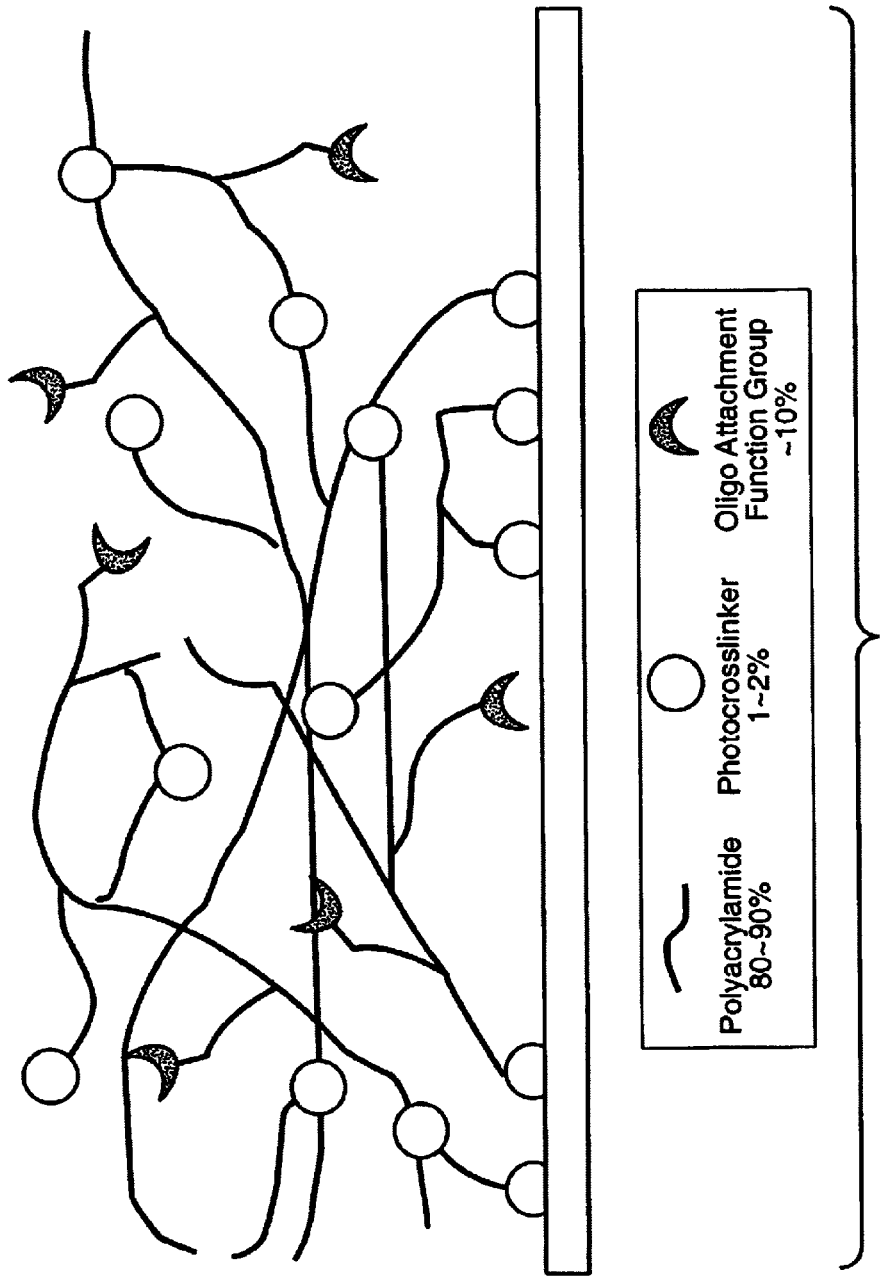

P450 SINGLE NUCLEOTIDE POLYMORPHISM BIOCHIP ANALYSIS

This application claims the benefit of Provisional Application No. 60/280,583 filed Mar. 30, 2001.

FIELD OF THE INVENTION

The invention is generally directed to novel methods and compositions for the determination of single nucleotide polymorphisms (SNPs) in P450 genes using novel probes and methods that improve the specificity and efficiency of P450 SNP detection. This invention provides a unique collection of P450 SNP probes on one assay which can be performed on a variety of array platforms, the primer sequences for specific amplification of each of the seven P450 genes and amplicon control probes to evaluate whether the intended p450 gene targets were amplified successfully.

BACKGROUND OF THE INVENTION

The basic purpose of drug metabolism in the body is to make drugs more water soluble and thus more readily excreted in the urine or bile. One common way of metabolizing drugs involves the alteration of functional groups on the parent molecule (e.g. oxidation), via the cytochrome P450 enzymes. These enzymes are predominantly found in the liver. Cytochrome p450 enzymes are involved in numerous drug metabolism pathways as well as pathways used to make cholesterol, steroids, and other important lipids such as prostacyclins and thromboxane A2. Many drug interactions are a result of inhibition or induction of cytochrome P450 enzymes.

Mammalian cytochrome P450 genes encode a superfamily of hemeproteins that are active in the oxidative metabolism of endogenous and exogenous compounds. Cytochrome P450 (referred to as CYP) are now classified into families on the basis of amino acid similarity; within families cytochrome P450 exhibit >40% similarity and >55% similarity within subfamilies. The cytochrome P450 enzymes are designated by the letters "CYP" followed by a numeral, a letter and another numeral (e.g. CYP2D6). In humans there are more than 20 different CYP enzymes. According to a recent compilation, the cytochrome P450 2C subfamily contains 36 distinct genes and pseudogenes, and is the largest cytochrome P450 subfamily that has been identified to date. It is generally accepted that mammalian cytochrome P450 genes are regulated primarily at the level of transcription, and there is little information known on the factors that regulate transcription.

There are a wide variety of polymorphisms (e.g. mutations) in p450 enzymes, and many of these polymorphisms result in (or are associated with) the inhibition or induction of enzymatic activity. These polymorphisms frequently occur in ethnic populations. The cytochrome P450 genes that have been studied most intensively in this regard are cytochrome P450 2D6, the debrisoquine hydroxylase gene, and cytochrome P450 2C19, which codes for the S-mephenyloin hydroxylase. A variety of other P450 enzymes exhibit variation in expression levels; for example, cytochrome P450 3A4, the major cytochrome P450 present in human liver, varies over a several-fold range at both the protein and mRNA levels. In addition, many of the P450 enzymes are subject to induction by different drugs, including barbiturates, antibiotics, etc.

Of particular interest to the present invention are CYP1A1, CYP1A2, CYP1B1, CYP2C19, CYP3D6, CYP2E1 and CYP3A4. CYP2D6 has been studied extensively because it exhibits significant diversity, with roughly 7 to 10 percent of Caucasians being poor metabolizers of drugs metabolized by CYP2D6. Patients with normal CYP2D6 activity are termed extensive metabolizers, with Asians and African Americans being less likely than Caucasians to be poor metabolizers. Poor metabolizers are at risk for drug accumulation and toxicity from drugs metabolized by this enzyme. While only 2 to 6 percent of total liver cytochrome P450 is CYP2D6, nearly 25 percent of clinically useful medications are metabolized by this enzyme. Poor metabolizers of CYP2D6 substrates are at risk for increased toxicity from medications that are metabolized by CYP2D6. Conversely, when formation of an active metabolite is essential for drug action, poor metabolizers of CYP2D6 can exhibit less response to drug therapy compared with extensive metabolizers. About 15 percent of clinically used medications are metabolized by CYP1A2, and it is the only CYP that is induced by tobacco and other polycyclic aromatic hydrocarbons.

CYP2E1 metabolizes a relatively small fraction of medications (although it has a significant role in the metabolism of acetaminophen), it plays a significant role in activation and inactivation of toxins. It is inducible by ethanol and metabolized primarily small organic molecules.

Members of the CYP3A family are the most abundant and most clinically significant cytochrome enzymes in humans, with CYP3A4 being the most common form and the most widely implicated in most drug interactions. The CYP3A family is located in the small intestine and in addition to drug, is also responsible for metabolizing most of the body's endogenous steroids.

CYP2C19, along with CYP2D6, also exhibits genetic polymorphism, with 3 percent of Caucasians and 20 percent of Japanese lacking the enzyme completely. These individuals are at risk for more frequent and more severe adverse effects because of decreased elimination of drugs metabolized by CYP2C19.

Thus, detection of specific P450 SNPs is important in diagnostic medicine and molecular biology research and also, to understand the mechanism of action of many drugs and are likely to be the direct cause of therapeutically relevant phenotypic variants and/or disease predispositions.

Accurate SNP detection requires good sensitivity in the SBE assays. Two major hurdles for highly parallel screening of SNPs on microarrays are: 1) the necessity to amplify DNA regions spanning the SNPs by PCR to achieve sufficient sensitivity and specificity of detecting a single-base variation in the complex human genome in a reproducible way; and, 2) the ability to distinguish unequivocally between homozygous and heterozygous allelic variants in the diploid human genome. Differential hybridization with allele-specific oligonucleotide (ASO) probes is most commonly used in the microarray format (Pastinen et al., Genome Research 2000). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes, as defined in greater detail below, include, but are not limited to, OLA, RCA, Invader™, single base extension (SBE) methods, allelic PCR, and competitive probe analysis. In SBE assays, a polynucleotide probe is attached to a support and hybridized to target DNA.

Generally, for SBE assays, probe sets are designed such that the nucleotide at the 3' end of the probe is either matched or mismatched with the queried base in the target. If the base matches and hybridizes, the DNA polymerase will extend the probe by one base in the presence of four labeled-terminator nucleotides. Alternately, if the 3' base is mismatched, the DNA polymerase does not extend the probe. Thus, the identity of the SNP or queried base in the target is determined by the probe set that is extended by the DNA polymerase.

Some probes form internal stem-loop structures resulting in target-independent self-extension of the probe thus giving a false positive signal that interferes with determination of the SNP base. The present invention aims to overcome such problems.

Accordingly, it is an object of the present invention to provide compositions and methods for evaluating samples from one or more patients, to ascertain the level and/or genotype of various P450 enzymes present. Another object of the present invention is to increase the sensitivity and specificity of the P450 SBE assays. The present invention uses a combination of amplification methods, and, a variety of methods to prevent self-extension of capture probes in the absence of target thereby reducing the occurrence of false positive results.

SUMMARY OF THE INVENTION

In accordance with the objects outlined above the present invention provides a biochip comprising a solid substrate comprising an array comprising at least one capture probe substantially homologous to a portion of the sense strand of a nucleic acid encoding CPY1A1, at least one capture probe substantially homologous to a first portion of the sense strand of a nucleic acid encoding CPY1A2, at least one capture probe substantially homologous to a first portion of the sense strand of a nucleic acid encoding CPY1B1, at least one capture probe substantially homologous to a first portion of the sense strand of a nucleic acid encoding CPY2C19, at least one capture probe substantially homologous to a first portion of the sense strand of a nucleic acid encoding CPY2D6, at least one capture probe substantially homologous to a first portion of the sense strand of a nucleic acid encoding CPY2E1, and at least one capture probe substantially homologous to a first portion of the sense strand of a nucleic acid encoding CPY3A4.

In addition, the invention provides a method of determining the identification of a nucleotide at a detection position in at least one target sequence selected from the group consisting of CYP1A1, CYP1A2, CYP1B1, CYP2C19, CYP2D6, CYP2E1 and CYP3A4, the method including providing an array comprising at least one first capture probe substantially homologous to a first portion of a nucleic acid encoding CPY1A1, wherein the first capture probe is directly adjacent to or includes at its terminus a detection position, at least one second capture probe substantially homologous to a first portion of the sense strand of a nucleic acid encoding CPY1A2, wherein the second capture probe is directly adjacent to or includes at its terminus a detection position, at least one third capture probe substantially homologous to a first portion of the sense strand of a nucleic acid encoding CPY1B1, wherein the third capture probe is directly adjacent to or includes at its terminus a detection position, at least one fourth capture probe substantially homologous to a first portion of the sense strand of a nucleic acid encoding CPY2C19, wherein the fourth capture probe is directly adjacent to or includes at its terminus a detection position, at least one fifth capture probe substantially homologous to a first portion of the sense strand of a nucleic acid encoding CPY2D6, wherein the fifth capture probe is directly adjacent to or includes at its terminus a detection position, at least one sixth capture probe substantially homologous to a first portion of the sense strand of a nucleic acid encoding CPY2E1, wherein the sixth capture probe is directly adjacent to or includes at its terminus a detection position, and at least one seventh capture probe substantially homologous to a first portion of the sense strand of a nucleic acid encoding CPY3A4, wherein the seventh capture probe is directly adjacent to or includes at its terminus a detection position. The method further includes hybridizing at least one target sequence to its corresponding capture probe to form a hybridization complex, adding a polymerase and at least one dNTP comprising a label, under conditions whereby if the dNTP is perfectly complementary to a detection position, the dNTP is added to a capture probe to form an extended probe, determining the nucleotide at the interrogation position of said extended probe.

In addition the invention provides a method of determining the identification of a nucleotide at a detection position in a target sequence. The method includes providing an array that includes a solid support with a first surface comprising a hydrogel layer comprising an array of capture probes, hybridizing the target sequence to at least one of the capture probes to form a hybridization complex and determining the nucleotide at the detection position.

In addition the invention provides a method of determining the identification of a nucleotide at a detection position in a target sequence. The method includes providing a solid support with a first surface comprising at least one extension probe that has been modified to form a non-self extension probe, such that self extension of the non-self extension probe does not occur in the absence of the target and wherein, the non-self extension probe includes an interrogation nucleotide, hybridizing the target sequence to the non-self extension probe to form a hybridization complex, contacting the surface with an extension enzyme and at least one chain terminating nucleotide comprising a hapten under conditions whereby if the chain terminating nucleotide is perfectly complementary to the base of the target sequence immediately adjacent to the 3' end of the non-self extension probe in the hybridization complex, the chain terminating nucleotide is added to the non-self extension probe to form a modified extension probe. In addition the method includes contacting the modified extension probe with the binding partner of the hapten, wherein the binding partner is labeled and detecting the presence of the label to determine the nucleotide at the detection position.

In addition the invention includes a method of determining the identification of a nucleotide at a detection position in a target sequence comprising amplifying the target DNA using random primers to generate DNA amplicons, transcribing the DNA amplicons to generate RNA target sequences (in vitro transcription), providing a solid support with a first surface comprising at least one extension probe wherein the extension probe includes an interrogation nucleotide, hybridizing the RNA target sequence to the extension probe to form a hybridization complex, contacting the surface with a modified reverse transcriptase and at least one chain terminating nucleotide comprising a hapten under conditions whereby if the chain terminating nucleotide is perfectly complementary to the base of the target sequence immediately adjacent to the 3' end of the redesigned extension probe in the hybridization complex, the chain terminating nucleotide is added to the redesigned extension probe to form a modified extension probe contacting the modified extension probe with the binding partner of the hapten, wherein the binding partner is labeled and detecting the presence of the label to determine the nucleotide at the detection position.

In addition the invention provides a method of determining the identification of a nucleotide at a detection position in a target sequence comprising providing a solid support with a first surface comprising a solid support with a first surface comprising a hydrogel layer comprising at least one extension probe, wherein the extension probe includes an interrogation nucleotide within two bases of the 3' end of the extension probe, hybridizing the target sequence to the extension probe to form a hybridization complex contacting the surface with an extension enzyme and at least one chain terminating nucleotide comprising a hapten; under conditions whereby if the chain terminating nucleotide is perfectly complementary to the base of the target sequence immediately adjacent to the 3' end of the extension probe in the hybridization complex, the chain terminating nucleotide is added to the extension probe to form a modified extension probe, contacting the modified extension probe with the binding partner of the hapten, wherein the binding partner is labeled and detecting the presence of the label to determine the nucleotide at the detection position.

BRIEF DESCRIPTION OF THE DRAWINGS

FIG. 1 depicts two different configurations of the SBE genotyping reaction. In FIG. 1A, target 5 with detection position 10 is hybridized to capture probe 25, attached to a solid support 15 via an attachment linker 20. The capture probe also serves as the SBE extension probe. FIG. 1B, a first portion of target 5 with detection position 10 is hybridized to capture probe 25, attached to a solid support 15 via an attachment linker 20. A second portion of target 5 is hybridized to an SBE extension primer 30 for a "sandwich type" assay.

FIG. 2A depicts a typical single base extension (SBE) assay. FIG. 2B demonstrates how self-extension of a probe in the absence of target sequence can occur in an SBE reaction due to stem-loop structures formed by the capture probe thus producing a false-positive result.

FIGS. 3A through 3D depict a worksheet describing the P450 polymorphisms (SNPs) and literature references for each of the genes included into our assay design.

FIGS. 3E through 3H is a worksheet describing CYP allele haplotype families.

FIG. 4 depicts a comparison table illustrating the relative homology shared by the genes in the CYP2D6 family. Comparison between corresponding introns and exons is depicted as well as their % similarity.

FIG. 5 (SEQ ID NOS:1–20) depicts the preferred P450 PCR primer list currently being used for amplification. In order to design primers specifically to the target gene of interest, regions were selected with base pair mismatches against subfamily related genes, focusing particularly at the 3' end of the primer. In this manner, the annealing hybridization specificity and the discrimination of the PCR polymerase which extends nucleotides from the 3' end of the primer is relied upon to confer specificity. Primer design was further restricted to a length greater than 19 bp and a balance in terms of GC content and Tm per pair. All primer candidates have been analyzed using the BLAST algorithm (homology analysis algorithm) against a compiled P450 sequence library (57 genes) to remove any potential cross-reactive primer candidates. In addition to homology analysis, the primer candidates were also screened against a database of repetitive sequences.

FIGS. 6A through 6E depict the final P450 probe list on the chip for the current P450 assay.

FIG. 7 depicts a summary of the Beta Validation Performance data and the discrimination capabilities of these probes.

FIGS. 8A through 8F depict the probes designed to identify a particular SNP.

FIGS. 9A and 9B depict the relationship of the CYP genes.

FIGS. 10A and 10B summarize the product amplicon characteristics.

FIG. 11. The Codelink™ SNP Bioarray for human cytochrome P450 genes.

FIG. 12. Layout of primer pairs in primer plates.

FIG. 13. Addition of master mix and samples to microfuge tubes.

FIG. 14. Tip orientation for loading reaction mixtures into chambers.

FIG. 15. Orientation of sealing strips over chamber ports.

FIG. 16. Slide placement on the Hybaid Omnislide heat blocks.

FIG. 17. Prevention of self-extension due to base additions. Increasing the length of the probe by one or more bases at the 3' end of the probe creates a mismatch at the end of the stem-loop structure. DNA polymerase will not extend the probe when the 3' end is mismatched ad hence, there is no self-extension.

FIG. 18. (SEQ ID NOS:251–257) shows examples of probe sequences that show strong target-independent self extension in the SBE assay. The predicted stem-loop is underlined.

FIG. 19. None, one, two or three bases were added to the end of the 2WIAF-913.114.T.A. probe. The addition of one base reduced the self-extension signal but did not reduce target-dependent signal; this probe is 'repaired' and will call the SNP base correctly. The addition of two or three additional bases created new stem-loop structures that resulted in self-extension. The frequency at which additional bases create new self-extenders varies with probe sequence. The sequences of the probes are:
2WIAF-913.114_O.T.A.; TCTCTGTCTGTTCCTTGGCA (SEQ ID NO:252). 2WIAF-913.114_1.T.A.; TCTCTGTCTGTCTCTTGGCAC (SEQ ID NO:258), 2WIAF-913.114_2.T.A.;

TCTCTGTCTGTCTCTTGGCACA (SEQ ID NO:259), 2WIAF-913.114_3.T.A.;
TCTCTGTCTGTCTCTTGGCACAG (SEQ ID NO:260).

The putative stem-loop structures are shown in underlined. Note the mismatched 3' base of 2WIAF-913.114_.1.T.A.

FIG. 20. Results from the attempted redesign of 35 probes for the P450 gene family. For 35 probe sets that called the SNP base incorrectly, 23 (66%) the SNP base called correctly 100% of the time when one or two bases were added to the 3' end of the self-extending probe. P is the product of call rate and accuracy; P=1 indicates that the probe set calls the SNP base correctly 100% of the time.

FIG. 21(A) depicts target-dependent extension by incorporating labeled nucleotides corresponding to the complementary base in the target sequence. X and Y are the modified bases which have minimal effect on the target-dependent signal generation, as their base-pairing abilities with the natural bases are unaffected (B) The modified base-pair X, Y effectively suppresses the target-independent extension as they cannot form a stable base-pair with each other. Due to lack of stability, no extension occurs and false positive signals are suppressed in the SBE assay.

FIGS. 22A through 22D depict natural and modified nucleic acids that are used to synthesize novel probes used in preferred embodiments of this invention. This base-pair effectively suppresses the target-independent extension, as they cannot form a stable base-pair with each other as it thermodynamically destabilizes the self-folded product.

FIGS. 23A through 23C depict exemplary structures of some exo-cyclic amine modified bases A, C and G.

FIG. 24. A modified "terminator-type base". In (A) the modified "terminator-type base" Z is able to bind target nucleic acid and to be extended in an SBE assay. But in (B) the modified "terminator-type base" Z prevents DNA polymerases from extending past the modified base position. Thus, only target-dependent probe-extension takes place and the target-independent extension is suppressed.

FIGS. 25A and 25B depict exemplary structures of an extension "terminator" base and nucleoside.

FIG. 26. List of modified bases/nucleosides used in FIGS. 27–29.

FIG. 27. (SEQ ID NOS:261–263) Graphs of experiments demonstrating the effectiveness of use of probes with modified nucleic acids. In this experiment, probe sequence 5'-ATACACACATGTGCACACACA (SEQ ID NO:261) was used. This shows that the modified base has its intended effect.

FIG. 28. (SEQ ID NOS:256, 264–265) Experiments with probe sequence 5'-GCCAGGCAATTTTATTTGC (SEQ ID NO:256), which also forms a stable hairpin loop. This result clearly shows that the modified base-pair is having its intended effect. Placement of the modified base-pair closer to the extension site (3'-end) can have an even more dramatic impact.

FIG. 29. (SEQ ID NOS:266–273) Experiments with three different probe sequences with natural bases. The probes are extended during an SBE assay in the absence of any target. But, when natural bases are replaced with modified bases/nucleosides, target dependent signal from each one of them increases 5-fold.

FIG. 30. Modifications of bases in the "stem" region of capture probes inhibits self extension by preventing the polymerase enzyme from binding to the stem-loop structure.

FIG. 31. The thermodynamic stability of the probe-target duplex allows polymerase enzyme activity and extension is not compromised.

FIG. 32A depicts a modified nucleotide bases used in the "stem" region that reduce the binding affinity of the SBE enzyme (polymerase).

FIG. 32B depicts four chiral phosphodiester analogues that may be used in the "stem" structure of probes to prevent polymerase extension of stem-loop forming probes as follows: (a) A regular phosphodiester bond demonstrating the positions of the pro-R and pro-S non-bridging oxygens which are involved in hydrogen bond formation with enzyme protein contributing to binding affinity and specificity of the enzyme; and three chiral phosphodiester analogues that reduce enzyme binding: (b) an H-phosphonate: (c) a phosphorothionate; and (d) a methylphosphonate.

FIG. 33: Results from and SBE assay using "oligonucleotide inhibitors" to prevent self-extension of probes. A: modified SBE assay performed on RCA 1 SNP chip without both single stranded RNA targets and inhibitor. The false positive signal of APO E321.T.A. are indicated in framed box. B: Single-stranded RNA were applied on RCA SNP chip. The intensities of false positive signal in APO E are the same as that of in A. C: The single-strand RNA targets plus short oligo inhibitor were applied on RCA chip, the false positive signal of APO E321 was inhibited, and the signal is now similar in intensity to other positive signals present on the chip.

FIG. 34. Method for uniplexed target preparation for SNP genotyping and primer extension without self-extension. This combination of methods and modified enzyme defines one of the preferred embodiments of the invention.

FIG. 35. Results obtained from control probes wherein no PCR or other amplification technology was used for SNP genotyping. Primer extension preamplification followed by in vitro translation and then probe extension using a modified reverse transcriptase was used in this method.

FIG. 36. Demonstrates the advantage of the modified reverse transcriptase over the regular reverse transcriptase. The modified enzyme eliminates self-extension.

FIG. 37. Reaction of amino oligonucleotides on the SurModics™ surface. Here, an example of an acyl substitution reaction on the polymer backbone is shown.

FIG. 38. Possible structure of a SurModics™ Gel Matrix, a polymer used on a solid substrate in a preferred embodiment.

DETAILED DESCRIPTION OF THE INVENTION

The present invention is directed to methods and compositions, including biochips, comprising a particularly useful combination of probes designed to elucidate the genotypes (including the presence of single nucleotide polymorphisms, or SNPs) of a variety of p450 enzymes. The compositions and methods of the invention rely on the use of PCR primers (although, as will be appreciated by those in the art, other types of amplification reactions may be done as well), that provide unique and advantageous specificity between several of the p450 genes, to allow the specific amplification of each of the relevant genes. The resulting amplicons are then analyzed for SNPs using novel probes that improve the specificity and efficiency of the single base extension (SBE) reaction, to allow discrimination and detection of p450 enzyme variants, which allows correlation to disease states and drug susceptibility and resistance.

Accordingly, it is an object of the present invention to provide compositions and methods for analyzing and evaluating samples from one or more patients, to ascertain the level and/or genotype of various P450 enzymes present. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred). As will be appreciated by those in the art, the sample may be the product of an amplification reaction, including both target and signal amplification as is generally described in PCT/US99/01705, such as PCR, etc., amplification reactions and outlined below. As will be appreciated by those in the art, virtually any experimental manipulation may have been done on the sample.

The compositions and methods of the invention are directed to the detection of SNPs on target DNA sequences. The term "target sequence" or "target nucleic acid" or "target analyte" or grammatical equivalents herein means a nucleic acid sequence, that may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction such as PCR etc. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of SNPs in the target sequence of a sample. Generally speaking, this term will be understood by those skilled in the art. The target sequence may also be comprised of different target domains; for example, a first target domain of the sample target sequence may hybridize to a first capture probe, a second target domain may hybridize to a portion of a capture probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

Single base changes that are inherited are generally referred to as polymorphisms or SNPs. As is more fully outlined below, preferred embodiments of the invention comprise target sequences comprising a SNP (single nucleotide polymorphism) or a plurality of SNPs for which sequence information is desired, generally referred to herein as "SNP site" or "SNP position" or the "queried base" or the "interrogation position" or the "detection position". In a preferred embodiment, the SNP position is a single nucleotide, although in some embodiments, it may comprise a plurality of nucleotides, either contiguous with each other or separated by one or more nucleotides. By "plurality" as used herein is meant at least two. As used herein, the capture probe comprises the "interrogation position", usually, but not always, at the 3' end or towards the 3' end.

For the purposes of this invention, sequences are referred to herein as "perfectly matched" or "mismatched". It should be noted in this context that "mismatch" is a relative term and meant to indicate a difference in the identity of a base between two sequences in two different probes at the particular SNP position. In general, sequences that differ from wild type sequences are referred to as mismatches. However, and particularly in the case of SNPs, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as a "perfect match", or a "mismatch" or a "mutant" with respect to a wild type sequence standard. "Mismatches" sometimes also refer to "allelic variants". The term "allele", which is used interchangeably herein with "allelic variant" refers to alternative forms of a gene or portions thereof. Alleles occupy the same locus or position on homologous chromosomes. When a subject has two identical alleles of a gene, the subject is said to be 'homozygous' for the gene or allele. When a subject has two different alleles of a gene, the subject is said to be 'heterozygous' for the gene. Alleles of a specific gene can differ from each other in a single nucleotide, or several nucleotides, and can include substitutions, deletions, and insertions of nucleotides. An allele of a gene can also can be a form of a gene containing a mutation. The term "allelic variant of a polymorphic region of a gene" refers to a region of a gene having one of several nucleotide sequences found in that region of the gene in other individuals of the same species. Thus the above terms have to be used in context to derive the full meaning of the term.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252–3 (1998); positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. The definition also include "locked nucleic acids". All of these references are hereby expressly incorporated by reference. These modifications of the ribose-phosphate backbone may be done to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be 'single stranded' or 'double stranded', as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

If required, the target sequence is prepared using known techniques. For example, the sample may be treated to lyse the cells, using known lysis buffers, electroporation, etc., with purification and/or amplification as needed, as will be appreciated by those in the art. Suitable amplification techniques to amplify target nucleic acids are outlined in PCT US99/01705, hereby expressly incorporated by reference and outlined below.

General techniques for target sequence amplification are discussed below. The primers or probes used herein permit amplification of the target DNA, as is well understood in the art.

Target amplification involves the amplification (replication) of the target sequence such that the number of copies of the target sequence is increased. Suitable target amplification techniques include, but are not limited to, the polymerase chain reaction (PCR), allelic PCR, strand displacement amplification (SDA), and nucleic acid sequence based amplification (NASBA), oligonucleotide ligation assay (OLA), rolling circle amplification (RCA), Invader™ technology, using scissile primers (CPT) etc., defined below.

Different amplification techniques may have further requirements of primers or probes, as is more fully described below. The size of the primer nucleic acid may vary, as will be appreciated by those in the art, in general varying from 5 to 500 nucleotides in length, depending on the use and amplification technique.

Once the complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identification of the enzyme will depend on the amplification technique used, as is more fully outlined below.

In a preferred embodiment, the target amplification technique is PCR. The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which can be used in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtraction", among others. The particulars of PCR are well known, and include the use of a thermostable polymerase such as Taq I polymerase and thermal cycling. Accordingly, the PCR reaction requires at least one PCR primer and a polymerase.

Multiplex PCR amplification of SNP loci with subsequent hybridization to oligonucleotide arrays has been shown to be an accurate and a reliable method of simultaneously genotyping at least hundreds of SNPs; see Wang et al., Science, 280:1077 (1998); see also Schafer et al., Nature Biotechnology 16:33–39 (1998). Multiplex PCR reactions involving different primer sets for different regions of the target DNA can be used for amplifying target DNA. In a preferred embodiment, a 7-multiplex PCR reaction is performed to amplify seven different regions, each region corresponding to a different SNP position of the target DNA, using appropriate primer sets. Amplicons are pooled and the total pool is used for analysis. Thus, for example, if 10 SNP positions were amplified by PCR, 7×10=70 SNP positions can be interrogated at a time for each amplified DNA sample; for example, on a p450 chip.

An additional amplification method is allelic PCR, described in Newton et al., Nucl. Acid Res. 17:2503 (1989), hereby expressly incorporated by reference. Allelic PCR allows single base discrimination based on the fact that the PCR reaction does not proceed well if the terminal 3'-nucleotide is mismatched, assuming the DNA polymerase being used lacks a 3'-exonuclease proofreading activity.

In a preferred embodiment, the target amplification technique is SDA. Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby expressly incorporated by reference in their entirety. In general, SDA may be described as follows. A single stranded target nucleic acid, usually a DNA target sequence, is contacted with an SDA primer generally with a length of 25–100 nucleotides. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease". The SDA primer then hybridizes to the target sequence. The SDA reaction mixture also contains a polymerase (an "SDA polymerase") and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'-O-(1-thiotriphosphate), 5-methyldeoxycytidine 5'-triphosphate, 2'-deoxyuridine 5'-triphosphate, adn 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'-3' exonuclease activity. However, if less than all the nucleotides are substituted, the polymerase preferably lacks 5'-3' exonuclease activity. A chart depicting suitable enzymes, and their corresponding recognition sites and the modified dNTP to be used is found in U.S. Pat. No. 5,455,166, hereby expressly incorporated by reference.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, the target amplification technique is nucleic acid sequence based amplification (NASBA). NASBA is generally described in U.S. Pat. No. 5,409,818; Sooknanan et al., Nucleic Acid Sequence-Based Amplification, Ch. 12 (pp. 261–285) of Molecular Methods for Virus Detection, Academic Press, 1995; and "Profiting from Gene-based Diagnostics", CTB International Publishing Inc., N.J., 1996, all of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques may be described as follows. A single stranded target nucleic acid, usually an RNA target sequence (sometimes referred to herein as "the first target sequence" or "the first template"), is contacted with a first primer, generally referred to herein as a "NASBA primer" (although "TMA primer" is also suitable). Starting with a DNA target sequence is described below. These primers generally have a length of 25–100 nucleotides, with NASBA primers of approximately 50–75 nucleotides being preferred. The first primer is preferably a DNA primer that has at its 3' end a sequence that is substantially complementary to the 3' end of the first template. The first primer also has an RNA polymerase promoter at its 5' end (or its complement (antisense), depending on the configuration of the system). The first primer is then hybridized to the first template to form a first hybridization complex. The reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT. When the amplification reaction is TMA, the reverse transcriptase enzyme further comprises a RNA degrading activity.

In a preferred embodiment, the "reverse transcriptase" is a modified reverse transcriptase (RT) in which the DNA-dependent DNA polymerase activity has been eliminated. Here, self-extending probes are not extended by the modified RT because these are DNA-dependent extensions and only probe bound to RNA targets will be extended by the RNA-dependent DNA polymerase activity.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from E. coli and calf thymus.

The ribonuclease activity degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the 3' end of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage ϕII, *Salmonella* phage sp6, or *Pseudomonase* phage gh-1.

In some embodiments, TMA and NASBA are used with starting DNA target sequences. In this embodiment, it is necessary to utilize the first primer comprising the RNA polymerase promoter and a DNA polymerase enzyme to generate a double stranded DNA hybrid with the newly synthesized strand comprising the promoter sequence. The hybrid is then denatured and the second primer added.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

Accordingly, the TMA reaction requires, in no particular order, a first TMA primer, a second TMA primer comprising an antisense sequence of an RNA polymerase promoter, an RNA polymerase that recognizes the promoter, a reverse transcriptase with RNA degrading activity, a DNA polymerase, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

In a preferred embodiment, the target amplification technique is the oligonucleotide ligation assay (OLA), sometimes referred to as the ligation chain reaction (LCR). The method can be run in two different ways; in a first embodiment, only one strand of a target sequence is used as a template for ligation (OLA); alternatively, both strands may be used (OLA). Oligonucleotide ligation amplification ("OLA", sometimes referred to herein as the ligation chain reaction (LCR)) involves the ligation of two smaller probes into a single long probe, using the target sequence as the template. See generally U.S. Pat. Nos. 5,185,243 5,679,524 and 5,573,907; EP 0 320 308 B1; EP 0 336 731 B1; EP 0 439 182 B1; WO 90/01069; WO 89/12696; and WO 97/31256, WO 89/09835, and U.S. Pat. Nos. 60/078,102 and 60/073,011, all of which are incorporated by reference.

A variation of LCR utilizes a "chemical ligation" of sorts, as is generally outlined in U.S. Pat. Nos. 5,616,464 and 5,767,259, both of which are hereby expressly incorporated by reference in their entirety. In this embodiment, similar to LCR, a pair of primers are utilized, wherein the first primer is substantially complementary to a first domain of the target and the second primer is substantially complementary to an adjacent second domain of the target (although, as for LCR, if a "gap" exists, a polymerase and dNTPs may be added to "fill in" the gap). Each primer has a portion that acts as a "side chain" that does not bind the target sequence and acts one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes.

At least one of the side chains of the primers comprises an activatable cross-linking agent, generally covalently attached to the side chain, that upon activation, results in a chemical cross-link or chemical ligation. The activatable group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the disassociation of the hybridization complex, thus freeing up the target to serve as a template for the next ligation or cross-linking. In this way, signal amplification occurs, and can be detected as outlined herein.

In a preferred embodiment the target amplification technique is RCA. A variation of OLA which can also be used for genotyping is termed "rolling circle amplification" or RCA. Rolling circle amplification utilizes a single probe that hybridizes to a target such that each terminus of the probe hybridizes adjacently to each other (or, alternatively, the intervening nucleotides can be "filled in" using a polymerase and dNTPs). Then, upon ligation of the two termini of the probe, a circular probe is formed, also referred to as a "padlock probe" or the "RCA probe". Then, a primer and a polymerase is added such that the primer sequence is extended. But as the circular probe has no terminus, the polymerase repeatedly extends the circular probe resulting in concatamers of the circular probe. As such, the probe is amplified. The resultant amplicon can be cleaved in a variety of ways for further use in assays. Rolling-circle amplification is generally described in Baner et al. (1998) *Nuc. Acids Res.* 26:5073–5078; Barany, F. (1991) *Proc. Natl. Acad. Sci. USA* 88:189–193; Lizardi et al. (1998) *Nat. Genet.* 19:225–232; Zhang et al., Gene 211:277 (1998); and Daubendiek et al., Nature Biotech. 15:273 (1997); all of which are incorporated by reference in their entirety.

In a preferred embodiment, the RCA probes comprise a cleavage site, such that either after or during the rolling circle amplification, the RCA concatamer may be cleaved into amplicons. In some embodiments, this facilitates the detection, since the amplicons are generally smaller and exhibit favorable hybridization kinetics on the surface. As will be appreciated by those in the art, the cleavage site can take on a number of forms, including, but not limited to, the use of restriction sites in the probe, the use of ribozyme sequences, or through the use or incorporation of nucleic acid cleavage moieties.

In a preferred embodiment, the padlock probe or RCA probe contains a restriction site. The restriction endonuclease site allows for cleavage of the long concatamers that are typically the result of RCA into smaller individual units that hybridize either more efficiently or faster to surface bound capture probes. Thus, following RCA (or in some cases, during the reaction), the product nucleic acid is contacted with the appropriate restriction endonuclease. This results in cleavage of the product nucleic acid into smaller fragments. The fragments are then hybridized with the capture probe that is immobilized resulting in a concentration of product fragments onto the detection electrode.

In a preferred embodiment, the cleavage site is a ribozyme cleavage site as is generally described in Daubendiek et al., Nature Biotech. 15:273 (1997), hereby expressly incorporated by reference. In this embodiment, by using RCA probes that encode catalytic RNAs, NTPs and an RNA polymerase, the resulting concatamer can self cleave, ultimately forming monomeric amplicons.

In a preferred embodiment, cleavage is accomplished using DNA cleavage reagents. For example, as is known in the art, there are a number of intercalating moieties that can effect cleavage, for example using light.

Thus, in a preferred embodiment the OLA/RCA is performed in solution followed by restriction endonuclease cleavage of the RCA product. The cleaved product is then applied to an array as described herein. The incorporation of an endonuclease site allows the generation of short, easily hybridizable sequences. Furthermore, the unique capture sequence in each rolling circle padlock probe sequence allows diverse sets of nucleic acid sequences to be analyzed in parallel on an array, since each sequence is resolved on the basis of hybridization specificity.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected. By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal.

In a preferred embodiment, Invader™ technology is used. Invader™ technology is based on structure-specific polymerases that cleave nucleic acids in a site-specific manner. Two probes are used: an "invader" probe and a "signaling" probe, that adjacently hybridize to a target sequence with a non-complementary overlap. The enzyme cleaves at the overlap due to its recognition of the "tail", and releases the "tail". This can then be detected. The Invader™ technology is described in U.S. Pat. Nos. 5,846,717; 5,614,402; 5,719,028; 5,541,311; and 5,843,669, all of which are hereby incorporated by reference.

By "extension enzyme" herein is meant an enzyme that will extend a sequence by the addition of NTPs. As is well known in the art, there are a wide variety of suitable extension enzymes, of which polymerases (both RNA and DNA, depending on the composition of the target sequence and precircle probe) are preferred. Preferred polymerases are those that lack strand displacement activity, such that they will be capable of adding only the necessary bases at the end of the probe, without further extending the probe to include nucleotides that are complementary to a targeting domain and thus preventing circularization. Suitable polymerases include, but are not limited to, both DNA and RNA polymerases, including the Klenow fragment of DNA polymerase I, SEQUENASE 1.0 and SEQUENASE 2.0 (U.S. Biochemical), T5 DNA polymerase, Phi29 DNA polymerase and various RNA polymerases such as from *Thermus* sp., or Q beta replicase from bacteriophage, also SP6, T3, T4 and T7 RNA polymerases can be used, among others.

Even more preferred polymerases are those that are essentially devoid of a 5' to 3' exonuclease activity, so as to assure that the probe will not be extended past the 5' end of the probe. Exemplary enzymes lacking 5' to 3' exonuclease activity include the Klenow fragment of the DNA Polymerase and the Stoffel fragment of DNAPTaq Polymerase. For example, the Stoffel fragment of Taq DNA polymerase lacks 5' to 3' exonuclease activity due to genetic manipulations, which result in the production of a truncated protein lacking the N-terminal 289 amino acids. (See e.g., Lawyer et al., J. Biol. Chem., 264:6427–6437 [1989]; and Lawyer et al., PCR Meth. Appl., 2:275–287 [1993]). Analogous mutant polymerases have been generated for polymerases derived from *T. maritima*, Tsps 17, TZ05, Tth and Taf.

In the above embodiments, the polymerases can be any polymerase with unique features as explained in each case or as outlined herein, preferably one lacking 3' exonuclease activity (3' exo⁻). Examples of suitable polymerase include but are not limited to exonuclease minus DNA Polymerase I large (Klenow) Fragment, Phi29 DNA polymerase, *Taq* DNA Polymerase, Deep vent (exo⁻), thermosequenase and the like. In addition, in some embodiments, a polymerase that will replicate single-stranded DNA (i.e. without a primer forming a double stranded section) can be used.

In a preferred embodiment, the polymerase creates more than 100 copies of the circular DNA. In more preferred embodiments the polymerase creates more than 1000 copies of the circular DNA; while in a most preferred embodiment the polymerase creates more than 10,000 copies or more than 50,000 copies of the template, thus amplifying the target sequence.

In certain preferred embodiments, terminal transferase can be used to add nucleotides comprising separation labels such as biotin to any linear molecules, and then the mixture run through a streptavidin system to remove any linear nucleic acids, leaving only the closed circular probes. For example, as in the RCA method, when genomic DNA is used as the target, the DNA may be biotinylated using a variety of techniques, and precircle probes added and circularized. Since the circularized probes are catenated on the genomic DNA, the linear unreacted precircle probes can be washed away. The closed circle probes can then be cleaved, such that they are removed from the genomic DNA, collected and amplified.

Thus, using the amplification methods outlined above, a number of target molecules are made for hybridization to probes in the assays of the invention. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred. As is more fully outlined below, the products of these reactions can be detected in a number of ways, as is generally outlined in U.S. Ser. Nos. 09/458,553; 09/458,501; 09/572,187; 09/495,992; 09/344,217; WO00/31148; Ser. Nos. 09/439,889; 09/438,209; 09/344,620; PCT US00/17422; Ser. No. 09/478,727, all of which are expressly incorporated by reference in their entirety. Also, when the binding ligand or probe is a nucleic acid, preferred compositions and techniques outlined in U.S. Pat. Nos. 5,591,578; 5,824,473; 5,705,348; 5,780,234 and 5,770,369; U.S. Ser. Nos. 08/873,598 08/911,589; WO 98/20162; WO98/12430; WO98/57158; WO 00/16089) WO99/57317; WO99/67425; WO00/24941; PCT US00/10903; WO00/38836; WO99/37819; WO99/57319 and PCTUS00/20476; and related materials, are expressly incorporated by reference in their entirety.

In a preferred embodiment, the amplification technique is signal amplification. Signal amplification involves the use of limited number of target molecules as templates to either generate multiple signaling probes or allow the use of multiple signaling probes. Signal amplification strategies include LCR, CPT, Invader™, and the use of amplification probes in sandwich assays.

In most cases, double stranded target nucleic acids are denatured to render them single stranded so as to permit hybridization of the probes described below. For denaturing the target DNA, preferred embodiment utilizes a thermal step, generally by raising the temperature of the reaction to about 95° C., although pH changes and other techniques such as the use of extra probes or nucleic acid binding proteins may also be used.

Amplified target DNA is then contacted with the various types of probes described below to form a hybridization complex.

By "probe nucleic acid" is meant an oligonucleotide that will hybridize to some portion or a domain of the target sequence. The probe is also referred to as a "capture probe", "SBE probe" or a "microarray probe" or sometimes, an "extension probe". Depending on whether the probe is complementary to the WT or the mutant target sequence, the probe may sometimes be referred to as the "WT probe" or the "mutant probe". Probes of the present invention are designed to be complementary to a target sequence or an amplicon of the target sequence such that hybridization of the target sequence and the probes of the present invention occurs. As is outlined above, this complementarity need not be perfect; that is, there may be any number of base pair mismatches which will interfere with hybridization between the target sequence and the capture probes of the present invention. In preferred embodiments, the capture probe is single stranded. In another preferred embodiment, the capture probe is modified, as described below, wherein the probe is referred to as a "modified capture probe" or a "modified probe". As is more fully outlined below, in some embodiments, the capture probe comprises additional bases (usually one additional base) to prevent self-extension. When the probe or primer is modified to prevent self-extension, it is referred to herein as a "non-self extension probe".

In a preferred embodiment, contacting is done to probes attached to a biochip and are designed to be "substantially complementary" to a target sequence, such that hybridization of the target sequence and the probes of the present invention occurs. As outlined below, this complementarity need not be perfect; there may be any number of base pair mismatches which will interfere with hybridization between the target sequence and the capture probe of the present invention. However, if the number of mutations is so great that no hybridization can occur under even the least stringent of hybridization conditions, the sequence is not a complementary target sequence. Thus, by "substantially complementary" herein is meant that capture probes are sufficiently complementary to the target sequences to hybridize under normal reaction conditions, particularly high stringency conditions, as outlined herein. The term "complementary", in the context of a nucleic acid sequence, means a nucleic acid sequence having a sequence relationship to a second nucleic acid sequence such that there is perfect alignment of Watson-Crick base pairs along the entire length of both nucleic acid sequences.

A variety of hybridization conditions may be used in the present invention, typically classified by the degree of "stringency" of the conditions, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Stringency can be controlled by altering a step parameter that is a thermodynamic variable, including, but not limited to, temperature, formamide concentration, salt concentration, chaotropic salt concentration pH, organic solvent concentration, etc. These parameters may also be used to control non-specific binding, as is generally outlined in U.S. Pat. No. 5,681,697. Thus it may be desirable to perform certain steps at higher stringency conditions to reduce non-specific binding.

The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). For example, "maximum stringency" typically occurs at about Tm-5° C. (50 below the Tm of the probe); "high stringency" at about 5–10° below the Tm; "intermediate stringency" at about 10–20° below the Tm of the probe; and "low stringency" at about 20–25° below the Tm. In general, hybridization conditions are carried out under high ionic strength conditions, for example, using 6×SSC or 6×SSPE. Under high stringency conditions, hybridization is followed by two washes with low salt solution, for example 0.5×SSC, at the calculated temperature. Under medium stringency conditions, hybridization is followed by two washes with medium salt solution, for example 2×SSC. Under low stringency conditions, hybridization is followed by two washes with high salt solution, for example 6×SSC. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993).

Thus, stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides).

Stringent conditions may also be achieved with the addition of destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex. Preferred embodiments of the present invention may use "competimers" on arrays, to reduce non-specific binding.

Thus, the assays of the present invention are generally run under stringency conditions which allows formation of the hybridization complex only in the presence of target, but occasionally, less stringent conditions may be used. For example, enzymatic extension may require less stringent hybridization conditions as assay selectivity is enhanced by the enzyme, as is generally understood in the art. Details of conditions used in preferred embodiments of this invention are further described below. Furthermore, preferred embodiments use arrays such that the capture probes bind to the target DNA in a sequence-specific manner, and permits the unbound material to be washed away.

Preferred embodiment of the present invention uses the single base extension (SBE; sometimes also called minisequencing) assay and its variations, described herein. In a general SBE assay, two capture probes (wild type (WT) and mutant) that differ only in their terminal bases are synthesized such that, one of the two capture probes is perfectly complementary to the "queried base" or the "interrogation position" of the target sequence to be analyzed. That is, the capture probes include the interrogation or SNP base. Under normal hybridization conditions, both the WT and the mutant probe can hybridize to the target sequence. But enzymes such as ligases or polymerases, defined above, can distinguish a perfect or an imperfect match such that, enzymatic extension by a single chain terminating base (sometimes carrying the label for detection), occurs only if a perfect duplex is present. That is, the DNA polymerase can extend the capture probe by one base in the presence of four labeled-terminator nucleotides, only if there is perfect hybridization. Else, a 3' base mismatch results in breathing and dissuades primer extension. By "terminator nucleotides" is meant that the nucleotide is derivatized such that no further extensions can occur, so only one nucleotide is added. Preferred embodiments utilize dideoxy-triphosphate nucleotides (ddNTPs) and generally a set of nucleotides comprising ddATP, ddCTP, ddGTP and ddTTP is used, at least one of which includes a label, and preferably all four. The labels may be different or the same, as specified. Once the labeled nucleotide is added, detection of the label proceeds as outlined below. See generally Sylvanen et al., Genomics 8:684–92 (1990); U.S. Pat. Nos. 5,846,710 and 5,888,819; Pastinen et al., Genomics Res. 7(6):606–14 (1997); all of which are expressly incorporated herein by reference. Thus, the identity of the SNP or queried base in the target is determined by the probe set that is extended by the DNA polymerase. In a variation of this type of assay, the probes terminate at a position one base upstream of the queried base in the target.

A limitation of the SBE method is that unless the target nucleic acid is in sufficient concentration, the amount of unextended primer in the reaction greatly exceeds the resultant extended-labeled primer. The excess of unextended primer competes with the detection of the labeled primer in the assays described herein. Accordingly, when SBE is used, preferred embodiments utilize methods for the removal of unextended primers as outlined herein.

One method to overcome this limitation is thermocycling minisequencing in which repeated cycles of annealing, primer extension, and heat denaturation using a thermocycler and thermo-stable polymerase allows the amplification of the extension probe which results in the accumulation of extended primers. For example, if the original unextended primer to target nucleic acid concentration is 100:1 and 100 thermocycles and extensions are performed, a majority of the primer will be extended.

As will be appreciated by those in the art, the configuration of the SBE system can take on several forms. The SBE reaction may be done in solution, and then the newly synthesized strands, with the base-specific detectable labels, can be detected. For example, they can be directly hybridized to capture probes that are complementary to the extension primers, and the presence of the label is then detected.

Alternatively, the SBE reaction can occur on a surface. For example, a target nucleic acid may be captured using a first capture probe that hybridizes to a first target domain of the target, and the reaction can proceed at a second target domain. The extended labeled primers are then bound to a second capture probe and detected.

Thus, the SBE reaction requires, in no particular order, an extension primer, a polymerase and dNTPs, at least one of which is labeled.

The following references, relating to SBE, are hereby expressly incorporated by reference in their entireity: U.S. Pat. Nos. 5,639,611; 5,824,476; 5,981,176; 4,851,331; 5,888,819; 6,004,744; 5,137,806; 6,287,778 B1; 5,582,970; 6,307,039; 6,013,431; 5,846,710; 5,710,028; 6,153,379; 5,665,539; 6,287,778; 5,856,092; WO 92/15712; U.S. Pat. No. 4,656,127; EPO 371437 B1; U.S. Pat. Nos. 5,595,890; 6,015,675; 5,578,458.

Specificity remains a problem in many currently available SBE assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

Two major hurdles for highly parallel screening of SNPs on microarrays are 1) the necessity to amplify DNA regions spanning the SNPs by PCR to achieve sufficient sensitivity and specificity of detecting a single-base variation in the complex human genome in a reproducible way; and, 2) the ability to distinguish unequivocally between homozygous and heterozygous allelic variants in the diploid human genome. Differential hybridization with allele-specific oligonucleotide (ASO) probes is most commonly used in the microarray format (Pastinen et al., Genome Res. 10:1031–42 (2000) hereby expressly incorporated by reference).

A problem associated with the SBE assay is that, some probes used in the assay form internal "stem-loop structures" resulting in target-independent 'self-extension' of the probe, thus giving a false positive signal that interferes with the determination of the SNP base. To overcome these problems, this invention recites several preferred embodiments described herein involving novel designs of capture probes, and/or, the use of a novel combination of methods involving uniplexed target preparation and primer extension with modified polymerases to avoid self-extension.

That is, the present invention provides methods for preventing self extension of primers on an array. The present invention also provides an array with modified primers. Preferably the primers are modified as described herein. In some embodiments, the arrays include primers that include modified nucleotides. Modified nucleotides include exocyclic amine modified bases like 2-thio thymine, 2-amino adenine, amine modified cytosine, amine modified guanine, or terminator bases like 4-methylindole. In some methods of the invention, the modified nucleotides alter the polymerase binding or protein binding to the stem region of the non self-extension probe, wherein the modified nucleotides are present. Modified nucleotides also comprises a sugar and phosphate modifications.

Some preferred phosphate modifications include, but are not limited to phosphorothioates, phosphoramidates, methyl phosphonates, methyl phosphates, H-phosphonates.

In another preferred embodiment, to prevent self-extension, short complementary oligonucleotides are used whereby self-extension is inhibited.

Details of the modified nucleotides used in preferred embodiments of the invention is described herein.

In one preferred embodiment, the capture probe is designed such that it terminates at one or more bases downstream of the queried SNP site in the probe. Generally, a stem of three or more base pairs is required for self-extension. The bases added downstream are designed such that they are complementary to the bases in the target but are mismatched at the 3' end of the stem-loop structure. If there is a mismatch between bases in the stem-loop, a bubble formed which induces breathing and prevents the DNA polymerase from extending the capture probe thus preventing false signal detection. In practice, adding four or more bases is not feasible since the SNP position will be too far upstream and may induce short duplex formation and polymerase dependent extension and thus, a false positive result. In a preferred embodiment, the number of additional bases added downstream of the SNP site on the probe is one, or two or three bases. Target dependent extension is not affected by the additional bases as the added bases are complementary to the target. Accordingly, the interrogation position is the 3' terminal nucleotide. Alternatively, the interrogation position is the penultimate nucleotide of the primer.

In another preferred embodiment to destabilize hairpin structures in probes, "modified base pairs" are incorporated into the probe that prevent self-extension but do not interfere with target hybridization. Such modified base pairs have been used before in applications of gene-therapy wherein each modified base of the "pair" are found in each complementary single stranded nucleic acid involved in gene therapy. Such modified base pairs include but are not limited to a) 2-amino-A:2-thio-T, b) 2-aminipurine:2-thio-T, c) 6-thio-G, d) 2-thio-C, e) hydrophobic bases such as 4-methylindole, difluorotoluene, etc.

In another preferred embodiment, the capture probe comprises modified phosphates or sugars in the stem region of the probe to reduce stem-loop structures and thus false positives. It is well known in the art that the phosphate backbone of the nucleic acid plays an important role in nucleic acid-protein interactions. Electrostatic interactions between the positively charged amino acids of a protein and the negatively charged phosphate backbone and the formation of hydrogen bonds between the phosphate oxygen and protein contribute to the binding affinity of a particular protein or enzyme to a nucleic acid. In this preferred embodiment, by modifying the phosphate or the sugar rings of the probe backbone, one can decrease the binding affinity of the polymerase enzyme for the stem region thereby decreasing the probability of non-specific nucleotide incorporation. Such modifications are not performed at the queried base of the probe and hence, the thermodynamic stability of the probe-target duplex is not altered. Examples of such modified nucleic acids are described below.

In the current invention, several surface charge modifications for probes are proposed herein, including, but not limited to, phosphorothionate, phosphoramidate, methyl phosphonate and methyl phosphate modifications of the phosphate backbone and 2' O-methyl modifications on the sugar ring). Phosphorothionate (sulfur substitution) and phosphoramidate (nitrogen substitution) substitutions alters the charge distribution, hydrophobicity and the ability for an enzyme to form efficient hydrogen bonding with the phosphate backbone. Methyl phosphonate and methyl phosphate eliminate the phosphate charge altogether, thus inhibiting the binding of the enzyme to the DNA altogether (see Smith, S A and McLaughlin, Biochemistry 36: 6046–58 (1997) and Dertinger et al., Biochemistry 39: 55–63 (2000), hereby expressly incorporated by reference).

In yet another preferred embodiment, inhibitory oligonucleotides are used. The invention makes use of complementary short oligonucleotides that create a blunt end on the probe oligonucleotides and prevent generation of false signals that are generated by enzymatic self-extension of probes. The signal of interest is only created in the presence of target and all other times the signal remains in the off mode (see FIG. 33). Short complementary APO E321.T.A oligo to APO E321.T.A SNP probe can inhibit APO E321.T.A SNP probe self-extension.

In another preferred embodiment, a combination of technologies is used wherein the combined result produces a marked reduction in false positive results due to self-extension. Here, three different technologies, PEP (primer extension preamplification), IVT (in vitro transcription) and probe extension with a modified reverse transcriptase are used that allow genome-wide SNP genotyping without multiple PCRs, without RCA (or other signal amplification technologies), and without problems from primer extension. The method involves performing a PEP (primer extension preamplification) reaction (known in U.S. Pat. No. 6,183,958; Zhang et al., Proc. Natl. Acad. Sci. 89:5847–51 (1992); Casas and Kirkpatrick, Biotechniques, 20: 219–25 (1996)) with random primers to amplify the genomic DNA in one reaction, followed by an IVT reaction (if one of the primers had a polymerase promoter sequence). The product, cRNA, is hybridized to the probe which is extended using a modified reverse transcriptase (RT) in which the DNA-dependent DNA polymerase activity has been eliminated. This means that self-extenders will not be extended by the RT because these are DNA-dependent extensions and only probe bound to RNA targets will be extended because these rely on the RNA-dependent DNA polymerase activity. Hence, self-extension is reduced.

A preferred embodiment of the present invention comprises an "array" of capture probes, including the WT and the mutant probe to a queried base, as described above, that are attached or immobilized to a solid support. The spatial location of the label on the solid support indicates the array element that shares a complementary sequence with the target, that is, whether the WT or the mutant base occurs in the DNA target. If both the WT and the mutant probes give a signal on detection, it indicates the presence of a heterozygote in the DNA sample.

By "array" herein is meant a plurality of probes in an array format; the size of the array will depend on the composition and end use of the array. Arrays containing from about 2 different translocation probes to many thousands can be made. Generally, the array will comprise from two to as many as 100,000 or more, depending on the size of the electrodes, as well as the end use of the array. Preferred ranges are from about 2 to about 10,000, with from about 5 to about 1000 being preferred, and from about 10 to about 100 being particularly preferred. In addition, each array also comprises a first chromosome control probe and a second chromosome control probe. In some embodiments, the compositions of the invention may not be in array format; that is, for some embodiments, compositions comprising a single capture ligand may be made as well. In addition, in some arrays, multiple substrates may be used, either of different or identical compositions. Thus for example, large arrays may comprise a plurality of smaller substrates.

Accordingly, as described above, the present invention provides arrays wherein the probes or primers includes "non self-extention probes or primers". That is, the probes or primers of the array are modified or designed such that they do not self-extend during primer extension reactions and thus minimize false positive reactions in the SBE assay.

In preferred embodiments, the invention includes a method of contacting the array that includes the non-self extendable primers described above with a target sample comprising P450 SNPs.

The devices of the invention describe a substrate with at least one surface comprising an array, and in a preferred embodiment, an array of electrodes. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Preferred electrodes are known in the art and include, but are not limited to, certain metals and their oxides, including gold; copper; silver; chromium; titanium; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), ruthenium oxides, and zinc oxide and tungsten oxide ($WO_3$; both of which are transparent); conductive plastics (such as polymers like polythiophenes, polyacrylamide, polyanilines, polypyrroles, and metal impregnated polymers); and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode. The conformation of the electrode will vary with the detection method used. For example, flat planar electrodes may be preferred for optical detection methods or when arrays of nucleic acids are made, thus requiring addressable locations for detection. That is, each electrode has an interconnection attached to the electrode at one end and to a device that can control the electrode, on the other end thereby making each electrode independently addressable.

Alternatively, the electrode may be in the form of a tube comprising polymers, as will be described, and nucleic acids bound to the inner surface. This allows a maximum of surface area containing the nucleic acids to be exposed to a small volume of sample.

In preferred embodiments where polymer layers are used on the detection surface of the electrode, the electrode comprise polymers that can help prevent electrical contact between the electrodes and the ETMs, or between the electrode and charged species within the solvent.

All of these techniques rely on the formation of assay complexes on the surface of an electrode as a result of hybridization of a target sequence (either the target sequence of the sample or a sequence generated in the assay) to a capture probe on the surface. The assay complex further comprises a detection label to aid detection of complex formation. In preferred embodiments, the detection label is either an electron transfer moiety (ETM), or a fluorescent moiety or any other label that is either directly or indirectly attached to the target. Labels and various detection systems are described below.

In addition, the present invention is directed to a novel invention that capitalizes on novel properties of surface-bound arrays, and uses "competimers" to reduce non-specific binding.

Nucleic acids arrays are well known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc.

By "substrate" or "solid support" or other grammatical equivalents herein is meant any material that can be modified to contain discrete individual sites appropriate for the attachment or association of nucleic acids. As will be appreciated by those in the art, the "substrates" outlined herein can be made from a wide variety of materials, including, but not limited to, silicon such as silicon wafers, silicon dioxide, silicon nitride, glass, fused silica, modified silicon, carbon, gallium arsenide, indium phosphide, aluminum, ceramics, polyimide, quartz, plastics, resins and polymers including polymethylmethacrylate, acrylics, polybutylene, polyurethanes, polyethylene, polyethylene terepthalate, polycarbonate, polystyrene and other styrene copolymers, polypropylene, polytetrafluoroethylene, Teflon, nylon or nitrocellulose, etc., polysaccharides, metal surfaces such as superalloys, zircaloy, steel, gold, silver, copper, tungsten, molybdeumn, tantalum, KOVAR, KEVLAR, KAPTON, MYLAR, brass, sapphire, etc. Preferred embodiments utilize glass, silicon and ceramic materials, depending on the reagents utilized. As will be appreciated by those in the art, the material comprising the substrate should be compatible with the reagents outlined herein.

As will be appreciated by those in the art, nucleic acid probes can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions. In general, the probes are attached to the biochip in a wide variety of ways, as will be appreciated by those in the art. As described herein, the nucleic acids can either be synthesized first, with subsequent attachment to the biochip, or can be directly synthesized on the biochip.

In a preferred embodiment, as is more fully outlined below, the substrate comprises a number of different layers, including electrodes, insulating layers and polymer layers, including, but not limited to, conductive polymers, polyacrylamide, polypyrrole, SurModics™ gel Matrices etc for attachment of probes to the support, as is generally described in WO 98/20162 and WO 99/57317, both of which are hereby expressly incorporated herein by reference in their entirety. In alternative embodiments, probes are attached to polymers that are in contact with the microelectrodes.

In a preferred embodiment, the polymer used for attaching the oligonucleotide probes of the array is the SurModics™ gel matrix. This is a polyacrylamide based gel that is derivatized to enable covalent attachment of oligonucleotides onto the polymer. For example, in FIG. 37, an example of an acyl substitution reaction is described through which an activated oligonucleotide can be attached to the polymer. The structure of the SurModics™ gel matrix is shown in FIG. 38. The method and platform include a substrate, the SurModics™ matrix and a number of oligonucleotide probes. Most commonly the substrate is a glass slide. Covalently attached to the glass slide is a thin polyacrylamide matrix. The polyacrylamide is functionalized with oligonucleotide attachment groups and photo-crosslinking groups. Different oligonucleotides of roughly 20–30 nucleotides are synthesized using standard phosphoramidite chemistry with an AminoLink™ terminal nucleotide, which comprises a $(CH_2)_6$—$NH_2$ linker. These oligonucleotides are spotted at discrete locations on the matrix. The probes are covalently attached to the matrix via an interaction with the AminoLink™ amino group and the oligonucleotide attachment groups present within the matrix. Once formed, the photo-crosslinked acrylamide matrix, with covalently attached oligonucleotide probes, is used in assaying a sample.

In this embodiment, the probes of the invention are arrayed onto slides coated with a film of hydrogel containing activated (NHS) esters ("3D-Link slides; cat.#: DN01-0025; Surmodics, Inc.; Eden Prairie, Minn.) employing a modified Badged II dispense robot (Packard, Meridian, Conn.; Motorola Life Sciences, Tempe, Ariz.).

By "insulating layer" herein is meant a layer of material that will not substantially transport electrons. Preferably, the insulating layer is a layer of insulative dielectric material, including, but not limited to, ceramics, plastics, printed circuit board materials, polymers, metal oxide or nitrides such as $SiO_2$, $SiN_x$ or $AlO_x$.

In a preferred embodiment, the polymer layer uses polymers including, but not limited to, polypyrrole, polythiophene, polyaniline, polyfuran, polypyridine, polycarbazole, polyphenylene, poly(phenylenvinylene), polyfluorene, polyindole, polyacrylamide, agarose gel, polyethylene glycol, cellular, sol gels, dendrimers, metallic nanoparticles, carbon nanotubes, their derivatives, their copolymers, and combinations thereof, to increase the amount of probe concentration at a particular site. In preferred embodiments, the material comprises a neutral pyrrole matrix. To increase the probe loading capacity, porous matrix such as polyacrylamide, agarose, or sol gels are preferred. In these embodiments, probe molecules are attached onto a supporting matrix on the surface of the electrodes using the functional chemistry mentioned below. In alternative embodiments, probes are attached to polymers that are in contact with microelectrodes.

Furthermore, substrates are also referred to as "biochips". By "biochip" or equivalents herein is meant a substrate comprising an array of distinct biomolecules, particularly nucleic acids.

Preferred substrates also include printed circuit board (PCB) materials. Reference is made to U.S. Ser. No. 09/796, 077; PCT US00/34145; PCT US01/02664; PCT/US00/33499; PCT/US00/33497; PCT/US99/23324; WO 01/34302; WO 98/20162; WO 98/112430; WO 00/16089; WO 99/57317; WO 99/67425; WO 01/35100; WO 00/62931 WO 01/06016; WO 01/07665; and PCT/US01/01150, all of which are expressly incorporated by reference in their entirety.

In a preferred embodiment, the substrate also includes "array locations". Accordingly, the present invention provides compositions comprising substrates with a plurality of array locations. By "array locations" or "pads" or "sites" herein is meant a location on the substrate that comprises a covalently attached nucleic acid probe. Additionally, the present system finds particular utility in array formats, further described below, wherein there is a matrix of addressable detection electrodes (herein generally referred to "pads", "addresses" or "micro-locations").

The electrodes, in some preferred embodiments of this invention, comprise self-assembled monolayers (SAMs). By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. A majority of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. SAMs can also comprise conductive oligomers, described below.

As outlined herein, the efficiency of target sequence binding (for example, oligonucleotide hybridization) may increase when the sequence is at a distance from the detection electrode. Similarly, non-specific binding of biomolecules, including the target sequences, to a detection electrode is generally reduced when a monolayer is present. Thus, a monolayer facilitates the maintenance of the sequence away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the detection electrode.

By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons. In other preferred embodiments, the monolayer comprises electroconduit-forming species. By "electroconduit-forming species" or "EFS" herein is meant a molecule that is capable of generating sufficient electroconduits in a monolayer, generally of insulators to allow detection of electrons or ETMs at the surface.

In a preferred embodiment, the conductive oligomers have a conductivity, S, of from between about $10^{-6}$ to about $10^4$ $\Omega^{-1}$cm$^{-1}$, with from about $10^{-5}$ to about $10^3$ $\Omega^{-1}$cm$^{-1}$ being preferred, with these S values being calculated for molecules ranging from about 20 Å to about 200 Å. As described below, insulators have a conductivity S of about $10^{-7}$ $\Omega^{-1}$cm$^{-1}$ or lower, with less than about $10^{-8}$ $\Omega^{-1}$cm$^{-1}$ being preferred. See generally Gardner et al., Sensors and Actuators A 51 (1995) 57–66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during nucleic acid synthesis (such that nucleosides containing the conductive oligomers may be added to a nucleic acid synthesizer during the synthesis of the compositions of the invention), ii) during the attachment of the conductive oligomer to an electrode, or iii) during hybridization assays. In addition, conductive oligomers that will promote the formation of self-assembled monolayers are preferred. The oligomers of the invention comprise at least two monomeric subunits, as described herein. As is described more fully below, oligomers include homo- and hetero-oligomers, and include polymers.

In general, EFS have one or more of the following qualities: they may be relatively rigid molecules, for example as compared to an alkyl chain; they may attach to the electrode surface with a geometry different from the other monolayer forming species (for example, alkyl chains attached to gold surfaces with thiol groups are thought to attach at roughly 45° angles, and phenyl-acetylene chains attached to gold via thiols are thought to go down at 90° angles); they may have a structure that sterically interferes or interrupts the formation of a tightly packed monolayer, for example through the inclusion of branching groups such as alkyl groups, or the inclusion of highly flexible species, such as polyethylene glycol units; or they may be capable of being activated to form electroconduits; for example, photoactivatable species that can be selectively removed from the surface upon photoactivation, leaving electroconduits.

Preferred EFS include conductive oligomers, as defined below, and phenyl-acetylene-polyethylene glycol species, as well as asymmetrical SAM-forming disulfide species such as depicted the figures of U.S. Ser. No. 60/145,912 filed Jul. 27, 1999, hereby expressly incorporated by reference. However, in some embodiments, the EFS is not a conductive oligomer.

As will be appreciated by those in the art, nucleic acid probes can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that two moieties, the solid support and the probe, are attached by at least one bond, including sigma bonds, pi bonds and coordination bonds.

The method of attachment of the capture probe to the detection surface can be done in a variety of ways, depending on the composition of the "capture binding ligand" or "capture probe" and the composition of the detection surface. Both direct attachment or indirect attachment can be used. Indirect attachment is done using an attachment linker. In general, both ways utilize functional groups on the capture probe, the attachment linker or spacer, and the detection surface for covalent attachment. Preferred functional groups for attachment are amino groups, carboxy groups, oxo groups and thiol groups. These functional groups can then be attached, either directly or indirectly through the use of a linker, sometimes depicted herein as "Z". "Linkers" or "spacers" or "anchoring groups" are well known in the art; for example, homo- or hetero-bifunctional linkers as are well known (see 1994 Pierce Chemical Company catalog, technical section on cross-linkers, pages 155–200, incorporated herein by reference). Preferred modifications useful in the practice of the invention include, but are not limited to, —OH, —NH$_2$, —SH, —COOR (where R=H, lower (C$_{1-12}$) alkyl, aryl, heterocyclic alkyl or aryl, or a metal ion), —CN, or —CHO. Immobilization of such derivatized probes is accomplished by direct attaching of the probe molecules on the detection surface through a functional group such —OH, —SH, —NH$_2$. In a preferred embodiment, probes are covalently attached to a SurModics™ matrix which is a polyacrylamide based gel that is derivatized to enable covalent attachment of oligonucleotides onto the polymer. For example, in FIG. 37, an example of an acyl substitution reaction is described through which an activated oligonucleotide can be attached to the polymer. The structure of the SurModics™ gel matrix is shown in FIG. 38.

The present system finds particular utility in array formats, wherein there is a matrix of addressable detection electrodes (herein generally referred to "pads", "addresses" or "micro-locations").

Some array configurations are described herein. In a preferred embodiment CodeLink™ array technology is used, CodeLink™ technology provides an apparatus for performing high-capacity biological reactions on a biochip comprising a substrate having an array of biological binding sites. It provides a hybridization chamber having one or more arrays, preferably comprising arrays consisting of hydrophilic, 3-dimensional gel and most preferably comprising arrays consisting of 3-dimensional polyacrylamide gels, wherein nucleic acid hybridization is performed by reacting a biological sample containing a target molecule of interest with a complementary oligonucleotide probe immobilized on the gel. Nucleic acid hybridization assays are advantageously performed using probe array technology, which utilizes binding of target single-stranded DNA onto immobilized oligonucleotide probes. Preferred arrays include those outlined in U.S. Ser. Nos. 09/458,501, 09/459, 685, 09/464,490, 09/605,766, PCT/US00/34145, Ser. No. 09/492,013, PCT/US01/02664, WO 01/54814, Ser. Nos. 09/458,533, 09/344,217, PCT/US99/27783, Ser. No. 09/439, 889, PCT/US00/42053 and WO 01/34292 all of which are hereby incorporated by reference in their entirety.

In another preferred embodiment eSensor™ array technology is used. eSensor™ technology uses self-assembled monolayers (SAMs) on surfaces for binding and detection of biological molecules. SAMs are alkyl chains that protect an electrode from solution electronically active agents (e.g. salts). Electrochemical labels (e.g. ferrocene), which are initially bound to the label probe, flow to the electrode and back producing a detectable signal. See for example WO98/20162; PCT US98/12430; PCT US98/12082; PCT US99/01705; PCT/US99/21683; PCT/US99/10104; PCT/US99/

01703; PCT/US00/31233; U.S. Pat. Nos. 5,620,850; 6,197,515; 6,013,459; 6,013,170; and 6,065,573; and references cited therein. In other preferred embodiments, electronic array technology is used, as is further described below.

The present invention also has devices that allow for simultaneous multiple biochip analysis. In particular, the devices are configured to hold multiple cartridges comprising nucleic acid arrays, and allow for high throughput analysis of samples.

By "cartridge" herein is meant a casing or housing for the biochip. As outlined herein, and as will be appreciated by those in the art, the cartridge can take on a number of configurations and can be made of a variety of materials. Suitable materials include, but are not limited to, fiberglass, teflon, ceramics, glass, silicon, mica, plastic (including acrylics, polystyrene and copolymers of styrene and other materials, polypropylene, polyethylene, polybutylene, polycarbonate, polyurethanes, Teflon™, and derivatives thereof, etc.), etc. Particularly preferred cartridge materials are plastic (including polycarbonate and polyproplylene) and glass.

As will be appreciated by those in the art, the cartridge can comprise a number of components, including reaction chambers, inlet and outlet ports, heating elements including thermoelectric components, RF antennae, electromagnetic components, memory chips, sealing components such as gaskets, electronic components including interconnects, multiplexers, processors, etc.

The devices comprise a number of cartridge stations that are configured to receive the biochips, either same or different types of biochips, allowing analysis of different types of biochips. The stations can include a wide variety of different components, including but not limited to, thermocontrollers, signaling systems, sensors for leak detection, alphanumeric displays, and detectors. When preferred embodiments include the use of biochips comprising electrodes that rely on electrochemical detection, the devices and/or stations can comprise device boards and processors used in the detection process. The biochip cartridges comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample removed for detection, as described in detail in U.S. Ser. No. 09/904,175 filed Jul. 11, 2001, hereby incorporated by reference in its entirety.

In a preferred embodiment, the cartridge comprises a reaction chamber. Generally, the reaction chamber comprises a space or volume that allows the contacting of the sample to the biochip array. The volume of the reaction chamber can vary depending on the size of the array and the assay being done. In general, reaction chamber ranges from 1 nL to about 1 mL, with from about 1 to about 250 µl being preferred and from about 10 to about 100 µl being especially preferred. In some embodiments, to avoid the introduction of air bubbles into the reaction chamber (which can be disruptive to detection), the reaction chamber is less than the size of the sample to be introduced, to allow a slight overflow and thus ensure that the reaction chamber contains little or no air.

The reaction chamber of the cartridge comprises an inlet port for the introduction of the sample to be analyzed. The inlet port may optionally comprise a seal to prevent or reduce the evaporation of the sample or reagents from the reaction chamber. In a preferred embodiment the seal comprises a gasket, through which a pipette or syringe can be pushed. The gasket can be rubber or silicone or other suitable materials, such as materials containing cellulose.

The reaction chamber can be configured in a variety of ways. In a preferred embodiment, the reaction chamber is configured to minimize the introduction or retention of air bubbles or other sample impurities. Thus, in a preferred embodiment, the reaction chamber further comprises an outlet port to allow air or excess sample to exit the reaction chamber. Thus the fluid sample flows up into the reaction chamber and contacts the array. In some embodiments, the outlet port vents to either a waste storage well, to an external surface of the chip or cartridge, or, in a preferred embodiment, back into the inlet port. Thus for example a preferred embodiment utilizes a system wherein the exit port vents to the inlet port, preferably above the point of loading. For example, when a pipette is used to load the cartridge, the tip of the pipette extends below the exit port, such that air from the exit port is not introduced into the reaction chamber. In addition, the materials of the cartridge housing and biochip can be chosen to be similar in hydrophobicity or hydrophilicity, to avoid the creation of air bubbles.

In addition, in a preferred embodiment, the reaction chamber/inlet and/or outlet ports optionally include the use of valves. For example, a semi-permeable membrane or filter may be used, that preferentially allows the escape of gas but retains the sample fluid in the chamber. For example, porous teflons such as Gortex™ allow air but not fluids to penetrate.

As will be appreciated by those in the art, there are a variety of reaction chamber geometries which can be used in this way. Generally having the intersection of the inlet port and the reaction chamber be at the "bottom" of the cartridge, with a small aperture, with the reaction chamber widening, is preferred. In addition, the "top" of the reaction chamber may narrow, as well. Thus, preferred embodiments for the size and shape of the reaction chamber allow for smooth loading of the reaction chamber. Preferred embodiments utilize reaction chamber geometries that avoid the use of sharp corners or other components that serve as points for bubble formation.

In addition, in some embodiments, the reaction chamber can be configured to allow mixing of the sample. For example, when a sample and a reagent are introduced simultaneously or separately into the chamber, the inlet port and/or the reaction chamber can comprise weirs, channels or other components to maximize the mixing of the sample and reagent. In addition, as is outlined below, the reaction may utilize magnetic beads for mixing and/or separation.

In a preferred embodiment, the cartridge comprises a sealing mechanism to prevent leakage of the sample or reagents onto other parts of the substrate, particularly (in the case of electronic detection) onto electronic interconnects. As will be appreciated by those in the art, this may take on a variety of different forms. In one embodiment, there is a gasket between the biochip substrate comprising the array and the cartridge, comprising sheets, tubes or strips. Alternatively, there may be a rubber or silicone strip or tube used; for example, the housing may comprise an indentation or channel into which the gasket fits, and then the housing, gasket and chip are clamped together. Furthermore, adhesives can be used to attach the gasket to the cartridge, for example, a double sided adhesive can be used; for example, silicone, acrylic and combination adhesives can be used to attach the gasket to the biochip, which is then clamped into the cartridge as described herein.

In some embodiments, the reaction chamber and biochip substrate are configured such that a separate sealing mechanism is not required. For example, the biochip substrate can serve as one "half" of the reaction chamber, with the array on the inside, and the reaction chamber housing can serve as the other "half". Depending on the materials used, there may be an optional adhesive to attach the two. Alternatively, when there are arrays on both sides of the substrate, the housing may encompass the substrate.

Thus, in these embodiments, the volume of the reaction chamber can be set either by forming a well in the cartridge, such that the addition of the biochip substrate forms a reaction chamber around the array, or by using a flat cartridge and using a gasket of a defined depth, or by combinations of the two.

In a preferred embodiment, the cartridge comprises a cap or lid. The cap may be functional, as outlined below when it comprises microfluidic components. In addition, the cap may be designed for safety purposes, to prevent the leakage of biological materials or cross-contamination. Additionally, the cap can be designed to be removable. As will be appreciated by those in the art, the cap can take on a wide variety of configurations. For example, in one embodiment, the cap merely seals the inlet port to prevent evaporation of the sample during the assay. In a preferred embodiment, the cap may comprise a number of additional elements for use in sample handling and reagent storage, to allow for a variety of different sample reactions. For example, a variety of microfluidic components can be built into the cap to effect a number of manipulations on a sample to ultimately result in target analyte detection or quantitation. See generally PCT US00/10903, and references outlined therein, all of which are expressly incorporated by reference. These manipulations can include cell handling (cell concentration, cell lysis, cell removal, cell separation, etc.), separation of the desired target analyte from other sample components, chemical or enzymatic reactions on the target analyte, detection of the target analyte, etc. The devices of the invention can include one or more wells for sample manipulation, waste or reagents; microchannels (sometimes referred to as flow channels) to and between these wells, including microchannels containing electrophoretic separation matrices; valves to control fluid movement; on-chip pumps such as electroosmotic, electrohydrodynamic, or electrokinetic pumps. In addition, as outlined herein, portions of the internal surfaces of the device may be coated with a variety of coatings as needed, to reduce non-specific binding, to allow the attachment of binding ligands, for biocompatibility, for flow resistance, etc. These microfluidic caps can be made in a variety of ways, as will be appreciated by those in the art. See for example references described in PCT US00/10903, and references outlined therein, all of which are expressly incorporated by reference.

When the cap of the cartridge is used as part of the assay, it may be configured to include one or more of a variety of components, herein referred to as "modules", that will be present on any given device depending on its use, and are connected as required by microchannels. These modules include, but are not limited to: sample inlet ports; sample introduction or collection modules; cell handling modules (for example, for cell lysis, cell removal, cell concentration, cell separation or capture, cell growth, etc.); separation modules, for example, for electrophoresis, dielectrophoresis, gel filtration, ion exchange/affinity chromatography (capture and release) etc.; reaction modules for chemical or biological alteration of the sample, including amplification of the target analyte (for example, when the target analyte is nucleic acid, amplification techniques are useful, including, but not limited to polymerase chain reaction (PCR), oligonucleotide ligation assay (OLA); strand displacement amplification (SDA), and nucleic acid sequence based amplification (NASBA) and other techniques outlined in WO 99/37819 and PCT US00/19889), chemical, physical or enzymatic cleavage or alteration of the target analyte, or chemical modification of the target; fluid pumps (including, but not limited to, electroosmotic, electrohydrodynamic, or electrokinetic pumps; fluid valves; thermal modules for heating and cooling; storage modules for assay reagents; mixing chambers; and detection modules.

In addition, while these microfluidic components are described herein as being associated with the cap of the cartridge, as will be appreciated by those in the art, these modules and channels (as well as other components outlined herein) may be located anywhere in the cartridge or device. In addition, some components may be in the device; for example, "off chip" pumps may be located within one or more stations of the device.

The cartridge comprises at least one biochip, with some embodiments utilizing one or more biochips per cartridge.

Detection of a label indicates the presence of the target sequence. All the techniques described below rely on the formation of assay complexes on a surface, as a result of hybridization of a target sequence comprising the sequence complementary to the capture probe or the SBE probe sequence.

There are three general ways in which the assays of the invention are run. That is, the hybridization can be either direct or indirect (sandwich type). In a first embodiment, the "target sequence" or "target analyte" is labeled; binding of the target sequence thus provides the label at the surface of the solid support. Alternatively, in a second embodiment, unlabeled target sequences are used, and a sandwich" format is utilized; in this embodiment, there are at least two binding ligands used per target sequence molecule; a "capture" or "anchor" binding ligand (also referred to herein as a "capture probe", particularly in reference to a nucleic acid binding ligand) that is attached to the detection surface as described herein, and a soluble binding ligand (frequently referred to herein as a "signaling probe", "label probe", or "electron transfer moiety"), that binds independently to the target sequence, and either directly or indirectly comprises at least one label. In a third embodiment, as further outlined below, none of the compounds comprises a label, and the system relies on changes in electronic properties for detection.

In another preferred embodiment, the detection technique comprises a "sandwich" assay, as is generally described in U.S. Ser. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays are used when the target sequence does not comprise a label; that is, when a secondary probe, comprising labels, is used to generate the signal. As discussed herein, it should be noted that the sandwich assays can be used for the detection of primary target sequences (e.g. from a patient sample), or as a method to detect the product of an amplification reaction as outlined above.

A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence; and electrochemical detection that include, but are not limited to, transition metal complexes, organic ETMs, and electrodes. Detection of electron transfer is generally initiated electronically, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs (when reporters are used) and in part on the other system components, the composition and integrity of the monolayer, and what type of reference electrode is used.

In some embodiments, the detection module is configured to allow for optical detection of target sequences. Here, the detection surface may comprise any surface suitable for the attachment of capture probes described above. Generally, optical detection of target sequences involve providing a colored or luminescent dye as a 'label' on the target sequence. Preferred labels include, but are not limited to, fluorescent lanthanide complexes, including those of Europium and Terbium, fluorescein, rhodamine, tetramethylrhodamine, eosin, erythrosin, coumarin, methylcoumarins, pyrene, Malacite green, stilbene, Lucifer Yellow, Cascade Blue™. Texas Red, 1,1'-[1,3-propanediylbis [(dimethylimino-3,1-propanediyl]]bis[4-[(3-methyl-2(3H)-benzoxazolylidene)methyl]]-, tetraioide, which is sold under the name YOYO-1, and others described in the 6th Edition of the Molecular Probes Handbook by Richard P. Haugland, hereby expressly incorporated by reference.

In a preferred embodiment, the streptavidin-Alexa system is used for detection. Here, a sample is initially processed by amplification with biotinylated primers, resulting in biotinlyated amplicons. The array matrix is then contacted with these biotinylated amplicons. Hybridization of the amplicons to the oligonucleotide probes is measured by addition of Streptavidin that has been conjugated with a fluorescent dye, an Alexa dye purchased from Molecular Probes, Inc. Due to the biotin-streptavidin interaction, the dye is localized to those discrete locations of the array matrix where an oligonucleotide probe is hybridized to a biotinylated amplicon. All other locations are free of biotinylated amplicons, and thus free of the dye. The presence of dye may be detected in any of a variety of ways, and detection may be automated to allow for automated data processing.

After binding, a variety of techniques allow for the detection of radiation emitted by the fluorescent labels. These techniques include using fiber optic sensors with nucleic acid probes in solution or attached to the fiber optic. Fluorescence is monitored using a photomultiplier tube or other light detection instrument attached to the fiber optic.

In addition, scanning fluorescence detectors such as the Fluorlmager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Further, photodiodes, CCD cameras, or an active pixel system may be used to image the radiation emitted by fluorescent labels.

These methods also include time or frequency dependent methods based on AC or DC currents, pulsed methods, lock-in techniques, filtering (high pass, low pass, band pass), and time-resolved techniques including time-resolved fluorescence.

For electrochemical detection, the target sequence can comprise an electrochemically active reporter (also referred to herein as an electron transfer moiety (ETM)), such as a transition metal complex, defined below. ETMs can be attached to either nucleic acids, target sequences, or soluble binding ligands as is generally outlined in WO 98/20162, hereby expressly incorporated by reference in its entirety.

Once the assay complexes are formed, the presence or absence of the ETMs are detected as is described below and in U.S. Pat. Nos. 5,591,578; 5,824,473; 5,770,369; 5,705,348 and 5,780,234; U.S. Ser. Nos. 08/911,589; 09/135,183; 09/306,653; 09/134,058; 09/295,691; 09/238,351; 09/245,105 and 09/338,726; and PCT applications WO98/20162; WO 00/16089; PCT US99/01705; PCT US99/01703; PCT US00/10903 and PCT US99/10104, all of which are expressly incorporated herein by reference in their entireties.

The terms "electron donor moiety", "electron acceptor moiety", and "ETMs" (or grammatical equivalents herein refers to molecules capable of electron transfer under certain conditions. It is to be understood that electron donor and acceptor capabilities are relative; that is, a molecule which can lose an electron under certain experimental conditions, will be able to accept an electron under different experimental conditions. It is to be understood that the number of possible electron donor moieties and electron acceptor moieties is very large, and that, one skilled in the art of electron transfer compounds, will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinum, cobalt and iron.

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as $L_m$). Suitable nitrogen donating ligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol [3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp73–98), 21.1 (pp. 813–898) and 21.3 (pp 915–957), all of which are hereby expressly incorporated by reference.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2, 1,9-def 6,5,10-d'e'f')diisoquinoline dichloride ($ADIQ^{2+}$); porphyrins ([meso-tetrakis(N-methyl-x-pyridinium) porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5, 5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

The choice of the specific ETMs will be influenced by the type of electron transfer detection used, as is generally outlined below. Preferred ETMs are metallocenes, with ferrocene being particularly preferred.

In a preferred embodiment, a plurality of ETMs are used.

In yet another preferred embodiment Xanthon™ array technology is used. Xanthon™ technology is an electrochemical platform that directly detects target nucleic acids without the need for sample purification, amplification or the use of fluorescent, chemiluminescent or radioactive labels. This technology relies on soluble electron transfer mediators to quantitate the number of oxidizable guanine residues on a surface. That is, when a target sequence is present, the amount of guanines increases, thus resulting in an increase of electron transfer. (See e.g. An Ionic Liquid Form of DNA: Redox-Active Molten Salts of Nucleic Acids. A. M. Leone, S. C. Weatherly, M. E. Williams, R. W. Murray*, H. H. Thorp* J. Am. Chem. Soc., 2001, 123, 218–222. Mediated electrochemical detection of nucleic acids for drug discovery and clinical diagnostics. N. Popovich IVD Technology, 2001, 7, 36–42. Oxidation of 7-Deazaguanine: Mismatch-Dependent Electrochemistry and Selective Strand Scission. I. V. Yang, H. H. Thorp* Inorg. Chem., 2001, 40, 1690–1697. Oxidation Kinetics of Guanine in DNA Molecules Adsorbed to Indium Tin Oxide Electrodes. P. M. Armistead, H. H. Thorp* Anal. Chem., 2001, 73, 558–564. Proton-Coupled Electron Transfer in Duplex DNA: Driving Force Dependence and Isotope Effects on Electrocatalytic Oxidation of Guanine. S. C. Weatherly, I. V. Yang, H. H. Thorp* J. Am. Chem. Soc., 2001, 123, 1236–1237. Effects of Base Stacking on Guanine Electron Transfer: Rate Constants for G and GG Sequences of Oligonucleotides from Catalytic Electrochemistry. M. F. Sistare, S. J. Codden, G. Heimlich, H. H. Thorp* J. Am. Chem. Soc., 2000, 122, 4742–4749. Electrocatalysis of Guanine Electron Transfer: New Insights from Submillimeter Carbon Electrodes. V. A. Szalai, H. H. Thorp* J. Phys. Chem. B., 2000, 104, 6851–6859. Electron Transfer in Tetrads: Adjacent Guanines are not Hole Traps in G Quartets. V. A. Szalai, H. H. Thorp* J. Am. Chem. Soc., 2000, 122, 4524–4525. Kinetics of Metal-Mediated, One-Electron Oxidation of Guanine in Polymeric DNA and Oligonucleotides Containing Trinucleotide Repeat Sequences. I. V. Yang, H. H. Thorp* Inorg. Chem., 2000, 39, 4969–4976. Modification of Metal Oxides with Nucleic Acids: Detection of Attomole Quantities of Immobilized DNA by Electrocatalysis. P. M. Armistead, H. H. Thorp* Anal. Chem., 2000, 72, 3764–3770. Electrochemical Detection of Single-Stranded DNA using Polymer-Modified Electrodes. A. C. Ontko, P. M. Armistead, S. R. Kircus, H. H. Thorp* Inorg. Chem., 1999, 38, 1842–1846. Electrocatalytic Oxidation of Nucleic Acids at Electrodes Modified with Nylon and Nitrocellulose Membranes. Mary E. Napier and H. Holden Thorp J. Fluorescence, 1999, 9:181–186. Electrochemical Studies of Polynucleotide Binding and Oxidation by Metal Complexes: Effects of Scan Rate, Concentration, and Sequence. M. F. Sistare, R. C. Holmberg, H. H. Thorp* J. Phys. Chem. B, 1999, 103, 10718–10728. Site-Selective Electron Transfer from Purines to Electrocatalysts: Voltammetric Detection of a Biologically Relevant Deletion in Hybridized DNA Duplexes. Patricia A. Ropp and H. Holden Thorp Chem. and Biol., 1999. Electrochemical Detection of Single-Stranded DNA using Polymer-Modified Electrodes. A. C. Ontko, P. M. Armistead, S. R. Kircus, H. H. Thorp* Inorg. Chem. 1999, 38, 1842–1846. Electrocatalytic Oxidation of Nucleic Acids at Electrodes Modified with Nylon and Nitrocellulose Membranes. Mary E. Napier and H. Holden Thorp J. Fluorescence 1999, 9:181–186. Electrochemical Studies of Polynucleotide Binding and Oxidation by Metal Complexes: Effects of Scan Rate, Concentration, and Sequence. M. F. Sistare, R. C. Holmberg, H. H. Thorp* J. Phys. Chem. B 1999, 103, 10718–10728. Site-Selective Electron Transfer from Purines to Electrocatalysts: Voltammetric Detection of a Biologically Relevant Deletion in Hybridized DNA Duplexes. Patricia A. Ropp and H. Holden Thorp Chem. and Biol. 1999, 6:599–605. Cutting Out the Middleman: DNA Biosensors Based on Electrochemical Oxidation. H. H. Thorp Trends in Biotechnol. 1998, 16:117–121. Probing Biomolecule Recognition with Electron Transfer: Electrochemical Sensors for DNA Hybridization. M. E. Napier, C. R. Loomis, M. F. Sistare, J. Kim, A. E. Eckhardt and H. H. Thorp Bioconjugate Chem. 1997, 8:996–913. Cyclic Voltammetry Studies of Polynucleotide Binding and Oxidation by Metal Complexes: Homogenouos Electron-Transfer Kinetics. D. H. Johnston, H. H. Thorp* J. Phys. Chem. 1996, 100, 13837–13843. Electrochemical Measurement of the Solvent Accessibility of Nucleobases Using Electron Transfer Between DNA and Metal Complexes. D. H. Johnston, K. C. Glasgow, H. H. Thorp J. Am. Chem. Soc. 1995, 117, 8933–8937.) The aforementioned references are hereby incorporated by reference. The following U.S. Patents also describe the Xanthon™ technology and are hereby incorporated by reference: U.S. Pat. No. 6,180,346, Electropolymerizable Film, and Method of Making and Use Thereof; U.S. Pat. No. 6,132,971, Electrochemical Detection of Nucleic Acid Hybridization; U.S. Pat. No. 6,127,127, Monolayer and Electrode For Detecting A Label-Bearing Target And Method Of Use Thereof; U.S. Pat. No. 5,968,745, Polymer Electrodes for Detecting Nucleic Acid Hybridization and Method of Use Thereof; U.S. Pat. No. 5,871,918, Electrochemical Detection of Nucleic Acid Hybridization; U.S. Pat. No. 5,171,853, Process of Cleaving Nucleic Acids with Oxoruthenium (IV) Complexes.

Detection of electron transfer is generally initiated electronically, with voltage being preferred. A potential is applied to the assay complex. Precise control and variations in the applied potential can be measured via a potentiostat and either a three electrode system (one reference, one sample (or working) and one counter electrode) or a two electrode system (one sample and one counter electrode). This allows matching of applied potential to peak potential of the system which depends in part on the choice of ETMs (when reporters are used) and in part on the other system components, the composition and integrity of the monolayer, and what type of reference electrode is used.

See PCT applications WO 95/15971, PCT/US96/09769, PCT/US97/09739, PCT US99/01705, WO96/40712 and WO98/20162, all of which are expressly incorporated by reference, describe novel compositions comprising nucleic acids containing electron transfer moieties, including electrodes, which allow for novel detection methods of nucleic acid hybridization.

In a preferred embodiment, electronic detection is used, including amperommetry, voltammetry, capacitance, and impedence. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capacitance) could be used to monitor electron transfer between ETM and the electrode. Finally, any system that generates a current (such as electron transfer) also generates a small magnetic field, which may be monitored in some embodiments.

In a preferred embodiment, electron transfer is initiated using alternating current (AC) methods. Without being bound by theory, it appears that ETMs, bound to an electrode, generally respond similarly to an AC voltage across a circuit containing resistors and capacitors.

Alternatively, reporterless or labelless systems are used. In this embodiment, two detection electrodes are used to measure changes in capacitance or impedance as a result of target sequence binding. See generally U.S. Ser. No. 09/458,533, filed Dec. 9, 1999 and CPT US00/33497, both of which are expressly incorporated by reference.

In this embodiment, using a labelless system, the surface of the two detection electrodes is covered with a layer of polymer matrix.

When labels such as ETMs are not used, other initiation/detection systems may be preferred. In this embodiment, molecular interactions between immobilized probe molecules and target molecules in a sample mixture are detected by detecting an electrical signal using AC impedance. In other embodiments, such molecular interactions are detected by detecting an electrical signal using an electrical or electrochemical detection method selected from the group consisting of impedance spectroscopy, cyclic voltammetry, AC voltammetry, pulse voltammetry, square wave voltammetry, AC voltammetry, hydrodynamic modulation voltammetry, conductance, potential step method, potentiometric measurements, amperometric measurements, current step method, other steady-state or transient measurement methods, and combinations thereof.

In one embodiment of the apparatus of the present invention, the means for producing electrical impedance at each test electrode is accomplished using a Model 1260 Impedance/Gain Phase Analyzer with Model 1287 Electrochemical Interface (Solartron Inc., Houston, Tex.). Other electrical impedance measurement means include, but are not limited to, transient methods using AC signal perturbation superimposed upon a DC potential applied to an electrochemical cell such as AC bridge and AC voltammetry. The measurements can be conducted at any particular frequency that specifically produces electrical signal changes that are readily detected or otherwise determined to be advantageous. Such particular frequencies are advantageously determined by scanning frequencies to ascertain the frequency producing, for example, the largest difference in electrical signal. The means for detecting changes in impedance at each test site electrode as a result of molecular interactions between probe and target molecules can be accomplished by using any of the above-described instruments.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Human P450 SNP Assay

A list of mutations (alleles) that are of possible clinical interest in the P450 genes have been identified. The worksheet in FIG. 3A through D describes the polymorphisms (SNPs) and literature references for each of the genes that have been incorporated into the initial assay design. The P450 assay is designed to discriminate the different polymorphic states (alleles) of the selected SNPs present in a given individual DNA sample. The assay protocol can be broken down into two major process areas; target preparation and signal detection. Signal detection is accomplished through the technique known as single base extension (SBE). Target preparation is based on the specific amplification of human genome regions if interest using polymerase chain reaction (PCR) technology.

Amplification of DNA through PCR technology is highly dependent on the design of the short primer sequences used for extension and amplification. For the P450 assay, the difficulty in design of these primer sequences lies in the nature of the closely related P450 gene family. All of the P450 genes belong to a superfamily of 50+ genes and 25+ pseudogenes and may share significant levels of (regional) homology, particularly those in the same subfamily (i.e subfamily 2C contains genes 2C8, 2C9, 2C18, 2C19, etc.). Gene members in the same subfamily are located on the same chromosome and usually contain an identical number of introns and exons. The attached table illustrates the relative homology shared by the genes in the 2D6 family (see FIG. 4).

The approach to designing primers specific to only the target gene of interest has been to select regions with base pair mismatches against subfamily related genes focusing particularly at the 3' end of the primer. In this manner, both the annealing hybridization specificity and on the discrimination of the PCR polymerase which extends nucleotides from the 3' end of the primer are relied upon. Primer design was further restricted to a length greater than 19 bp and a balance in terms of GC content and Tm per pair. Whenever possible, primers have also been selected to end with an -AA-3' or -CA-3' at the 3' end to prevent primer-dimer formation. All primer candidates have been analyzed using the BLAST algorithm (homology analysis algorithm) against a compiled P450 sequence library (57 genes) to remove any potential cross-reactive primer candidates. In addition to homology analysis, the primer candidates were also screened against a database of repetitive sequences. FIG. 5 characterizes all the P450 primers currently being used for amplification.

Primers were mainly designed in the exonic regions of the gene sequences due to the principle that these areas are relatively more conserved. In many cases, the exon regions that contain discriminating mismatches were far apart resulting in amplicons varying in length from 300–6500 bp. This variance in amplicon length dictates the amplification format for long PCR conditions. Optimization of PCR conditions to reduce any non-specific products and maintain yield was focused on the following areas: annealing temperature, extension time, Mg2+ concentration, primer concentration, and enzyme concentration. The Human P450 Codelink protocol reflects the current optimal PCR conditions (see example 2 below).

The two genes, CYP2D6 and CYP2C19, are of the greatest clinical interest and also have the highest homology to its relative subfamily genes. To assess the specificity of the CYP2D6 and CYP2C19 primers, primers specific to 2D8, 2D7A, 2D7B and 2C9 were designed. Experiments were run with all the primers using genomic DNA target (to assess that the primers are working) and followed by reamplification using all the primers with CYP2D6 and CYP2C19 diluted amplicon as the target. It is assumed that if any cross species amplification was occurring in the PCR of CYP2D6 and CYP2C19, these cross products would be seen upon reamplification of CYP2D6/2C19 diluted amplicon. No evidence that cross amplification is occurring was observed with the 2D6 and 2C19 primers which lends confidence to the specificity of design.

The P450 amplicons amplified from a single DNA sample are prepared for SNP detection by combining all amplicons, purifying the pooled solution (removal of excess dNTPs and primers) and fragmenting of the PCR product. The entire protocol and process is outlined in example 2. Once the target preparation is complete, the next part of the process is signal detection via single base extension (SBE).

The detection of each single nucleotide polymorphism is accomplished via SBE of the 3' end of our probes bound to a polymer surface on the 5' end. The probes are designed in pairs with the 3' end at the SNP position or SNP+1. The perfect match to the target present will be kinetically favored during hybridization and give the most signal intensity. In the case of a heterozygote mutation, both probes in a pair will demonstrate relatively equal intensity. The quality of detection is therefore reliant on the specificity and quality of the probe design. All initial probe designs were processed using probe designing software packages, e.g., "Probe Design". The identical fixed reference sequences with the SNPs identified using IUPAC nomenclature used for primer design was used for probe design.

For each SNP, probe candidates were designed from both sequence directions, sense and anti-sense. In addition to direction, probes were designed at 2 different Tm's, 60° and 70° C. For cases where the probe sequences overlap multiple SNPs in close proximity, dITP (deoxy-inosine tri-phosphate) is used in places where a polymorphism is present on the probe at a position other than that being detected (at the 3'end). The dITP is less stringent in binding and will allow for a mismatch at that particular position.

To increase confidence in the assay analysis, 2 types of control probes were also designed. Probes to detect the successful amplification of each of the 10 unique amplicons were designed in an area on the gene sequence (covered by the amplicon) that is conserved and relatively separated from the SNPs detected. If one of these amplicon control probes (ACPs) does not yield a signal, the SNPs detected by this amplicon are masked from analysis assuming that the amplicon failed PCR. Because 2D6 contains approximately half the SNPs in this assay, psuedogene control probes (PCGs) for 2D7A, 2D7B, and 2D8 were designed to lend additional assurance that the PCR reaction is specific and mixed gene species are not present.

All of the probe candidates were passed through iterations of initial performance screening through actual chip builds and assay tests. The probes which discriminate the mutations the best were selected (sequencing data used as the gold standard). After initial performance screening, many of the probes which demonstrated signal above background due to possible self-extension were redesigned with addition of 1–2 base overhang. FIG. 6 depicts the final probe list for the current P450 assay. Performance data on the discrimination capabilities of these probes is summarized in FIG. 7.

Example 2

Human P450 Codelink Protocol: A Preferred Protocol for Running the Chips of the Invention (See FIGS. 11 to 16)

Product Description

The CodeLink™ SNP Bioarrays: Human P450 is a tool for genotyping 96 single-nucleotide polymorphisms (SNPs) related to Cytochrome P450 genes. The CodeLink SNP Bioarrays: Human P450 contains single-stranded oligonucleotide probes for a subset of seven human Cytochrome P450 genes. These genes are CYP 1A1, 1A2, 1B1, 2C19, 2D6, 2E1, and 3A4.

Four independent assays can be performed on each CodeLink SNP Bioarrays: Human P450.

Performance Specifications

This product will have a call rate of 95% with accuracy of 98%.

Storage and Handling

Upon receipt, the CodeLink SNP Bioarrays: Human P450 should be stored at room temperature in original packaging.

The Motorola SBE Kit and Uniplex PCR primer plates should be stored at −20° C.

Product use Limitations

The CodeLink SNP Bioarrays: Human P450 is for research use only and is not to be used for diagnostic purposes.

All biological specimens and materials should be handled as if capable of transmitting infection and disposed of with proper precautions in accordance with federal, state, and local regulations. These include adherence to the OSHA Bloodborne Pathogens.

Standard (29 CFR 1910.1030) for blood-derived and other samples governed by this act.

Precautions

Exercise care to avoid cross-contamination of samples, reagents and arrays during all steps of this procedure.

Avoid microbial contamination. Avoid areas of high particulate content.

Assay Protocol: Target Preparation and Single-Base Extension (SBE)

1.0 Getting Started
   1.1 Motorola Reagents/Kits
      CodeLink SNP Bioarrays: P450 Beta Kit, Motorola, Part# 20002
      Data Disk CD, Motorola, Part# 20006
      P450 Beta PCR primer plates, Motorola, Part# 30007
      SBE Kit, Motorola, Part# 20006
         Biotinylated Acyclo Terminator™ Nucleotide Mix
         SBE Buffer
   1.2 Prescribed Reagents/Kits
   Roche Biochemicals
      PCR-Grade Deoxy-Nucleotide Set, Roche Biochemicals, Part# 1969064
   Applied Biosystems
      GeneAmp® XL DNA Polymerase (contains 3.3×XL Buffer, 25 mM Magnesium acetate (Mg(OAc)$_2$), Applied Biosystems, Par# N808-0187 [400 units] or Part# N808-0188 [2400 units]
   Life Technologies, Inc. (LTI)
      DNase I Amplification Grade (1U/µL) shipped with DNase I 10× Buffer, LTI, Part# 18068-015
      Ultrapure ddH$_2$O (Nuclease free), Life Technologies, Inc. (LTI), Part# 15230-170
   Aldrich
      Ethyl alcohol, anhydrous 99.5+%, Aldrich, Part# 15, 190-4, or equivalent
   Qiagen
      QIAquick™ 8 PCR Purification Kit, Qiagen, Part# 28142
   Amersham
      Thermo Sequenase™ (Enzyme only), Amersham, Part# E79000Y [1000 units] or Part# E79000Z [10,000 units]
   Sigma
      1 M Tris-Hcl pH 7.6 stock solution, Sigma, Part# T2788
      5 M sodium chloride solution, Sigma, Part# S5150
      20×SSC, Sigma, Part# S6639
   Molecular Probes
      Streptavidin, Alexa Fluor® 532 conjugate, Molecular Probes, Part# S-1 1224
   Fisher
      Tween 20 (polyoxyethylfenesorbitan monotaurate) enzyme grade, Fisher, Part# BP337-100
   1.3 Genomic DNA (gDNA) Sample Quality
      The sample genomic DNA (gDNA) should be at a concentration of 0.450 mg/mL to 0.300 mg/mL. The recommended buffer is 10 mM Tris, 1 mM EDTA, pH 8.0. The OD 260/280 should be between 1.71 and 1.79 and protein concentration should be less than 0.9 mg/mg DNA.
   1.4 Supplies Required
   Wire slide rack, VWR, Part# 25461-014, or equivalent
   Microcentrifuge
   1.7 mL microcentrifuge tubes and racks
   Solution basis, 55 mL, sterile, VWR, Part# 21007-972, or equivalent
   Micropipettors (2 µL, 20 µL, 200 µL, 1000 µL)
   Sterile aerosol resistant pipette tips
   Wide orifice tips, Rainin, Part# HR250W
   MicroAmp® Clear Adhesive Plate seals, Applied Biosystems, Part# 4306311
   15 mL Falcon tubes, VWR, Part# 21008-918, or equivalent
   96-well collection microplates RB, Qiagen, Part# 19581
   0.2 mL 96-well plate, Marsh Bio Products, Part# T0296PE
   Chamber removal fixture, Motorola, Part# 100017
   Powder-free gloves
   slide storage box
   1.5 Licenses Required
   License to practice PCR from Applied Biosystems or Hoffman-LaRoche and F. Hoffman-LaRoche Ltd.
   1.6 Instruments Required
   Thermal cycler, Applied Biosystems GeneAmp® PCR System 9700, Part# N805-0001
   96-well plate clinical centrifuge, Qiagen, Part# 81010
   QIAvac 6S, Qiagen, Part# 19503
   QIAvac plate holder, Qiagen, Part# 19548
   Filtered ddH$_2$O source, Barnstead or equivalent
   Hybaid Omnislide Thermal Cycler, Motorola, Part# 600002

Hybaid Omnislide Wash Module, Motorola, Part# 60003
Hybaid Ambient Rack, Motorola, Part# 600074
GenePix™ 4000 Axon Scanner, Motorola, Part# 600000
Computer, Motorola, Part# 600001
CodeLink™ System Software:
  Analysis, Motorola, Part# 20004
  Scanning, Motorola, Part# 200003

1.7 Reagent Preparation

The following reagents should be prepared before beginning the assay, with the exception of the Staining Solution.

Target Preparation Reagents

Water used in all target preparations should be Ultrapure ddH$_2$O (nuclease free) from LTI.

2.5 mM dNTP solution
  Using the PCR-grade deoxy-nucleotide set, make 20 mL of solution using the following:
  0.5 mL 100 mM dTTP
  0.5 mL 100 mM dATP
  0.5 mL 100 mM dGTP
  0.5 mL 100 mM dCTP
  18 mL of ultrapure ddH$_2$O
  Divide into 5, 4 mL aliquots and store dNTP mix at −20° C. in 15 mL tubes.

PCR Master Mix
  To make 41 mL (sufficient for 1000 PCR reactions or 83 samples):
  20.0 mL ultrapure ddH$_2$O
  15.0 mL GeneAmp XL 3.3× Buffer II (Vortex before use)
  2.0 mL Mg(OAc)$_2$
  4.0 mL 2.5 mM dNTP solution
  Divide into 5, 8 mL aliquots and store at −20° C. (there will be 1 mL excess).

DNase 1× Buffer
  To make 1 mL:
  900 µL ultrapure ddH$_2$O
  100 µL DNase 10× Buffer
  Store at −20° C.

Diluted Genomic DNA (gDNA)
  To make 60 µL:
  58 µL ultrapure ddH$_2$O
  2 µL gDNA Post Reaction Processing Reagents To make 1 L Washing Solution:
  Add 250 mL of 20×SSC to 750 mL of filtered ddH$_2$O. Mix well. Store at room temperature and preheat in Hybaid Omnislide Wash Module to 60° C. before use.

To make 1 L Staining Diluent:
  Combine 918 mL of filtered ddH$_2$O with 30 mL of 5 M NaCl and 50 mL of 1 M Tris-HCl pH 7.6. Add 2 mL of Tween 20 and mix well. Store at room temperature.

To make 2 mLs of Streptavidin Alexa Diluent:
  Combine 100 µL of 1 M Tris-HCl pH 7.6 with 60 µL of 5 M NaCl and 1840 µL of ultrapure ddH$_2$O.

To make 1 mL Streptavidin Alexa-Fluor 532 conjugate:
  Add one mL of Streptavidin Alexa diluent to a vial containing crystalline Streptavidin Alexa-Fluor 532 conjugate. Mix well by inversion and store at 4° C., protected from light.

To make Staining Solution:
  Prepare immediately prior to use.
  Determine the volume of staining solution needed based on the number of slides being processed (300 mL for 1–10 slides, 600 mL for 11–20 slides). For 300 mL of staining solution, mix 300 µL of Streptavidin Alexa-Fluor 532 conjugate solution with 300 mL of staining diluent. For 600 mL of staining solution, mix 600 µL of Streptavidin Alexa-Fluor 532 conjugate solution with 600 mL of TNT. Mix well by inversion.

To make 1 L Destaining Solution:
  Combine 870 mL of filtered ddH$_2$O with 30 mL of 5 M NaCl and 100 mL of 1 M Tris-HCl pH 7.6. Mix well and store at room temperature.

1.8 Instrument Preparation

Refer to the original manufacturer's user manual for specific instructions.

Thermal Cycler GeneAmp 9700

Enter the following PCR program into the thermal cycler:
  a. 94° C. for 1:00 minute
  b. 94° C. for 0:30 minutes
  c. 68° C. for 4:00 minutes
  d. Repeat b and c, 29 times for a total of 30 cycles
  e. 72° C. for 10:00 minutes
  f. 4° C. Forever Program will end automatically after it completes the last step entered.

Save program as "PCR".

Thermal Cycler GeneAmp 9700

Enter the following program for DNase target fragmentation into the thermal cycler:
  a. 37° C. for 10:00 minutes
  b. 95° C. for 10:00 minutes
  c. 4° C. Forever Program will end automatically after it completes the last step entered.

Save program as "Fragment".

Hybaid Omnislide Thermal Cycler

Choose the simulated slide program type and enter the following SBE reaction program into the thermal cycler:
  a. 85° C. for 1:00 minute
  b. 85° C. for 0:30 minutes
  c. 60° C. for 10:00 minutes
  d. Go to step b for 7 more cycles for a total of 8 cycles.

Program will end automatically after it completes the last step entered.

Save program as "01" when prompted.

2.0 Target Preparation 2.1 PCR Reactions

For each sample 45 µL of gDNA at approximately 10 ng/µL will be necessary.

Each primer plate will accommodate 8 samples at 12 PCR reactions per sample.
  1. Prepare the reaction mix for each sample in a new 1.7 mL microcentrifuge tube using the appropriate volumes (Table 1).
2. Aliquot 45 µL of reaction mix into each well of the 12 well layout in the primer plate allocated for each sample (FIG. 12).
3. Seal plate with a new Applied Biosystems adhesive plate seal.
4. Spin in centrifuge for 1 minute at 1000 rpm.
5. Immediately place plate in GeneAmp PCR System 9700. Run program "PCR" entered in section 1.8.

TABLE 1

PCR reaction mix set-up for each sample.

| Reagent | Volume for 1 PCR reaction | Volume for 12 PCR reactions w/Excess |
|---|---|---|
| PCR Master Mix | 41.0 μL | 615.0 μL |
| GeneAmp XL enzyme | 1.0 μL | 15.0 μL |
| gDNA (10 ng/μL) | 3.0 μL | 45.0 μL |
| TOTAL | 45.0 μL | 675.0 μL |

2.2 PCR Pooling and Purification

Use the QIAquick 8 PCR Purification Kit to remove primers and nucleotides from the PCR reactions according to the following protocol:
1. Remove plate from the thermal cycler within 12 hours of PCR program completion.
2. Pool each sample's PCR reactions (12) into separate new 15 ml conical tubes for each sample. (Total volume=600 μL in each tube).
3. Add 3,000 μL of PB buffer provided in kit to each of the 15 mL tubes containing pooled target. Mix well by vortexing.
4. Place a new QIAquick 8-well strip on the QIAvac 6S vacuum manifold without a collection plate.
5. Pipet entire contents of one 15 mL conical tube (3600 μL at a time 9600 μL at a time) into one of the wells of the QIAquick 8-well strip under house vacuum (150 mbar).
6. Repeat for 7 other sample tubes.
7. Add 1 mL of PE buffer provided in kit to each well containing sample.
8. Repeat PE buffer addition for a total of 2 mLs per well.
9. Turn off house vacuum.
10. Remove the 8-well QIAquick trip and smack and dab on a stack of paper towels to remove excess PE buffer.
11. Replace the 8-well QIAquick strip on the manifold and apply house vacuum for 5 minutes to dry columns. Remove cover.
12. Place a new QIAquick collection plate on the plate holder and insert under the 8-well QIAquick strip. Replace cover.
13. Add 40 μL of DNase 1× Buffer to the center of each QIAquick well and incubate at room temperature for 1 minute.
14. Turn on house vacuum for 1 minute to collect purified PCR product in the collection plate.

NOTE: Do not use the provided EB buffer for elution.

2.3 DNA Fragmentation

Digest the PCR products according to the following protocol:
1. Transfer each well of purified PCR product from the QIAquick collection plate into a new 0.2 mL Marsh 96-well plate maintaining the integrity and identity of the individual samples.
2. Make fresh 1:300 dilution of DNase I in DNase 1× Buffer.
3. Add 10 μL of diluted DNase I to each well containing purified PCR product.
4. Immediately, place the 0.2 mL PCR 96-well plate onto the thermal cycler and run the "Fragment" protocol programmed in section 1.8.

NOTE: DO NOT use EDTA to stop the fragmentation; the enzyme is heat-killed during thermal cycling.

The samples are now ready for immediate use in the SBE reaction, or store samples at −20° C. in a seated plate until ready for the SBE reaction.

3.0 SBE Reaction

A maximum of 16 slides can be run on the Hybaid Omnislide thermal cycler at one time.

3.1 Prepare SBE Reaction Master Mix
1. Thaw all reaction components (except enzyme) at room temperature. This includes PCR products (if frozen above), 10× Nucleotide Mix, SBE Buffer, and ultrapure ddH$_2$O.
2. When reagents are completely thawed, vortex each thoroughly and spin for 15 seconds in the microcentrifuge before preparing the reaction mix.
3. Prepare the SBE Reaction Master Mix with the appropriate volumes (except enzyme) in a new 1.7 mL microcentrifuge tube (Table 2). Adjust volumes based on the total number of arrays being run. (A maximum of 28 arrays can be prepped in one 1.7 mL tube.)
4. Remove the enzyme from the freezer and add the appropriate volume (Table 2). Mix well by pipetting.
5. Immediately return all reagents to −20° C.
6. Gently vortex the tube after the addition of all reagents. Spin in the microcentrifuge for 15 seconds to consolidate sample and to remove any bubbles or foam.

TABLE 2

Master mix set-up SBE reaction.

| Reagent | 1 Array | 4 Arrays W/Excess |
|---|---|---|
| Motorola SBE Buffer | 8.0 μL | 35.2 μL |
| 10X Nucleotide Mix | 4.0 μL | 17.6 μL |
| Water | 0.77 μL | 3.39 μL |
| Thermo Sequenase | 0.23 μL | 1.01 μL |
| TOTAL | 13.0 μL | 57.2 μL |

3.2 Prepare Individual SBE Reactions
1. After mixing and spinning, transfer 13 μL of the SBE reaction master mix to each clean, labeled microfuge tube (FIG. 13).
2. Add 27 μL of the purified PCR target to each tube.

3.3 Load Reaction Mixtures into Flex Chambers

The time between loading of flex chambers and placement on the thermal cycler should not exceed 45 minutes. The slides should not be placed on ice at any time.
1. For each flex chamber, aspirate 40 μL of reaction mixture in a wide orifice tip (making sure there are no bubbles in the tip).
2. Place the pipette tip at a 90° angle over the appropriate array port and apply downward pressure until the tip forms a seal with the adhesive on the port. (FIG. 14.) This will minimize leaking outside of the port and reduces the risk of blocking the introduction channel.
3. WITHOUT using the blowout feature of the pipettor, slowly eject the sample out of the tip and into the array chamber. You will see the fluid moving across the array area. Use smooth, even pressure to maintain a uniform rate during filling.
4. After fluid has completely filled the chamber and a slight excess has appeared in the opposite port, maintain pressure and remove the pipette tip from the input port.

5. After filling a flex chamber, check for the presence of air bubbles. If there are any large (>1.5 mm) bubbles present or if any bubbles appear in the center of the array, the array cannot be used. Small bubbles near the ports should not affect performance.
6. Repeat this loading procedure using fresh tips with the other array chambers and slides.

NOTE: Do not attempt to withdraw fluid from flex chamber in the event of misloading.

3.4 Seal Flex Chambers
1. After all flex chambers on each slide have been loaded, they are ready for sealing.
2. Select a pre-cut sealing strip and remove the backing using forceps to expose the adhesive. Handling carefully, apply the strip to the edge of the slide near one end. Slowly place the strip so that it covers all four ports on one side of the slide (FIG. 15).

NOTE: Adhesive will become firmly attached at first contact with the chamber. Use caution to ensure that the sealing strip is in the proper orientation before placing it on the chamber. Do not attempt to remove a misaligned sealing strip. Instead, place a second strip to cover any open ports.

3. Repeat the application of a second strip to cover the remaining 4 ports and for each slide until all ports are sealed.
4. When all strips have been applied, ensure that each port is sealed securely by pressing firmly on the strips. Be careful not to apply pressure over the array itself as this may cause volume loss.

3.5 Thermal Cycling
1. Add 50 mL of filtered ddH$_2$O to the plastic chamber surrounding the heat blocks of the Hybaid Omnislide thermal cycler.
2. Place each loaded and sealed slide (flex chamber acing up) onto the heat blocks. Do not use the rack normally used for this step. Lay the slides directly on the heat blocks, 8 slides per block. (FIG. 16.)
3. Place the cover over the heat blocks and secure by turning the lock tabs.
4. Press the "Menu" button on the Omnislide control panel. Select "Run" from the menu and then press "Enter".
5. Enter program "01" (programmed in section 1.8). Once you have selected the "01" program, press the "Enter"button.

NOTE: The appropriate calibration factor of 100 will be displayed after the "Enter" button is pressed.

4.0 Post-Reaction Slide Processing
For the post-reaction slide processing steps, the volume of each solution used is dependent on the number of slides being processed. For 1–10 slides, use 300 mL of the designated solution. For 11–20 slides, use 600 mL of the designated solution.

NOTE: Between every step, the Hybaid wash station sleeves should be rinsed with filtered ddH$_2$O three times.

4.1 Prepare Hybaid Wash Station
NOTE: Two sleeves and one rack for the Hybaid washer will be necessary for slide processing.
1. Fill Sleeve 1 with the appropriate volume of preheated Washing Solution. Place the sleeve in the station and set the temperature to 60° C.
2. Take Sleeve 2 and a rack to the sink with filtered ddH$_2$O source and fill the sleeve with the appropriate volume.

4.2 Remove Flex Chambers
1. Remove the slides from the thermal cycler within 15 minutes of program completion.

NOTE: DO NOT ALLOW THE SLIDE TO DRY DURING THIS PROCESS. If drying is noticed, make a notation of the occurrence as it may lead to an increase in background noise.

2. Take the slides to the sink where your rack and sleeve are located. Turn on the filtered ddH$_2$O source. (A 500 mL squirt bottle filled with filtered ddH$_2$O can also be used.)
3. Wearing powder-free gloves, place a slide in the chamber removal fixture. Grasp the removal tab portion of the flex chamber and, while holding the slide securely, slowly pull back the flex chamber tab until the first array area is exposed.
4. Immediately rinse the exposed array area with filtered ddH$_2$O to rinse away the SBE reaction solution by holding the chamber removal fixture in the filtered ddH$_2$O stream.
5. After the first array has been rinsed, continue to pull back the flex chamber tab until the second array is exposed and then immediately rinse it with filtered ddH$_2$O.
6. Repeat this process until four arrays are sequentially exposed and rinsed as quickly as possible. This minimizes the risk of cross contamination between arrays.
7. After the flex chamber has been removed, rinse the entire slide with filtered ddH$_2$O, then quickly place it into a slot in the Hybaid rack and immediately submerge the rack into the sleeve of filtered ddH$_2$O (Sleeve 2).
8. Repeat this process for each slide until all the slides have had their chambers removed and been placed in the rack.

NOTE: The first slides will be submerged in filtered ddH$_2$O while subsequent slides have their chambers removed.

4.3 Wash and Rinse Slides
1. Place the rack containing slides from the sleeve with filtered ddH$_2$O (Sleeve 2) into the preheated sleeve (Sleeve 1) containing Washing Solution in the wash station.
2. Allow the slides to incubate for 30 minutes at 60° C. During this time, open the wash sleeve and gently agitate the Washing Solution by moving the rack up and down 5 times within the sleeve every 10 minutes.
3. Rinse and fill Sleeve 2 with the appropriate volume of filtered ddH$_2$O. When the incubation is complete, transfer the rack from the Washing Solution (Sleeve 1) to the filtered ddH$_2$O (Sleeve 2).

CAUTION: The rack and Washing Solution will be HOT, handle with care.

4. Using both sleeves and rinsing between uses, rinse the rack of slides in filtered ddH$_2$O two additional times with agitation. Leave the rack in the last filtered ddH$_2$O rinse in the sleeve.

While the slides are incubating in the Washing Solution, prepare the appropriate amount of Staining Solution using the dilution instructions in section 1.7.

4.4 Stain Slides
NOTE: Staining Solution should be prepared fresh for each batch of slides being processed.
1. Fill the available sleeve (Sleeve 1) with the appropriate amount of Staining Solution.

2. Transfer the rack from the last filtered ddH₂O wash to the sleeve with the Staining Solution.
3. Place sleeve 1 (containing rack and Staining Solution) in the NON-heated slot on the wash station.
4. Allow the slides to incubate in the Staining Solution for 30 minutes at room temperature. During this time, open the wash sleeve and gently agitate the Staining Solution by moving the rack up and down 5 times within the sleeve every 10 minutes. While the slides are incubating in the Staining Solution, prepare the appropriate amount of Destaining Solution using the dilution instructions in section 1.7.

4.5 Destain Slides
1. Fill the available sleeve (Sleeve 2) with the appropriate amount of Destaining Solution.
2. When the slides have completed the incubation described in section 4.4, remove the sleeve and take it to the sink.
3. Transfer the rack from the Staining Solution to the sleeve with the Destaining Solution.
4. Place the sleeve (containing rack and Destaining Solution) into the NON-heated slot on the wash station.
5. Incubate the slides at room temperature for five minutes and repeat one additional time with fresh Destaining Solution (Sleeve 1).

4.6 Rinse Slides
1. After the last incubation in the Destaining Solution, remove Sleeve 1 and take it to the sink.
2. Fill the available sleeve (Sleeve 2) with the appropriate amount of filtered ddH₂O. Transfer the rack from the Destaining Solution (Sleeve 1) to the filtered ddH₂O sleeve (Sleeve 2).
3. Fill a 1 L graduated cylinder with the appropriate amount of filtered ddH₂O.
4. Holding the rack, decant the filtered ddH₂O. Immediately refill the sleeve with water from the cylinder making sure that all slides are completely covered.
5. Repeat the decant and refill process three additional times using filtered ddH₂O. Leaving the rack in the last filtered ddH₂O rinse.

4.7 Dry Slides
1. Carefully remove a rinsed slide from its slot in the wash rack. Replace the wash rack in the filtered ddH₂O filled sleeve.
NOTE: Slides should be handled by their label ends or edges only. The wet polymer substrate is fragile and easily damaged.
2. Allow the slides to air-dry. If available, a dry stream of clean nitrogen (no oil) can be blown over the surface to facilitate drying. To avoid damage to the wet polymer, keep the nitrogen source at least 6 inches away from the slide surface. When the slide is dry, place it in the wire slide rack.
3. Repeat drying procedure for each slide.
4. When all slides are dry, inspect them individually. There should be no sign of salt crystals or water spots. If there are salt crystals or water spots, rinse the individual slide with filtered ddH₂O and dry.
5. Store the slides in a slide storage box.
6. Scan the slides using the Genepix 4000 Axon Scanner. Set the wavelength at 532 nm and the PMT at 430 following the CodeLink System Software for Scanning User Manual.

Example 3

Probes with Multiple Base Additions

Target-independent self extension through stem-loop forming probes that result in false-positives have been discussed. The intensity of the signal is roughly proportional to the stability of the stem-loop structure. A survey of about 500 probes indicated that about 15% show a self-extension signal. Several examples of probe sequences that self extend are shown in FIG. 18. In most cases the base incorporated is the one predicted by the template sequence immediately downstream of the stem-loop structure; this result strongly suggests that the DNA polymerase is extending the duplex formed by the stem-loop structure. Generally, a stem of three or more base pairs is required for self-extension.

The present invention describes a simple strategy in which one or more bases are added to the 3' end of the probe that self-extends (see FIG. 17). The probes used herein are novel in that the additional bases are not self-complementary within the probe but are complementary to the target. When such an additional base(s) is/are added, it creates a mismatch along the stem-loop structure and hence, the DNA polymerase does not extend the self annealed probe and hence no false positive detection occurs resulting in correct detection of the SNP base.

Target dependent extension is not affected by the additional base(s) added to the probe because the additional bases are complementary to the target. In practice adding four or more bases is not feasible. The SNP base will be too far upstream of the 3' end of the probe and a mismatch will create an internal bulge. If the short duplex downstream of the internal bulge is extended by the polymerase, the mismatch will not be detected.

All experiments were done with the DNA microarrays described in examples 1 and 2. The probes are polynucleotides (generally from 10–40 nt in length) attached at the 5' end to a support material on the slide. The SBE reaction consists of buffer, hapten-labeled acyclo terminator nucleotides and DNA polymerase. Target (PCR amplified genomic DNA containing the SNP of interest) were either added or not, to the reaction.

FIG. 19 shows the SBE assay results for a probe that shows strong self-extension in the absence of target. When a single base is added to the 3' end of the probe, the target-independent signal is significantly reduced. The target-dependent signal was not altered indicating that the probe functions properly in the presence or absence of target. The addition of two or more bases created new stem-loop structures; these probes show strong target-independent signal as expected. FIG. 20 shows the overall performance of a set of rescued probes for the P450 gene. Of the 35 probe sets that made incorrect calls, 26 (66%) sets repaired by adding one or two bases to the probe called correctly 100% of the time.

Example 4

Probes with Modified Nucleotides

Single Base Extension (SBE) assay and self extending probe problems have been explained (FIG. 2). Here, we present a set of modified bases, when incorporated into a probe, inhibits it from folding and/or forming a stable secondary structures (FIGS. 21 and 24). The modified base does not form a stable base-pair with itself but individual bases hybridize well with natural DNA/RNA bases to form non-natural base-pairs that are very stable. Such a base-pair (FIGS. 22, 23, 25 and 26) thermodynamically destabilizes a self-folded structure but has minimal affect on the stability of a probe-target duplex. Thus, they selectively inhibit the formation and/or extension of self-folded molecules.

An example base-pair is drawn in FIG. 22. Such molecules have been used in the prior art to generate selectively binding oligo pairs (U.S. Pat. No. 5,912,340 and PCT WO9712896; Kutyavin I V, Rhinehart R L, Lukhtanov E A, Gorn W. Meyer R B Jr., Gamper H B Jr. *Biochemistry* 1996) 27:35(34):11170–6; Woo J, Meyer R B Jr., Gamper H B., *Nucleic Acids Res.* (1966) 1:24(13):2470–5; 3; Compagno, D, Lampe J N, Bourget C, Kutyavin I V, Yurchenko L, Lukhtanov E A, Gorn W, Gamper H B Jr., Toulme J J., *J Biol Chem* (1999) 19:274(12)8191–8).

Self-folded structure may also be destabilized by using only one of the two bases in the base-pair, which would decrease the stability of both the self-folded molecule as well as the probe-target duplex. In that case, the melting temperature of the self-folded structure can be lowered substantially more than that of the probe-target duplex. Some example base-pairs/bases that can have such an effect include but are not limited to a) 2-amino-A:2-thio-T, b) 2-aminipurine:2-thio-T, c) 6-thio-G, d) 2-thio-C, e) hydrophobic bases such as 4-methylindole, difluorotoluene, etc. (Moran, S, Ren R X, Sheils C J, Rumney S 4th, Kool E T, *Nucleic Acids Res* (1966) 1:24(11):2044–52), 4-thio-T (FIG. 22).

Some solutions to the primer-dimer issues can also be applied to the self-folding issue. For example, a set of oligonucleotides carrying analogs of natural bases, which have a modification at the exo-cyclic amine positions (FIG. 23), are also inhibited from self-base-pairing (U.S. Pat. No. 6,001,611, PCT WO 00/06779). This kind of base can also be used in the same fashion as described in FIG. 21.

Another way of suppressing the signal from self-folded structures is by extending only the probe-target duplexes. This can be achieved by using certain modifications in the probe molecules that are not replicated by DNA polymerases (FIG. 24). That way, only the natural, target strands are used as templates, and thus extended, by the polymerases. There are a few known examples of such modifications known in literature (see above and U.S. Pat. No. 6,001,611; Stump M D, Cherry J L, Weiss R B., *Nucleic Acids Res.* (1999) 1:27(23), 4642–8). Again, such modifications have been previously used only for the primer-dimer issues and not the kind of applications proposed herein. For example, a hydrophobic base, 4-methylindole, when present in a DNA template, terminates the DNA polymerization at that site. This base has been called a "terminator". Incorporation of 2'-O-methyl RNA nucleosides has also been shown to inhibit DNA polymerization at the residue sites. It is proposed that these types of "terminator" bases and nucleosides can also be used to prevent extension of self-folded molecules, thus selectively enhancing the signal from probe-target duplexes (FIG. 25).

Experiments were carried out on the DNA microarrays described above using our standard SBE Assay, to test these hypotheses. Probes containing either no modification or with modified bases discussed above were obtained from Operon and attached to gel-slabs using amino-NHS ester chemistry (Gen3 chemistry). Sequences of the probes used are shown on top of each graph (FIGS. 27–29). All data is from slides run in Ti chambers, standard SBE CYCLE parameters, 4 TAMRA nucleotides, Tris-HCl pH8.5 plus 10 mM Kcl (buffer), no DMSO. When present, target was used at 10 ng per array at 60 ul volume. Data is summed from 8 arrays for "without target" assays and 7 arrays for "with target" assays.

Results are shown in the following graphs (FIGS. 27–29) and clearly show that incorporation of such modifications increases the signal in the presence of target v/s in the absence of target many fold, proving that the hypotheses worked as intended. Thus, a signal from a self-extending probe in the presence of target is only three-fold higher than in the absence of target (R=3.18). But, when an A:T base-pair in the step-loop is replaced with its modified analog base-pair X:Z, this ratio is increased to almost 10-fold (FIG. 27). This clearly shows that the modified base-pair is having the intended effect. Placement of the modified base-pair closer to the extension site (3'-end) can have an even more dramatic impact. Similarly, when adenosine immediately adjacent to the stem-loop is replaced with its "terminator-type" analog 4-methylindole, the signal increases from 3-fold to almost 5-fold (FIG. 27).

In FIG. 28 a signal with a self-extending probe in the presence of target is only three-fold higher than in the absence of target (R=2.42). But, when either one or both of A:T base-pairs in the step-loop are replaced with their modified analog base-pairs X:Z, this ratio is increased to almost 5-fold. This clearly shows that the modified base-pair is having the intended effect. FIG. 29 shows similar results with three different probe sequences.

Example 5

Probes with a Modified Stem that Inhibits Extension Enzyme Binding for Hairpin Structures Non-specific incorporation of nucleotides due to hair-pin loop structures or palindromic sequence, in the absence of target DNA, can often lead to false positive results in the single base extension assay. Here, by altering the affinity of the enzyme to bind to the "stem" region of the capture probes, non-specific nucleotides incorporation in the absence of target DNA can be reduced or eliminated (FIGS. 30 and 31). Modifications include but are not limited to, phosphorothioate, phosphoramidate, chiral phosphodiester analogues and methyl phosphate on the "stem" region of the capture probe. The phosphate in the nucleic acid plays a crucial role in the nucleic acid-protein interaction. The electrostatic interactions between the positively charged amino acid and the negatively charged phosphate backbone, and formation of hydrogen bonds between the phosphate oxygen and protein contribute to the binding affinity and specificity of the enzyme (FIG. 32B (a)).

By modifying the phosphate or the sugar ring at the "stem" region, we can decrease the binding affinity of the enzyme reducing the probability of non-specific nucleotides incorporation. Since modifications are not performed at the base, thermodynamic duplex stability between the capture probe and the target has not been altered (FIGS. 30 and 31).

Several modifications are proposed but are not limited to those. Phosphorothioate (sulfur substitution) and phosphoroamidate (nitrogen substitution) can alter the charge distribution, hydrophobicity and the ability for the enzyme to form an efficient hydrogen bond to the phosphate backbone. Methyl phosphonate and methyl phosphate eliminate the phosphate charge altogether, which can inhibit the enzyme to bind to the DNA (see FIGS. 32A and 32B(b to d)).

Other modifications on the sugar ring can also be introduced such as the 2' O-methyl RNA and LNA.

Example 6

Use of Inhibitory Oligonucleotides to Prevent Self-extension

The invention makes use of complementary short oligonucleotides that create a blunt end on the probe oligonucleotides and prevent generation of false signals that are generated by enzymatic self-extension of probes. The signal of interest is only created in the presence of target and all other times the signal remains in the off mode (see FIG. 33). Short complementary APO E321.T.A oligo to APO E321.T.A SNP probe can inhibit APO E321.T.A SNP probe self-extension. APO E321.T.A. probe (5'TACACTGCCAGGCA 3' (SEQ ID NO:274)) is a strong self-extender producing strong self-extension false signal under all conditions. The assay used for these studies was the modified SBE assay by using genome-wide single strand RNA as targets for SBE reaction.

Example 7

Combination of Technologies and use of Modified Reverse Transcriptase to Prevent Self-extension The invention is based upon a novel method (comprising three different technologies) which allows genome-wide SNP genotyping without multiple PCRs, without RCA (or other signal amplification technologies), and without problems from primer extension. The method involves performing a PEP (primer extension preamplification) reaction (known in U.S. Pat. No. 6,183,958; Zhang et al., Proc. Natl. Acad. Sci. 89:5847–51 (1992); Casas and Kirkpatrick, Biotechniques, 20: 219–25 (1996)) with random primers to amplify the genomic DNA in one reaction, followed by an in vitro transcription (IVT) reaction (if one of the primers had a polymerase promoter sequence). The product, cRNA, is hybridized and the probe is extended using a reverse transcriptase (RT). This would serve the same purpose as PCR of individual SNP loci in the sense that we would be reducing the complexity of the genome through the PEP and amplifying the target with the IVT. Thus, one target prep is performed for all of the SNP loci (as we do in the expression assay). Finally, the use of a modified RT (in which the DNA-dependent DNA polymerase activity has been eliminated) will mean that self-extenders will not be extended by the RT because these are DNA-dependent extensions and only probe bound to RNA targets will be extended because these rely on the RNA-dependent DNA polymerase activity (see FIG. 34).

This disclosure presents a novel methodology for SNP genotyping which does not require multiplexed PCR or thousands of PCR reactions. Furthermore, self-extension problems would not be evident because these self-extenders would not be extended by an RT which only has RNA-dependent DNA polymerase activity.

The technical feasibility of the approach has been demonstrated in three separate pieces. The feasibility of a primer extension preamplification (PEP) has been demonstrated in many molecular biology labs. The feasibility of an IVT has been demonstrated. The feasibility of an RT extending oligo probe on arrays after hybridization to RNA targets has been demonstrated (Pastinen, T., et al., (2000) Genome Research, 10:1031–42).

This method is differentiated from other methods in that all three technologies for uniplexed target prep and primer extension are combined which should not be complicated by self-extension problems that other primer extension technologies are subject to.

The novelty of the approach is based on the fact that we are using a modified RT to direct only RNA-dependent DNA polymerase activity and the fact that we are combining PEP and IVT for a new method of uniplexed target prep and applying this on oligonucleotide arrays for primer extension.

Strategic benefits are cost reduction in PCR, competitive advantages of a uniplexed target prep, discrimination, and better data reliability due to the elimination of self-extension.

Methodology

Step 1

Primer Extension using human genomic DNA and primer RRNOT7, which was designed to have 8 degenerate nucleotides at the 3' end and a T7 RNA polymerase sequence at the 5' end. It had the sequence GGCCAGTAATTG-TAATACGACTCACTATAGGGAGGCG-GNNNNNNNCGAGA (SEQ ID NO:275). Primer extension with this primer should result in fragments of human DNA with T7 RNA polymerase sequences on the 5' ends. The assay was performed with 2 ug of human genomic DNA, and 5 U of Amplitaq DNA polymerase, and 100 ng of RRNOT7 primer using PCR Amplification Buffer I (Perkin Elmer) in a final volume of 60 ul. The reaction was run for 50 cycles at 92 C, 1', 37 C 2', with a slow ramp of 10 sec/degree to 55 C for 4'.

Step 2

In vitro Transcription using these standard conditions: A total of 325 ug of cRNA was obtained from 2 ug of starting human genomic DNA. The cRNA was quantitated using UV absorbtion, and visualized on an agarose gel.

Step 3

The following oligonucleotides were diluted to 18 uM, and manually spotted on blank Surmodics slides. The first is a non-self-extender, whereas the second is a self-extender, since it loops back on itself.

| | |
|---|---|
| GTTCTTAATTCATAGGTTGCAATTTTA | (SEQ ID NO:276) |
| GCTT<u>CGAG</u>TACGACGACCCTCG | (SEQ ID NO:277) |

Slides were blocked and processed according to the standard Surmodics protocol. Additionally, a bacterial oligonucleotide, YJEK, was also spotted and process on blank Surmodici slides, to serve as a negative control.

Step 4

25 ug of cRNA were hybridized per oligonucleotide spot, in 50% formamide, 2×SSPE, at 37 C in a humidity chamber overnight (18 hrs). Slides were washed and dried.

Step 5

Each hybridized probe was extended in situ using rTth RNA-dependent DNA polymerase (Perkin Elmer), in the presence of Mn2+ and cy5-dUTP, in a final volume of 20 ul, at 50 C, for 5'. Slides were washed, dried and scanned on an Axon scanner, using the Cy5 channel (635 nm) at 600 PMT.

Results

After performing this assay in the presence of rTth, a modified reverse transcriptase which only extends DNA off an RNA template in the presence of $Mn^{2+}$ ions, self-extension is not observed off an SNP oligonucleotide which normally self-extends (see FIGS. 35 and 36).

REFERENCES

The following references are hereby incorporated by reference in their entirety.

1. Kutyavin I V, Rhinehart R L, Lukhtanov E A, Gorn V V, Meyer R B Jr., Gamper H B Jr. Oligonucleotides containing 2-aminoadenine and 2-thiothymine act as selectively binding complementary agents, *Biochemistry* 1996) 27:35(34):11170–6
2. Woo J, Meyer R B Jr., Gamper H B., G/C-modified oligodeoxynucleotides with selective complementarity: synthesis and hybridization properties, *Nucleic Acids Res.* (1966) 1:24(13):2470–5;
3. Compagno, D, Lampe J N, Bourget C, Kutyavin I V, Yurchenko L, Lukhtanov E A, Gorn V V, Gamper H B Jr., Toulme J J. Antisense oligonucleotides containing modified bases inhibit in vitro translation of *Leishmania amazonensis* mRNAs by invading the mini-exon hairpin, *J Biol Chem* (1999) 19:274(12)8191–8.
4. PCT WO9712896 and U.S. Pat. No. 5,912,340.
5. Moran, S, Ren R X, Sheils C J, Rumney S 4th, Kool E T, Non-hydrogen bonding 'terminator' nucleosides increases the 3'-end homogeneity of enzymatic RNA and DNA synthesis, *Nucleic Acids Res* (1966)1:24(11):2044–52.
6. PCT WO 00/06779.
7. U.S. Pat. No. 6,001,611.
8. Stump M D, Cherry J L, Weiss R B. The use of modified primers to eliminate cycle sequencing artifacts, *Nucleic Acids Res.* (1999) 1:27(23):4642–8.
9. Huang, M M, Arnheim, M. and Goodman, M F. Extension of base mispairs by Taq DNA polymerase: Implications for single nucleotide discrimination in PCR. *Nucl. Acids. Res.* 20:4567–4573 (1992).
10. Tindall, K R and Kunkel, T A. Fidelity of DNA synthesis by the Thermus aquaticus DNA polymerase. *Biochemistry* 27:6008–6013 (1988).
11. Nyren, P, Karamohamed, S and Ronaghi, M. Detection of single-base changes using a bioluminometric primer extension assay. *Anal. Biochem.* 244:367–373 (1997).
12. Ayyadevara, S, Thaden, JJ, Schmookler Reis, RJ. Discrimination of primer 3'-nucleotide mismatch by Taq DNA polymerase during polymerase chain reaction. Anal. Biochem. 284:11–18 (2000).
13. Pastinen, T., et al., A system for specific, high throughput genotyping by allele specific primer extension on microarrays, Genome Research, 10:1031–42 (2000).
14. Zhang et al., Proc. Natl. Acad. Sci. 89:5847–51 (1992).
15. Casas and Kirkpatrick, Biotechniques, 20: 219–25 (1996).
16. U.S. Pat. No. 6,183,958.
17. U.S. application Ser. No. 09/626,096, filed Jul. 29, 2000 and PCT/US01/02664, filed Jan. 26, 2001.

We claim:

1. A method of determining the identification of a nucleotide at a detection position in a target DNA sequence comprising:
    a) amplifying the target DNA using random primers to generate DNA amplicons;
    b) transcribing said DNA amplicons to generate RNA target sequences;
    c) providing a solid support with a first surface comprising at least one extension probe wherein said extension probe includes an interrogation nucleotide;
    d) hybridizing said RNA target sequence to said extension probe to form a hybridization complex;
    e) contacting said surface with:
        i) a modified reverse transcriptase; and
        ii) at least one chain terminating nucleotide comprising a hapten; under conditions whereby if said chain terminating nucleotide is perfectly complementary to the base of the target sequence immediately adjacent to the 3' end of extension probe in the hybridization complex, said chain terminating nucleotide is added to extension probe to form a modified extension probe;
    f) contacting said modified extension probe with the binding partner of said hapten, wherein said binding partner is labeled; and
    g) detecting the presence of said label to determine the nucleotide at said detection position.

2. The method of claim 1, wherein said modified reverse transcriptase only extends extension probes bound to RNA.

* * * * *

SEQUENCE LISTING

<160> NUMBER OF SEQ ID NOS: 277

<210> SEQ ID NO 1
<211> LENGTH: 23
<212> TYPE: DNA
<213> ORGANISM: Homo sapiens

<400> SEQUENCE: 1
cccagaaggc tttgcaggct tca                                              23

<210> SEQ ID NO 2
<211> LENGTH: 25
<212> TYPE: DNA
<213> ORGANISM: Homo sapiens

<400> SEQUENCE: 2
ctcaccagga aagcaaagac accat                                            25

<210> SEQ ID NO 3
<211> LENGTH: 22
<212> TYPE: DNA
<213> ORGANISM: Homo sapiens

<400> SEQUENCE: 3
tgaagcctct gccagaggcc aa                                               22

<210> SEQ ID NO 4
<211> LENGTH: 25
<212> TYPE: DNA
<213> ORGANISM: Homo sapiens

<400> SEQUENCE: 4
gagaactcgt ccttgtagtc cagca                                            25

<210> SEQ ID NO 5
<211> LENGTH: 24
<212> TYPE: DNA
<213> ORGANISM: Homo sapiens

<400> SEQUENCE: 5
caccttctca caggccttgg tgaa                                             24

-continued

```
<210> SEQ ID NO 6
<211> LENGTH: 23
<212> TYPE: DNA
<213> ORGANISM: Homo sapiens

<400> SEQUENCE: 6
caccctgtgc tctgaggtt gaa                                          23

<210> SEQ ID NO 7
<211> LENGTH: 27
<212> TYPE: DNA
<213> ORGANISM: Homo sapiens

<400> SEQUENCE: 7
cctgacccct gactgctttc tatctaa                                     27

<210> SEQ ID NO 8
<211> LENGTH: 22
<212> TYPE: DNA
<213> ORGANISM: Homo sapiens

<400> SEQUENCE: 8
aggagtgtgg gctgctcctc aa                                          22

<210> SEQ ID NO 9
<211> LENGTH: 26
<212> TYPE: DNA
<213> ORGANISM: Homo sapiens

<400> SEQUENCE: 9
ctgtaggtgt ggcttgttgg gatgaa                                      26

<210> SEQ ID NO 10
<211> LENGTH: 25
<212> TYPE: DNA
<213> ORGANISM: Homo sapiens

<400> SEQUENCE: 10
cacaccactc actgacctcc tttga                                       25

<210> SEQ ID NO 11
<211> LENGTH: 27
<212> TYPE: DNA
<213> ORGANISM: Homo sapiens

<400> SEQUENCE: 11
ctctggttac aggaagctat gggtcaa                                     27

<210> SEQ ID NO 12
<211> LENGTH: 30
<212> TYPE: DNA
<213> ORGANISM: Homo sapiens

<400> SEQUENCE: 12
catgcaagct caatgcaggc tagaatagaa                                  30

<210> SEQ ID NO 13
<211> LENGTH: 21
<212> TYPE: DNA
<213> ORGANISM: Homo sapiens

<400> SEQUENCE: 13
ctctccaccc aacggcactc a                                           21
```

<210> SEQ ID NO 14
<211> LENGTH: 25
<212> TYPE: DNA
<213> ORGANISM: Homo sapiens

<400> SEQUENCE: 14
gcagagagga taaaggcgtc catca                                              25

<210> SEQ ID NO 15
<211> LENGTH: 25
<212> TYPE: DNA
<213> ORGANISM: Homo sapiens

<400> SEQUENCE: 15
atcctgatgt gcagactcga gtgca                                              25

<210> SEQ ID NO 16
<211> LENGTH: 30
<212> TYPE: DNA
<213> ORGANISM: Homo sapiens

<400> SEQUENCE: 16
caagcaaaag aggtacaaca tcaccttgga                                         30

<210> SEQ ID NO 17
<211> LENGTH: 27
<212> TYPE: DNA
<213> ORGANISM: Homo sapiens

<400> SEQUENCE: 17
ccagctctca gattctgtga tgctcaa                                            27

<210> SEQ ID NO 18
<211> LENGTH: 22
<212> TYPE: DNA
<213> ORGANISM: Homo sapiens

<400> SEQUENCE: 18
gggtcagcac atgcccgagc aa                                                 22

<210> SEQ ID NO 19
<211> LENGTH: 26
<212> TYPE: DNA
<213> ORGANISM: Homo sapiens

<400> SEQUENCE: 19
ctctgtattt tggcctggaa cgcatg                                             26

<210> SEQ ID NO 20
<211> LENGTH: 24
<212> TYPE: DNA
<213> ORGANISM: Homo sapiens

<400> SEQUENCE: 20
tcccgagggt tgttgatgtc catc                                               24

<210> SEQ ID NO 21
<211> LENGTH: 25
<212> TYPE: DNA
<213> ORGANISM: Homo sapiens

<400> SEQUENCE: 21
gcaagcggaa gtgtatcggt gagaa                                              25

```
<210> SEQ ID NO 22
<211> LENGTH: 25
<212> TYPE: DNA
<213> ORGANISM: Homo sapiens

<400> SEQUENCE: 22
gcaagcggaa gtgtatcggt gagac                                    25

<210> SEQ ID NO 23
<211> LENGTH: 14
<212> TYPE: DNA
<213> ORGANISM: Homo sapiens

<400> SEQUENCE: 23
tcccagcggg caat                                                14

<210> SEQ ID NO 24
<211> LENGTH: 14
<212> TYPE: DNA
<213> ORGANISM: Homo sapiens

<400> SEQUENCE: 24
tcccagcggg caac                                                14

<210> SEQ ID NO 25
<211> LENGTH: 20
<212> TYPE: DNA
<213> ORGANISM: Homo sapiens

<400> SEQUENCE: 25
ataagggtct tacaaggccg                                          20

<210> SEQ ID NO 26
<211> LENGTH: 21
<212> TYPE: DNA
<213> ORGANISM: Homo sapiens

<400> SEQUENCE: 26
aataagggtc ttacaaggcc a                                        21

<210> SEQ ID NO 27
<211> LENGTH: 20
<212> TYPE: DNA
<213> ORGANISM: Homo sapiens

<400> SEQUENCE: 27
catctaccat gcgtcctgtg                                          20

<210> SEQ ID NO 28
<211> LENGTH: 19
<212> TYPE: DNA
<213> ORGANISM: Homo sapiens

<400> SEQUENCE: 28
atctaccatg cgtcctggg                                           19

<210> SEQ ID NO 29
<211> LENGTH: 18
<212> TYPE: DNA
<213> ORGANISM: Homo sapiens

<400> SEQUENCE: 29
```

-continued

| | |
|---|---|
| tggcctctgc catcttct | 18 |

<210> SEQ ID NO 30
<211> LENGTH: 17
<212> TYPE: DNA
<213> ORGANISM: Homo sapiens

<400> SEQUENCE: 30

| | |
|---|---|
| tggcctctgc catcttg | 17 |

<210> SEQ ID NO 31
<211> LENGTH: 18
<212> TYPE: DNA
<213> ORGANISM: Homo sapiens

<400> SEQUENCE: 31

| | |
|---|---|
| tggcctctgc catcttct | 18 |

<210> SEQ ID NO 32
<211> LENGTH: 18
<212> TYPE: DNA
<213> ORGANISM: Homo sapiens

<400> SEQUENCE: 32

| | |
|---|---|
| tggcctctgc catcttgt | 18 |

<210> SEQ ID NO 33
<211> LENGTH: 17
<212> TYPE: DNA
<213> ORGANISM: Homo sapiens

<400> SEQUENCE: 33

| | |
|---|---|
| ccatgctggg gacagag | 17 |

<210> SEQ ID NO 34
<211> LENGTH: 17
<212> TYPE: DNA
<213> ORGANISM: Homo sapiens

<400> SEQUENCE: 34

| | |
|---|---|
| ccatgctggg gacagaa | 17 |

<210> SEQ ID NO 35
<211> LENGTH: 14
<212> TYPE: DNA
<213> ORGANISM: Homo sapiens

<400> SEQUENCE: 35

| | |
|---|---|
| gaggcggcag ctcc | 14 |

<210> SEQ ID NO 36
<211> LENGTH: 14
<212> TYPE: DNA
<213> ORGANISM: Homo sapiens

<400> SEQUENCE: 36

| | |
|---|---|
| gaggcggcag ctcg | 14 |

<210> SEQ ID NO 37
<211> LENGTH: 14
<212> TYPE: DNA
<213> ORGANISM: Homo sapiens

<400> SEQUENCE: 37

-continued gcccgtttgc gtgc                                                      14

<210> SEQ ID NO 38
<211> LENGTH: 14
<212> TYPE: DNA
<213> ORGANISM: Homo sapiens

<400> SEQUENCE: 38
gcccgtttgc gtgg                                                      14

<210> SEQ ID NO 39
<211> LENGTH: 13
<212> TYPE: DNA
<213> ORGANISM: Homo sapiens

<400> SEQUENCE: 39
gccgccgcgt ttt                                                       13

<210> SEQ ID NO 40
<211> LENGTH: 13
<212> TYPE: DNA
<213> ORGANISM: Homo sapiens

<400> SEQUENCE: 40
gccgccgcgt ttc                                                       13

<210> SEQ ID NO 41
<211> LENGTH: 13
<212> TYPE: DNA
<213> ORGANISM: Homo sapiens

<400> SEQUENCE: 41
cgttcgctcg ccc                                                       13

<210> SEQ ID NO 42
<211> LENGTH: 15
<212> TYPE: DNA
<213> ORGANISM: Homo sapiens

<400> SEQUENCE: 42
ctcgttcgct cgcct                                                     15

<210> SEQ ID NO 43
<211> LENGTH: 17
<212> TYPE: DNA
<213> ORGANISM: Homo sapiens

<400> SEQUENCE: 43
gaaggaggcg aaggccg                                                   17

<210> SEQ ID NO 44
<211> LENGTH: 17
<212> TYPE: DNA
<213> ORGANISM: Homo sapiens

<400> SEQUENCE: 44
gaaggaggcg aaggacg                                                   17

<210> SEQ ID NO 45
<211> LENGTH: 15
<212> TYPE: DNA
<213> ORGANISM: Homo sapiens

```
<400> SEQUENCE: 45
tcagcacgtg gccct                                                   15

<210> SEQ ID NO 46
<211> LENGTH: 15
<212> TYPE: DNA
<213> ORGANISM: Homo sapiens

<400> SEQUENCE: 46
cagcacgtgg cccag                                                   15

<210> SEQ ID NO 47
<211> LENGTH: 19
<212> TYPE: DNA
<213> ORGANISM: Homo sapiens

<400> SEQUENCE: 47
agttcttgag gcactgcga                                               19

<210> SEQ ID NO 48
<211> LENGTH: 21
<212> TYPE: DNA
<213> ORGANISM: Homo sapiens

<400> SEQUENCE: 48
caagttcttg aggcactgct a                                            21

<210> SEQ ID NO 49
<211> LENGTH: 11
<212> TYPE: DNA
<213> ORGANISM: Homo sapiens

<400> SEQUENCE: 49
tcgcgggggg g                                                       11

<210> SEQ ID NO 50
<211> LENGTH: 11
<212> TYPE: DNA
<213> ORGANISM: Homo sapiens

<400> SEQUENCE: 50
tcgcgggggg c                                                       11

<210> SEQ ID NO 51
<211> LENGTH: 19
<212> TYPE: DNA
<213> ORGANISM: Homo sapiens

<400> SEQUENCE: 51
gaattggatc aggtcgtgg                                               19

<210> SEQ ID NO 52
<211> LENGTH: 20
<212> TYPE: DNA
<213> ORGANISM: Homo sapiens

<400> SEQUENCE: 52
agaattggat caggtcgtgt                                              20

<210> SEQ ID NO 53
<211> LENGTH: 22
<212> TYPE: DNA
<213> ORGANISM: Homo sapiens
```

```
<220> FEATURE:
<221> NAME/KEY: modified_base
<222> LOCATION: (5)..(5)
<223> OTHER INFORMATION: I

<400> SEQUENCE: 53
tggtraccca tacaaggcag at                                              22

<210> SEQ ID NO 54
<211> LENGTH: 22
<212> TYPE: DNA
<213> ORGANISM: Homo sapiens
<220> FEATURE:
<221> NAME/KEY: modified_base
<222> LOCATION: (4)..(4)
<223> OTHER INFORMATION: I

<400> SEQUENCE: 54
ggtracccat acaaggcaga cg                                              22

<210> SEQ ID NO 55
<211> LENGTH: 20
<212> TYPE: DNA
<213> ORGANISM: Homo sapiens

<400> SEQUENCE: 55
cgtctgcctt gtatgggtaa                                                 20

<210> SEQ ID NO 56
<211> LENGTH: 20
<212> TYPE: DNA
<213> ORGANISM: Homo sapiens

<400> SEQUENCE: 56
cgtctgcctt gtatgggtga                                                 20

<210> SEQ ID NO 57
<211> LENGTH: 18
<212> TYPE: DNA
<213> ORGANISM: Homo sapiens

<400> SEQUENCE: 57
ggaaggccag gacatagg                                                   18

<210> SEQ ID NO 58
<211> LENGTH: 19
<212> TYPE: DNA
<213> ORGANISM: Homo sapiens

<400> SEQUENCE: 58
aggaaggcca ggacataga                                                  19

<210> SEQ ID NO 59
<211> LENGTH: 22
<212> TYPE: DNA
<213> ORGANISM: Homo sapiens

<400> SEQUENCE: 59
tatgtcctgg ccttccttta ta                                              22

<210> SEQ ID NO 60
<211> LENGTH: 19
<212> TYPE: DNA
<213> ORGANISM: Homo sapiens
```

-continued

```
<400> SEQUENCE: 60
gtcctggcct tcctttatg                                              19

<210> SEQ ID NO 61
<211> LENGTH: 21
<212> TYPE: DNA
<213> ORGANISM: Homo sapiens

<400> SEQUENCE: 61
gtctgtgaat catgacccac t                                           21

<210> SEQ ID NO 62
<211> LENGTH: 21
<212> TYPE: DNA
<213> ORGANISM: Homo sapiens

<400> SEQUENCE: 62
gtctgtgaat catgacccag t                                           21

<210> SEQ ID NO 63
<211> LENGTH: 20
<212> TYPE: DNA
<213> ORGANISM: Homo sapiens
<220> FEATURE:
<221> NAME/KEY: modified_base
<222> LOCATION: (8)..(8)
<223> OTHER INFORMATION: I

<400> SEQUENCE: 63
gtccttgrtg atgaggccgt                                             20

<210> SEQ ID NO 64
<211> LENGTH: 20
<212> TYPE: DNA
<213> ORGANISM: Homo sapiens
<220> FEATURE:
<221> NAME/KEY: modified_base
<222> LOCATION: (8)..(8)
<223> OTHER INFORMATION: I

<400> SEQUENCE: 64
gtccttgrtg atgaggccat                                             20

<210> SEQ ID NO 65
<211> LENGTH: 18
<212> TYPE: DNA
<213> ORGANISM: Homo sapiens

<400> SEQUENCE: 65
tgctggtcag gtccttgt                                               18

<210> SEQ ID NO 66
<211> LENGTH: 17
<212> TYPE: DNA
<213> ORGANISM: Homo sapiens

<400> SEQUENCE: 66
gctggtcagg tccttgc                                                17

<210> SEQ ID NO 67
<211> LENGTH: 17
<212> TYPE: DNA
<213> ORGANISM: Homo sapiens

<400> SEQUENCE: 67
```

```
ttcagtgggc aaaaggc                                              17

<210> SEQ ID NO 68
<211> LENGTH: 19
<212> TYPE: DNA
<213> ORGANISM: Homo sapiens

<400> SEQUENCE: 68
ttttcagtgg gcaaaaggt                                            19

<210> SEQ ID NO 69
<211> LENGTH: 22
<212> TYPE: DNA
<213> ORGANISM: Homo sapiens

<400> SEQUENCE: 69
tcaattagcg tttaaggtga gc                                        22

<210> SEQ ID NO 70
<211> LENGTH: 22
<212> TYPE: DNA
<213> ORGANISM: Homo sapiens

<400> SEQUENCE: 70
tcaattagcg tttaaggtga gg                                        22

<210> SEQ ID NO 71
<211> LENGTH: 21
<212> TYPE: DNA
<213> ORGANISM: Homo sapiens

<400> SEQUENCE: 71
cccaaacact tacaccaaac a                                         21

<210> SEQ ID NO 72
<211> LENGTH: 22
<212> TYPE: DNA
<213> ORGANISM: Homo sapiens

<400> SEQUENCE: 72
acccaaacac ttacaccaaa ct                                        22

<210> SEQ ID NO 73
<211> LENGTH: 23
<212> TYPE: DNA
<213> ORGANISM: Homo sapiens

<400> SEQUENCE: 73
gagtatagtg gggttccatg agt                                       23

<210> SEQ ID NO 74
<211> LENGTH: 23
<212> TYPE: DNA
<213> ORGANISM: Homo sapiens

<400> SEQUENCE: 74
gagtatagtg gggttccatg att                                       23

<210> SEQ ID NO 75
<211> LENGTH: 25
<212> TYPE: DNA
<213> ORGANISM: Homo sapiens
```

-continued

```
<400> SEQUENCE: 75
gaaatggcct cttccagaaa actcg                                            25

<210> SEQ ID NO 76
<211> LENGTH: 26
<212> TYPE: DNA
<213> ORGANISM: Homo sapiens

<400> SEQUENCE: 76
ggaaatggcc tcttccagaa aactcc                                           26

<210> SEQ ID NO 77
<211> LENGTH: 25
<212> TYPE: DNA
<213> ORGANISM: Homo sapiens

<400> SEQUENCE: 77
ctcctcttcc ccatcccaaa attct                                            25

<210> SEQ ID NO 78
<211> LENGTH: 23
<212> TYPE: DNA
<213> ORGANISM: Homo sapiens

<400> SEQUENCE: 78
cctcttcccc atcccaaaat tcc                                              23

<210> SEQ ID NO 79
<211> LENGTH: 21
<212> TYPE: DNA
<213> ORGANISM: Homo sapiens

<400> SEQUENCE: 79
gcgggcttcc tcttgaacac g                                                21

<210> SEQ ID NO 80
<211> LENGTH: 22
<212> TYPE: DNA
<213> ORGANISM: Homo sapiens

<400> SEQUENCE: 80
agcgggcttc ctcttgaaca ca                                               22

<210> SEQ ID NO 81
<211> LENGTH: 19
<212> TYPE: DNA
<213> ORGANISM: Homo sapiens

<400> SEQUENCE: 81
gattgtaagc accccctga                                                   19

<210> SEQ ID NO 82
<211> LENGTH: 17
<212> TYPE: DNA
<213> ORGANISM: Homo sapiens

<400> SEQUENCE: 82
ttgtaagcac ccctgg                                                      17

<210> SEQ ID NO 83
<211> LENGTH: 23
<212> TYPE: DNA
<213> ORGANISM: Homo sapiens
```

```
<400> SEQUENCE: 83
ccactatcat tgattatttc cca                                              23

<210> SEQ ID NO 84
<211> LENGTH: 23
<212> TYPE: DNA
<213> ORGANISM: Homo sapiens

<400> SEQUENCE: 84
ccactatcat tgattatttc ccg                                              23

<210> SEQ ID NO 85
<211> LENGTH: 27
<212> TYPE: DNA
<213> ORGANISM: Homo sapiens
<220> FEATURE:
<221> NAME/KEY: modified_base
<222> LOCATION: (7)..(7)
<223> OTHER INFORMATION: I

<400> SEQUENCE: 85
aggcagrtat ggggctagaa gcactga                                          27

<210> SEQ ID NO 86
<211> LENGTH: 26
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 86
ggcagrtatg gggctagaag cactgg                                           26

<210> SEQ ID NO 87
<211> LENGTH: 26
<212> TYPE: DNA
<213> ORGANISM: Homo sapiens

<400> SEQUENCE: 87
aggagcagga agatggccac tatcat                                           26

<210> SEQ ID NO 88
<211> LENGTH: 25
<212> TYPE: DNA
<213> ORGANISM: Homo sapiens

<400> SEQUENCE: 88
ggagcaggaa gatggccact atcac                                            25

<210> SEQ ID NO 89
<211> LENGTH: 18
<212> TYPE: DNA
<213> ORGANISM: Homo sapiens

<400> SEQUENCE: 89
ggacctgatg caccggca                                                    18

<210> SEQ ID NO 90
<211> LENGTH: 18
<212> TYPE: DNA
<213> ORGANISM: Homo sapiens
```

```
<400> SEQUENCE: 90
ggacctgatg caccggcg                                          18

<210> SEQ ID NO 91
<211> LENGTH: 21
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 91
tgrgtagcgt gcagcccagc g                                      21

<210> SEQ ID NO 92
<211> LENGTH: 22
<212> TYPE: DNA
<213> ORGANISM: Homo sapiens
<220> FEATURE:
<221> NAME/KEY: modified_base
<222> LOCATION: (4)..(4)
<223> OTHER INFORMATION: I

<400> SEQUENCE: 92
gtgrgtagcg tgcagcccag ca                                     22

<210> SEQ ID NO 93
<211> LENGTH: 13
<212> TYPE: DNA
<213> ORGANISM: Homo sapiens

<400> SEQUENCE: 93
gggggcctgg tgg                                               13

<210> SEQ ID NO 94
<211> LENGTH: 14
<212> TYPE: DNA
<213> ORGANISM: Homo sapiens

<400> SEQUENCE: 94 aggggggcctg gtga                                             14

<210> SEQ ID NO 95
<211> LENGTH: 17
<212> TYPE: DNA
<213> ORGANISM: Homo sapiens

<400> SEQUENCE: 95
ccccctgcca ctgccca                                           17

<210> SEQ ID NO 96
<211> LENGTH: 16
<212> TYPE: DNA
<213> ORGANISM: Homo sapiens

<400> SEQUENCE: 96 ccccctgccac tgcccg                                           16

<210> SEQ ID NO 97
<211> LENGTH: 29
<212> TYPE: DNA
<213> ORGANISM: Homo sapiens
<220> FEATURE:
<221> NAME/KEY: modified_base
```

```
<222> LOCATION: (15)..(15)
<223> OTHER INFORMATION: I

<400> SEQUENCE: 97
ccctgccact gcccrggctg ggcaacctg                                    29

<210> SEQ ID NO 98
<211> LENGTH: 29
<212> TYPE: DNA
<213> ORGANISM: Homo sapiens
<220> FEATURE:
<221> NAME/KEY: modified_base
<222> LOCATION: (15)..(15)
<223> OTHER INFORMATION: I

<400> SEQUENCE: 98
ccctgccact gcccrggctg ggcaaccttt                                   29

<210> SEQ ID NO 99
<211> LENGTH: 30
<212> TYPE: DNA
<213> ORGANISM: Homo sapiens
<220> FEATURE:
<221> NAME/KEY: modified_base
<222> LOCATION: (14)..(14)
<223> OTHER INFORMATION: I

<400> SEQUENCE: 99
cctgccactg cccrggctgg gcaacctgct                                   30

<210> SEQ ID NO 100
<211> LENGTH: 30
<212> TYPE: DNA
<213> ORGANISM: Homo sapiens
<220> FEATURE:
<221> NAME/KEY: modified_base
<222> LOCATION: (14)..(14)
<223> OTHER INFORMATION: I

<400> SEQUENCE: 100
cctgccactg cccrggctgg gcaaccttct                                   30

<210> SEQ ID NO 101
<211> LENGTH: 13
<212> TYPE: DNA
<213> ORGANISM: Homo sapiens

<400> SEQUENCE: 101
cggcgccgca agt                                                     13

<210> SEQ ID NO 102
<211> LENGTH: 13
<212> TYPE: DNA
<213> ORGANISM: Homo sapiens

<400> SEQUENCE: 102
cggcgccgca act                                                     13

<210> SEQ ID NO 103
<211> LENGTH: 18
<212> TYPE: DNA
<213> ORGANISM: Homo sapiens

<400> SEQUENCE: 103
tgaccctccc tctgcact                                                18
```

```
<210> SEQ ID NO 104
<211> LENGTH: 18
<212> TYPE: DNA
<213> ORGANISM: Homo sapiens

<400> SEQUENCE: 104
tgaccctccc tctgcagt                                                 18

<210> SEQ ID NO 105
<211> LENGTH: 15
<212> TYPE: DNA
<213> ORGANISM: Homo sapiens

<400> SEQUENCE: 105
gctcaatggg ctggc                                                    15

<210> SEQ ID NO 106
<211> LENGTH: 17
<212> TYPE: DNA
<213> ORGANISM: Homo sapiens

<400> SEQUENCE: 106
gtgctcaatg ggctggt                                                  17

<210> SEQ ID NO 107
<211> LENGTH: 16
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 107
cgccgrgggt caccat                                                   16

<210> SEQ ID NO 108
<211> LENGTH: 16
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 108
cgccgrgggt caccag                                                   16

<210> SEQ ID NO 109
<211> LENGTH: 19
<212> TYPE: DNA
<213> ORGANISM: Homo sapiens
<220> FEATURE:
<221> NAME/KEY: modified_base
<222> LOCATION: (7)..(7)
<223> OTHER INFORMATION: I

<400> SEQUENCE: 109
gaggcgrtgg tgacccacg                                                19

<210> SEQ ID NO 110
<211> LENGTH: 18
<212> TYPE: DNA
<213> ORGANISM: Homo sapiens
<220> FEATURE:
<221> NAME/KEY: modified_base
```

```
<222> LOCATION: (8)..(8)
<223> OTHER INFORMATION: I

<400> SEQUENCE: 110
cgaggcgrtg gtgacccg                                                 18

<210> SEQ ID NO 111
<211> LENGTH: 12
<212> TYPE: DNA
<213> ORGANISM: Homo sapiens

<400> SEQUENCE: 111
gcggtcggcg gt                                                       12

<210> SEQ ID NO 112
<211> LENGTH: 13
<212> TYPE: DNA
<213> ORGANISM: Homo sapiens

<400> SEQUENCE: 112
ggcggtcggc cgt                                                      13

<210> SEQ ID NO 113
<211> LENGTH: 16
<212> TYPE: DNA
<213> ORGANISM: Homo sapiens

<400> SEQUENCE: 113
gcctgtgccc atcacc                                                   16

<210> SEQ ID NO 114
<211> LENGTH: 17
<212> TYPE: DNA
<213> ORGANISM: Homo sapiens

<400> SEQUENCE: 114
cgcctgtgcc catcatc                                                  17

<210> SEQ ID NO 115
<211> LENGTH: 21
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 115
ccraaaccca ggatctgggt g                                             21

<210> SEQ ID NO 116
<211> LENGTH: 21
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 116
ccraaaccca ggatctggat g                                             21

<210> SEQ ID NO 117
<211> LENGTH: 16
<212> TYPE: DNA
```

```
<213> ORGANISM: Homo sapiens

<400> SEQUENCE: 117
tgggaacgcg gcccga                                                    16

<210> SEQ ID NO 118
<211> LENGTH: 16
<212> TYPE: DNA
<213> ORGANISM: Homo sapiens

<400> SEQUENCE: 118
tgggaacgcg gcccaa                                                    16

<210> SEQ ID NO 119
<211> LENGTH: 17
<212> TYPE: DNA
<213> ORGANISM: Homo sapiens

<400> SEQUENCE: 119
cagaggcgct tctccat                                                   17

<210> SEQ ID NO 120
<211> LENGTH: 17
<212> TYPE: DNA
<213> ORGANISM: Homo sapiens

<400> SEQUENCE: 120
cagaggcgct tctccgt                                                   17

<210> SEQ ID NO 121
<211> LENGTH: 18
<212> TYPE: DNA
<213> ORGANISM: Homo sapiens
<220> FEATURE:
<221> NAME/KEY: modified_base
<222> LOCATION: (16)..(16)
<223> OTHER INFORMATION: I

<400> SEQUENCE: 121
cagaggcgct tctccrtc                                                  18

<210> SEQ ID NO 122
<211> LENGTH: 18
<212> TYPE: DNA
<213> ORGANISM: Homo sapiens
<220> FEATURE:
<221> NAME/KEY: modified_base
<222> LOCATION: (16)..(16)
<223> OTHER INFORMATION: I

<400> SEQUENCE: 122
cagaggcgct tctccrtg                                                  18

<210> SEQ ID NO 123
<211> LENGTH: 22
<212> TYPE: DNA
<213> ORGANISM: Homo sapiens

<400> SEQUENCE: 123
tgggcaagaa gtcgctggag ca                                             22

<210> SEQ ID NO 124
<211> LENGTH: 22
<212> TYPE: DNA
<213> ORGANISM: Homo sapiens
```

<400> SEQUENCE: 124
tgggcaagaa gtcgctggag ga                                                    22

<210> SEQ ID NO 125
<211> LENGTH: 20
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 125
gcrgcctcct cggtcacccc                                                       20

<210> SEQ ID NO 126
<211> LENGTH: 20
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 126
gcrgcctcct cggtcaccca                                                       20

<210> SEQ ID NO 127
<211> LENGTH: 21
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 127
gcrgcctcct cggtcacccc t                                                     21

<210> SEQ ID NO 128
<211> LENGTH: 21
<212> TYPE: DNA
<213> ORGANISM: Homo sapiens
<220> FEATURE:
<221> NAME/KEY: modified_base
<222> LOCATION: (3)..(3)
<223> OTHER INFORMATION: I

<400> SEQUENCE: 128
gcrgcctcct cggtcaccca c                                                     21

<210> SEQ ID NO 129
<211> LENGTH: 17
<212> TYPE: DNA
<213> ORGANISM: Homo sapiens

<400> SEQUENCE: 129
cggcacaaag gcaggcg                                                          17

<210> SEQ ID NO 130
<211> LENGTH: 18
<212> TYPE: DNA
<213> ORGANISM: Homo sapiens

<400> SEQUENCE: 130

```
                                   -continued
gcggcacaaa ggcaggca                                              18

<210> SEQ ID NO 131
<211> LENGTH: 16
<212> TYPE: DNA
<213> ORGANISM: Homo sapiens

<400> SEQUENCE: 131
tgtgccgcct tcgcca                                                16

<210> SEQ ID NO 132
<211> LENGTH: 15
<212> TYPE: DNA
<213> ORGANISM: Homo sapiens

<400> SEQUENCE: 132
gtgccgcctt cgccg                                                 15

<210> SEQ ID NO 133
<211> LENGTH: 20
<212> TYPE: DNA
<213> ORGANISM: Homo sapiens
<220> FEATURE:
<221> NAME/KEY: modified_base
<222> LOCATION: (11)..(11)
<223> OTHER INFORMATION: I

<400> SEQUENCE: 133
cgccttcgcc raccactccg                                            20

<210> SEQ ID NO 134
<211> LENGTH: 21
<212> TYPE: DNA
<213> ORGANISM: Homo sapiens
<220> FEATURE:
<221> NAME/KEY: modified_base
<222> LOCATION: (12)..(12)
<223> OTHER INFORMATION: I

<400> SEQUENCE: 134
ccgccttcgc craccactcc t                                          21

<210> SEQ ID NO 135
<211> LENGTH: 16
<212> TYPE: DNA
<213> ORGANISM: Homo sapiens

<400> SEQUENCE: 135
catctcccac ccccaa                                                16

<210> SEQ ID NO 136
<211> LENGTH: 16
<212> TYPE: DNA
<213> ORGANISM: Homo sapiens

<400> SEQUENCE: 136
catctcccac ccccag                                                16

<210> SEQ ID NO 137
<211> LENGTH: 16
<212> TYPE: DNA
<213> ORGANISM: Homo sapiens
<220> FEATURE:
<221> NAME/KEY: modified_base
<222> LOCATION: (5)..(5)
<223> OTHER INFORMATION: I
```

```
<400> SEQUENCE: 137
agagrccgtt ggggcg                                                      16

<210> SEQ ID NO 138
<211> LENGTH: 17
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 138
aagagrccgt tggggca                                                     17

<210> SEQ ID NO 139
<211> LENGTH: 17
<212> TYPE: DNA
<213> ORGANISM: Homo sapiens

<400> SEQUENCE: 139
cggctttgtc caagagg                                                     17

<210> SEQ ID NO 140
<211> LENGTH: 18
<212> TYPE: DNA
<213> ORGANISM: Homo sapiens

<400> SEQUENCE: 140
acggctttgt ccaagaga                                                    18

<210> SEQ ID NO 141
<211> LENGTH: 18
<212> TYPE: DNA
<213> ORGANISM: Homo sapiens

<400> SEQUENCE: 141
ccagcagcct gaggaagt                                                    18

<210> SEQ ID NO 142
<211> LENGTH: 17
<212> TYPE: DNA
<213> ORGANISM: Homo sapiens

<400> SEQUENCE: 142
cagcagcctg aggaagc                                                     17

<210> SEQ ID NO 143
<211> LENGTH: 25
<212> TYPE: DNA
<213> ORGANISM: Homo sapiens

<400> SEQUENCE: 143
tcaggctgct ggacctagct cagga                                            25

<210> SEQ ID NO 144
<211> LENGTH: 25
<212> TYPE: DNA
<213> ORGANISM: Homo sapiens

<400> SEQUENCE: 144
caggctgctg gacctagctc aggga                                            25
```

<210> SEQ ID NO 145
<211> LENGTH: 19
<212> TYPE: DNA
<213> ORGANISM: Homo sapiens

<400> SEQUENCE: 145
tggacctagc tcaggagga                                              19

<210> SEQ ID NO 146
<211> LENGTH: 18
<212> TYPE: DNA
<213> ORGANISM: Homo sapiens

<400> SEQUENCE: 146
ggacctagct caggaggg                                               18

<210> SEQ ID NO 147
<211> LENGTH: 26
<212> TYPE: DNA
<213> ORGANISM: Homo sapiens
<220> FEATURE:
<221> NAME/KEY: modified_base
<222> LOCATION: (24)..(24)
<223> OTHER INFORMATION: I

<400> SEQUENCE: 147
gctgctggac ctagctcagg aggrac                                      26

<210> SEQ ID NO 148
<211> LENGTH: 26
<212> TYPE: DNA
<213> ORGANISM: Homo sapiens
<220> FEATURE:
<221> NAME/KEY: modified_base
<222> LOCATION: (24)..(24)
<223> OTHER INFORMATION: I

<400> SEQUENCE: 148
gctgctggac ctagctcagg aggrat                                      26

<210> SEQ ID NO 149
<211> LENGTH: 16
<212> TYPE: DNA
<213> ORGANISM: Homo sapiens

<400> SEQUENCE: 149
cccgactcct ccttcg                                                 16

<210> SEQ ID NO 150
<211> LENGTH: 17
<212> TYPE: DNA
<213> ORGANISM: Homo sapiens

<400> SEQUENCE: 150
gcccgactcc tccttca                                                17

<210> SEQ ID NO 151
<211> LENGTH: 21
<212> TYPE: DNA
<213> ORGANISM: Homo sapiens
<220> FEATURE:
<221> NAME/KEY: modified_base
<222> LOCATION: (11)..(11)
<223> OTHER INFORMATION: I

<400> SEQUENCE: 151
tcctcctgca ratcccagcg c                                         21

<210> SEQ ID NO 152
<211> LENGTH: 22
<212> TYPE: DNA
<213> ORGANISM: Homo sapiens
<220> FEATURE:
<221> NAME/KEY: modified_base
<222> LOCATION: (12)..(12)
<223> OTHER INFORMATION: I

<400> SEQUENCE: 152
gtcctcctgc aratcccagc gt                                        22

<210> SEQ ID NO 153
<211> LENGTH: 27
<212> TYPE: DNA
<213> ORGANISM: Homo sapiens

<400> SEQUENCE: 153
ctggatgagc tgctaactga gcacagg                                   27

<210> SEQ ID NO 154
<211> LENGTH: 27
<212> TYPE: DNA
<213> ORGANISM: Homo sapiens

<400> SEQUENCE: 154
ctggatgagc tgctaactga gcacggg                                   27

<210> SEQ ID NO 155
<211> LENGTH: 26
<212> TYPE: DNA
<213> ORGANISM: Homo sapiens

<400> SEQUENCE: 155
gctggatgag ctgctaactg agcaca                                    26

<210> SEQ ID NO 156
<211> LENGTH: 27
<212> TYPE: DNA
<213> ORGANISM: Homo sapiens

<400> SEQUENCE: 156
gctggatgag ctgctaactg agcacgg                                   27

<210> SEQ ID NO 157
<211> LENGTH: 17
<212> TYPE: DNA
<213> ORGANISM: Homo sapiens

<400> SEQUENCE: 157
gggacccagc ccagcca                                              17

<210> SEQ ID NO 158
<211> LENGTH: 17
<212> TYPE: DNA
<213> ORGANISM: Homo sapiens

<400> SEQUENCE: 158
gggacccagc ccagccc                                              17

<210> SEQ ID NO 159

-continued

```
<211> LENGTH: 24
<212> TYPE: DNA
<213> ORGANISM: Homo sapiens
<220> FEATURE:
<221> NAME/KEY: modified_base
<222> LOCATION: (9)..(9)
<223> OTHER INFORMATION: I

<400> SEQUENCE: 159
gcccagccrc cccgagacct gagg                                              24

<210> SEQ ID NO 160
<211> LENGTH: 24
<212> TYPE: DNA
<213> ORGANISM: Homo sapiens
<220> FEATURE:
<221> NAME/KEY: modified_base
<222> LOCATION: (9)..(9)
<223> OTHER INFORMATION: I

<400> SEQUENCE: 160
gcccagccrc cccgagacct gact                                              24

<210> SEQ ID NO 161
<211> LENGTH: 21
<212> TYPE: DNA
<213> ORGANISM: Homo sapiens

<400> SEQUENCE: 161
tggcagccac tctcaccttc t                                                 21

<210> SEQ ID NO 162
<211> LENGTH: 19
<212> TYPE: DNA
<213> ORGANISM: Homo sapiens

<400> SEQUENCE: 162
tggcagccac tctcacctc                                                    19

<210> SEQ ID NO 163
<211> LENGTH: 21
<212> TYPE: DNA
<213> ORGANISM: Homo sapiens

<400> SEQUENCE: 163
gcttcaatga tgagaacctg c                                                 21

<210> SEQ ID NO 164
<211> LENGTH: 22
<212> TYPE: DNA
<213> ORGANISM: Homo sapiens

<400> SEQUENCE: 164
agcttcaatg atgagaacct gt                                                22

<210> SEQ ID NO 165
<211> LENGTH: 26
<212> TYPE: DNA
<213> ORGANISM: Homo sapiens

<400> SEQUENCE: 165
gcagagaaca ggtcagccac cactat                                            26

<210> SEQ ID NO 166
<211> LENGTH: 26
```

```
<212> TYPE: DNA
<213> ORGANISM: Homo sapiens

<400> SEQUENCE: 166
gcagagaaca ggtcagccac cactag                                26

<210> SEQ ID NO 167
<211> LENGTH: 25
<212> TYPE: DNA
<213> ORGANISM: Homo sapiens
<220> FEATURE:
<221> NAME/KEY: modified_base
<222> LOCATION: (20)..(21)
<223> OTHER INFORMATION: I

<400> SEQUENCE: 167
tgggctcacg ctgcacatcr rgagg                                 25

<210> SEQ ID NO 168
<211> LENGTH: 21
<212> TYPE: DNA
<213> ORGANISM: Homo sapiens
<220> FEATURE:
<221> NAME/KEY: modified_base
<222> LOCATION: (17)..(18)
<223> OTHER INFORMATION: I

<400> SEQUENCE: 168
gctcacgctg cacatcrrga t                                     21

<210> SEQ ID NO 169
<211> LENGTH: 22
<212> TYPE: DNA
<213> ORGANISM: Homo sapiens
<220> FEATURE:
<221> NAME/KEY: modified_base
<222> LOCATION: (17)..(18)
<223> OTHER INFORMATION: I

<400> SEQUENCE: 169
gctcacgctg cacatcrrga gg                                    22

<210> SEQ ID NO 170
<211> LENGTH: 21
<212> TYPE: DNA
<213> ORGANISM: Homo sapiens
<220> FEATURE:
<221> NAME/KEY: modified_base
<222> LOCATION: (17)..(18)
<223> OTHER INFORMATION: I

<400> SEQUENCE: 170
gctcacgctg cacatcrrga t                                     21

<210> SEQ ID NO 171
<211> LENGTH: 26
<212> TYPE: DNA
<213> ORGANISM: Homo sapiens
<220> FEATURE:
<221> NAME/KEY: modified_base
<222> LOCATION: (23)..(23)
<223> OTHER INFORMATION: I

<400> SEQUENCE: 171
ggcctcctgc tcatgatcct acrtcc                                26

<210> SEQ ID NO 172
```

<211> LENGTH: 27
<212> TYPE: DNA
<213> ORGANISM: Homo sapiens
<220> FEATURE:
<221> NAME/KEY: modified_base
<222> LOCATION: (24)..(24)
<223> OTHER INFORMATION: I

<400> SEQUENCE: 172
gggcctcctg ctcatgatcc tacrtct                              27

<210> SEQ ID NO 173
<211> LENGTH: 20
<212> TYPE: DNA
<213> ORGANISM: Homo sapiens

<400> SEQUENCE: 173
tgggctcacg ctgcacatct                                      20

<210> SEQ ID NO 174
<211> LENGTH: 19
<212> TYPE: DNA
<213> ORGANISM: Homo sapiens

<400> SEQUENCE: 174
gggctcacgc tgcacatcc                                       19

<210> SEQ ID NO 175
<211> LENGTH: 24
<212> TYPE: DNA
<213> ORGANISM: Homo sapiens

<400> SEQUENCE: 175
gtgtccaaca ggagatcgac gaca                                 24

<210> SEQ ID NO 176
<211> LENGTH: 23
<212> TYPE: DNA
<213> ORGANISM: Homo sapiens

<400> SEQUENCE: 176
tgtccaacag gagatcgacg acg                                  23

<210> SEQ ID NO 177
<211> LENGTH: 26
<212> TYPE: DNA
<213> ORGANISM: Homo sapiens
<220> FEATURE:
<221> NAME/KEY: modified_base
<222> LOCATION: (9)..(9)
<223> OTHER INFORMATION: I

<400> SEQUENCE: 177
tcgacgacrt gatagggcag gtgcgg                               26

<210> SEQ ID NO 178
<211> LENGTH: 26
<212> TYPE: DNA
<213> ORGANISM: Homo sapiens
<220> FEATURE:
<221> NAME/KEY: modified_base
<222> LOCATION: (10)..(10)
<223> OTHER INFORMATION: I

<400> SEQUENCE: 178
atcgacgacr tgatagggca ggtggg                               26

```
<210> SEQ ID NO 179
<211> LENGTH: 19
<212> TYPE: DNA
<213> ORGANISM: Homo sapiens

<400> SEQUENCE: 179
tgcagcgctt tggggacac                                                19

<210> SEQ ID NO 180
<211> LENGTH: 20
<212> TYPE: DNA
<213> ORGANISM: Homo sapiens

<400> SEQUENCE: 180
gtgcagcgct ttggggacat                                               20

<210> SEQ ID NO 181
<211> LENGTH: 17
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 181
ggacarcgtc cccctga                                                  17

<210> SEQ ID NO 182
<211> LENGTH: 17
<212> TYPE: DNA
<213> ORGANISM: Homo sapiens
<220> FEATURE:
<221> NAME/KEY: modified_base
<222> LOCATION: (6)..(6)
<223> OTHER INFORMATION: I

<400> SEQUENCE: 182
ggacarcgtc cccctgg                                                  17

<210> SEQ ID NO 183
<211> LENGTH: 23
<212> TYPE: DNA
<213> ORGANISM: Homo sapiens

<400> SEQUENCE: 183
agacggcctc atccttcagc act                                           23

<210> SEQ ID NO 184
<211> LENGTH: 21
<212> TYPE: DNA
<213> ORGANISM: Homo sapiens

<400> SEQUENCE: 184
acggcctcat ccttcagcac c                                             21

<210> SEQ ID NO 185
<211> LENGTH: 22
<212> TYPE: DNA
<213> ORGANISM: Homo sapiens

<400> SEQUENCE: 185
ctgaaggatg aggccgtctg ga                                            22
```

```
<210> SEQ ID NO 186
<211> LENGTH: 21
<212> TYPE: DNA
<213> ORGANISM: Homo sapiens

<400> SEQUENCE: 186
tgaaggatga ggccgtctgg g                                              21

<210> SEQ ID NO 187
<211> LENGTH: 18
<212> TYPE: DNA
<213> ORGANISM: Homo sapiens

<400> SEQUENCE: 187
ccttccgctt ccaccccc                                                  18

<210> SEQ ID NO 188
<211> LENGTH: 18
<212> TYPE: DNA
<213> ORGANISM: Homo sapiens

<400> SEQUENCE: 188
ccttccgctt ccacccg                                                   18

<210> SEQ ID NO 189
<211> LENGTH: 24
<212> TYPE: DNA
<213> ORGANISM: Homo sapiens
<220> FEATURE:
<221> NAME/KEY: modified_base
<222> LOCATION: (13)..(13)
<223> OTHER INFORMATION: I

<400> SEQUENCE: 189
cgcttccacc ccraacactt cccg                                           24

<210> SEQ ID NO 190
<211> LENGTH: 25
<212> TYPE: DNA
<213> ORGANISM: Homo sapiens
<220> FEATURE:
<221> NAME/KEY: modified_base
<222> LOCATION: (14)..(14)
<223> OTHER INFORMATION: I

<400> SEQUENCE: 190
ccgcttccac cccraacact tcctg                                          25

<210> SEQ ID NO 191
<211> LENGTH: 18
<212> TYPE: DNA
<213> ORGANISM: Homo sapiens

<400> SEQUENCE: 191
cccctcccca caggccac                                                  18

<210> SEQ ID NO 192
<211> LENGTH: 17
<212> TYPE: DNA
<213> ORGANISM: Homo sapiens

<400> SEQUENCE: 192
ccctccccac aggccgc                                                   17
```

```
<210> SEQ ID NO 193
<211> LENGTH: 20
<212> TYPE: DNA
<213> ORGANISM: Homo sapiens

<400> SEQUENCE: 193
cagtgggcac cgagaagctg                                              20

<210> SEQ ID NO 194
<211> LENGTH: 22
<212> TYPE: DNA
<213> ORGANISM: Homo sapiens

<400> SEQUENCE: 194
tccagtgggc accgagaagc ta                                           22

<210> SEQ ID NO 195
<211> LENGTH: 19
<212> TYPE: DNA
<213> ORGANISM: Homo sapiens

<400> SEQUENCE: 195
ctgcacctaa cactgcagc                                               19

<210> SEQ ID NO 196
<211> LENGTH: 19
<212> TYPE: DNA
<213> ORGANISM: Homo sapiens

<400> SEQUENCE: 196
ctgcacctaa cactgcacc                                               19

<210> SEQ ID NO 197
<211> LENGTH: 33
<212> TYPE: DNA
<213> ORGANISM: Homo sapiens

<400> SEQUENCE: 197
cattctatac ttgtatttat acaaaaatga gag                               33

<210> SEQ ID NO 198
<211> LENGTH: 33
<212> TYPE: DNA
<213> ORGANISM: Homo sapiens

<400> SEQUENCE: 198
cattctatac ttgtatttat acaaaaatga gac                               33

<210> SEQ ID NO 199
<211> LENGTH: 27
<212> TYPE: DNA
<213> ORGANISM: Homo sapiens

<400> SEQUENCE: 199
tcttaattca taggttgcaa ttttgta                                      27

<210> SEQ ID NO 200
<211> LENGTH: 28
<212> TYPE: DNA
<213> ORGANISM: Homo sapiens

<400> SEQUENCE: 200
ttcttaattc ataggttgca attttata                                     28
```

```
<210> SEQ ID NO 201
<211> LENGTH: 27
<212> TYPE: DNA
<213> ORGANISM: Homo sapiens

<400> SEQUENCE: 201
ttgcaaccta tgaattaaga acttcta                                    27

<210> SEQ ID NO 202
<211> LENGTH: 26
<212> TYPE: DNA
<213> ORGANISM: Homo sapiens

<400> SEQUENCE: 202
attgcaacct atgaattaag aactcc                                     26

<210> SEQ ID NO 203
<211> LENGTH: 28
<212> TYPE: DNA
<213> ORGANISM: Homo sapiens

<400> SEQUENCE: 203
gatttgtttt acattagggt aaatttgg                                   28

<210> SEQ ID NO 204
<211> LENGTH: 29
<212> TYPE: DNA
<213> ORGANISM: Homo sapiens

<400> SEQUENCE: 204
ggatttgttt tacattaggg taaatttag                                  29

<210> SEQ ID NO 205
<211> LENGTH: 17
<212> TYPE: DNA
<213> ORGANISM: Homo sapiens

<400> SEQUENCE: 205
gtggggtgag gtaccgt                                               17

<210> SEQ ID NO 206
<211> LENGTH: 17
<212> TYPE: DNA
<213> ORGANISM: Homo sapiens

<400> SEQUENCE: 206
gtggggtgag gtaccga                                               17

<210> SEQ ID NO 207
<211> LENGTH: 15
<212> TYPE: DNA
<213> ORGANISM: Homo sapiens

<400> SEQUENCE: 207
tgccaaaggg cagga                                                 15

<210> SEQ ID NO 208
<211> LENGTH: 16
<212> TYPE: DNA
<213> ORGANISM: Homo sapiens

<400> SEQUENCE: 208
gtgccaaagg gcaggt                                                16
```

<210> SEQ ID NO 209
<211> LENGTH: 16
<212> TYPE: DNA
<213> ORGANISM: Homo sapiens

<400> SEQUENCE: 209 gcccctttggc actggt                                                      16

<210> SEQ ID NO 210
<211> LENGTH: 15
<212> TYPE: DNA
<213> ORGANISM: Homo sapiens

<400> SEQUENCE: 210
ccctttggca ctggc                                                        15

<210> SEQ ID NO 211
<211> LENGTH: 19
<212> TYPE: DNA
<213> ORGANISM: Homo sapiens

<400> SEQUENCE: 211
ggagttcccc gttgtctaa                                                    19

<210> SEQ ID NO 212
<211> LENGTH: 19
<212> TYPE: DNA
<213> ORGANISM: Homo sapiens

<400> SEQUENCE: 212
ggagttcccc gttgtctag                                                    19

<210> SEQ ID NO 213
<211> LENGTH: 19
<212> TYPE: DNA
<213> ORGANISM: Homo sapiens

<400> SEQUENCE: 213
gggtcaccct ccttctcag                                                    19

<210> SEQ ID NO 214
<211> LENGTH: 19
<212> TYPE: DNA
<213> ORGANISM: Homo sapiens

<400> SEQUENCE: 214
gggtcaccct ccttctcat                                                    19

<210> SEQ ID NO 215
<211> LENGTH: 16
<212> TYPE: DNA
<213> ORGANISM: Homo sapiens

<400> SEQUENCE: 215
gtgggctcgc agcaca                                                       16

<210> SEQ ID NO 216
<211> LENGTH: 15
<212> TYPE: DNA
<213> ORGANISM: Homo sapiens

<400> SEQUENCE: 216

```
tgggctcgca gcgca                                              15

<210> SEQ ID NO 217
<211> LENGTH: 19
<212> TYPE: DNA
<213> ORGANISM: Homo sapiens

<400> SEQUENCE: 217
ccgtgcatca ccaccatgt                                          19

<210> SEQ ID NO 218
<211> LENGTH: 18
<212> TYPE: DNA
<213> ORGANISM: Homo sapiens

<400> SEQUENCE: 218
gtgcatcacc accatgcg                                           18

<210> SEQ ID NO 219
<211> LENGTH: 23
<212> TYPE: DNA
<213> ORGANISM: Homo sapiens

<400> SEQUENCE: 219
cacacccagc tgattaaaaa tta                                     23

<210> SEQ ID NO 220
<211> LENGTH: 23
<212> TYPE: DNA
<213> ORGANISM: Homo sapiens

<400> SEQUENCE: 220
cacacccagc tgattaaaaa ttt                                     23

<210> SEQ ID NO 221
<211> LENGTH: 23
<212> TYPE: DNA
<213> ORGANISM: Homo sapiens

<400> SEQUENCE: 221
tcactaagca actccttcaa ctc                                     23

<210> SEQ ID NO 222
<211> LENGTH: 23
<212> TYPE: DNA
<213> ORGANISM: Homo sapiens

<400> SEQUENCE: 222
tcactaagca actccttcaa ctg                                     23

<210> SEQ ID NO 223
<211> LENGTH: 20
<212> TYPE: DNA
<213> ORGANISM: Homo sapiens

<400> SEQUENCE: 223
tttctcctag ggcacagtca                                         20

<210> SEQ ID NO 224
<211> LENGTH: 18
<212> TYPE: DNA
<213> ORGANISM: Homo sapiens

<400> SEQUENCE: 224
```

```
tctcctaggg cacagtcg                                                   18

<210> SEQ ID NO 225
<211> LENGTH: 24
<212> TYPE: DNA
<213> ORGANISM: Homo sapiens

<400> SEQUENCE: 225
ggcttgaaat agtcactgta cttg                                            24

<210> SEQ ID NO 226
<211> LENGTH: 27
<212> TYPE: DNA
<213> ORGANISM: Homo sapiens

<400> SEQUENCE: 226
aatggcttga aatagtcact gtactta                                         27

<210> SEQ ID NO 227
<211> LENGTH: 19
<212> TYPE: DNA
<213> ORGANISM: Homo sapiens

<400> SEQUENCE: 227
gccatagaga caagggcaa                                                  19

<210> SEQ ID NO 228
<211> LENGTH: 19
<212> TYPE: DNA
<213> ORGANISM: Homo sapiens

<400> SEQUENCE: 228
gccatagaga caagggcag                                                  19

<210> SEQ ID NO 229
<211> LENGTH: 25
<212> TYPE: DNA
<213> ORGANISM: Homo sapiens

<400> SEQUENCE: 229
ccagtaacat tgattgagtt gttta                                           25

<210> SEQ ID NO 230
<211> LENGTH: 24
<212> TYPE: DNA
<213> ORGANISM: Homo sapiens

<400> SEQUENCE: 230
cagtaacatt gattgagttg tttg                                            24

<210> SEQ ID NO 231
<211> LENGTH: 19
<212> TYPE: DNA
<213> ORGANISM: Homo sapiens

<400> SEQUENCE: 231
gcaggatccc ttaggcttg                                                  19

<210> SEQ ID NO 232
<211> LENGTH: 17
<212> TYPE: DNA
<213> ORGANISM: Homo sapiens
```

```
<400> SEQUENCE: 232
agccaggagg cctgcta                                                    17

<210> SEQ ID NO 233
<211> LENGTH: 18
<212> TYPE: DNA
<213> ORGANISM: Homo sapiens

<400> SEQUENCE: 233
tatccagctg ggagccaa                                                   18

<210> SEQ ID NO 234
<211> LENGTH: 16
<212> TYPE: DNA
<213> ORGANISM: Homo sapiens

<400> SEQUENCE: 234
ccagccccat ggctct                                                     16

<210> SEQ ID NO 235
<211> LENGTH: 17
<212> TYPE: DNA
<213> ORGANISM: Homo sapiens

<400> SEQUENCE: 235
cacgacgacc ccgagtt                                                    17

<210> SEQ ID NO 236
<211> LENGTH: 14
<212> TYPE: DNA
<213> ORGANISM: Homo sapiens

<400> SEQUENCE: 236
cggtgcgcac cgtt                                                       14

<210> SEQ ID NO 237
<211> LENGTH: 16
<212> TYPE: DNA
<213> ORGANISM: Homo sapiens

<400> SEQUENCE: 237
ttgggttggc cctgaa                                                     16

<210> SEQ ID NO 238
<211> LENGTH: 18
<212> TYPE: DNA
<213> ORGANISM: Homo sapiens

<400> SEQUENCE: 238
tgggctatgc aggagctt                                                   18

<210> SEQ ID NO 239
<211> LENGTH: 17
<212> TYPE: DNA
<213> ORGANISM: Homo sapiens

<400> SEQUENCE: 239
gcacagccca ggatgaa                                                    17

<210> SEQ ID NO 240
<211> LENGTH: 17
<212> TYPE: DNA
<213> ORGANISM: Homo sapiens
```

```
<400> SEQUENCE: 240
catgcagcac caccatg                                                  17

<210> SEQ ID NO 241
<211> LENGTH: 23
<212> TYPE: DNA
<213> ORGANISM: Homo sapiens

<400> SEQUENCE: 241
agcccatttg gtagtgaggc agg                                           23

<210> SEQ ID NO 242
<211> LENGTH: 24
<212> TYPE: DNA
<213> ORGANISM: Homo sapiens

<400> SEQUENCE: 242
gagcccattt ggtagtgagg caga                                          24

<210> SEQ ID NO 243
<211> LENGTH: 23
<212> TYPE: DNA
<213> ORGANISM: Homo sapiens
<220> FEATURE:
<221> NAME/KEY: modified_base
<222> LOCATION: (4)..(4)
<223> OTHER INFORMATION: I

<400> SEQUENCE: 243
aggrtggtat tgaacaacca caa                                           23

<210> SEQ ID NO 244
<211> LENGTH: 22
<212> TYPE: DNA
<213> ORGANISM: Homo sapiens

<400> SEQUENCE: 244
attcaggtaa ttcacaacag gc                                            22

<210> SEQ ID NO 245
<211> LENGTH: 18
<212> TYPE: DNA
<213> ORGANISM: Homo sapiens

<400> SEQUENCE: 245
gactgtggcc gacctgtt                                                 18

<210> SEQ ID NO 246
<211> LENGTH: 18
<212> TYPE: DNA
<213> ORGANISM: Homo sapiens

<400> SEQUENCE: 246
gcacagtgca gagcgctt                                                 18

<210> SEQ ID NO 247
<211> LENGTH: 19
<212> TYPE: DNA
<213> ORGANISM: Homo sapiens

<400> SEQUENCE: 247
ccagatgaaa gcccacatt                                                19
```

<210> SEQ ID NO 248
<211> LENGTH: 22
<212> TYPE: DNA
<213> ORGANISM: Homo sapiens

<400> SEQUENCE: 248
aagcccacat tttgttaaca tg          22

<210> SEQ ID NO 249
<211> LENGTH: 21
<212> TYPE: DNA
<213> ORGANISM: Homo sapiens

<400> SEQUENCE: 249
gcttgttggg atgaatttca a           21

<210> SEQ ID NO 250
<211> LENGTH: 22
<212> TYPE: DNA
<213> ORGANISM: Homo sapiens

<400> SEQUENCE: 250
ctgataagaa cccagaaccc tt          22

<210> SEQ ID NO 251
<211> LENGTH: 14
<212> TYPE: DNA
<213> ORGANISM: Homo sapiens

<400> SEQUENCE: 251
tacactgcca ggca                   14

<210> SEQ ID NO 252
<211> LENGTH: 20
<212> TYPE: DNA
<213> ORGANISM: Homo sapiens

<400> SEQUENCE: 252
tctctgtctg tctcttggca             20

<210> SEQ ID NO 253
<211> LENGTH: 21
<212> TYPE: DNA
<213> ORGANISM: Homo sapiens

<400> SEQUENCE: 253
aagtgctcca tggagtagga g           21

<210> SEQ ID NO 254
<211> LENGTH: 15
<212> TYPE: DNA
<213> ORGANISM: Homo sapiens

<400> SEQUENCE: 254
cgcgagggca agcgc                  15

<210> SEQ ID NO 255
<211> LENGTH: 21
<212> TYPE: DNA
<213> ORGANISM: Homo sapiens

<400> SEQUENCE: 255
cccagaatgc tcaccagcct g           21

```
<210> SEQ ID NO 256
<211> LENGTH: 19
<212> TYPE: DNA
<213> ORGANISM: Homo sapiens

<400> SEQUENCE: 256
gccaggcaat tttatttgc                                              19

<210> SEQ ID NO 257
<211> LENGTH: 12
<212> TYPE: DNA
<213> ORGANISM: Homo sapiens

<400> SEQUENCE: 257
caggcggccg ct                                                     12

<210> SEQ ID NO 258
<211> LENGTH: 21
<212> TYPE: DNA
<213> ORGANISM: Homo sapiens

<400> SEQUENCE: 258
tctctgtctg tctcttggca c                                           21

<210> SEQ ID NO 259
<211> LENGTH: 22
<212> TYPE: DNA
<213> ORGANISM: Homo sapiens

<400> SEQUENCE: 259
tctctgtctg tctcttggca ca                                          22

<210> SEQ ID NO 260
<211> LENGTH: 23
<212> TYPE: DNA
<213> ORGANISM: Homo sapiens

<400> SEQUENCE: 260
tctctgtctg tctcttggca cag                                         23

<210> SEQ ID NO 261
<211> LENGTH: 21
<212> TYPE: DNA
<213> ORGANISM: Homo sapiens

<400> SEQUENCE: 261
atacacacat gtgcacacac a                                           21

<210> SEQ ID NO 262
<211> LENGTH: 21
<212> TYPE: DNA
<213> ORGANISM: Homo sapiens
<220> FEATURE:
<221> NAME/KEY: modified_base
<222> LOCATION: (12)..(12)
<223> OTHER INFORMATION: 2-thio-deoxythymidine
<220> FEATURE:
<221> NAME/KEY: modified_base
<222> LOCATION: (19)..(19)
<223> OTHER INFORMATION: 2-amino-adenosine

<400> SEQUENCE: 262
atacacacat gtgcacacac a                                           21
```

<210> SEQ ID NO 263
<211> LENGTH: 21
<212> TYPE: DNA
<213> ORGANISM: Homo sapiens
<220> FEATURE:
<221> NAME/KEY: modified_base
<222> LOCATION: (9)..(9)
<223> OTHER INFORMATION: 4-methylindole

<400> SEQUENCE: 263
atacacacat gtgcacacac a                    21

<210> SEQ ID NO 264
<211> LENGTH: 19
<212> TYPE: DNA
<213> ORGANISM: Homo sapiens
<220> FEATURE:
<221> NAME/KEY: modified_base
<222> LOCATION: (8)..(8)
<223> OTHER INFORMATION: 2-aminio-adenosine
<220> FEATURE:
<221> NAME/KEY: modified_base
<222> LOCATION: (17)..(17)
<223> OTHER INFORMATION: 2 -thio-deoxythymidine

<400> SEQUENCE: 264
gccaggcaat tttatttgc                       19

<210> SEQ ID NO 265
<211> LENGTH: 19
<212> TYPE: DNA
<213> ORGANISM: Homo sapiens
<220> FEATURE:
<221> NAME/KEY: modified_base
<222> LOCATION: (8)..(9)
<223> OTHER INFORMATION: 2-amino-adenosine
<220> FEATURE:
<221> NAME/KEY: modified_base
<222> LOCATION: (16)..(17)
<223> OTHER INFORMATION: 2-thio-deoxythymidine

<400> SEQUENCE: 265
gccaggcaat tttatttgc                       19

<210> SEQ ID NO 266
<211> LENGTH: 25
<212> TYPE: DNA
<213> ORGANISM: Homo sapiens

<400> SEQUENCE: 266
tgccttgaat tatttacgtt catta                25

<210> SEQ ID NO 267
<211> LENGTH: 25
<212> TYPE: DNA
<213> ORGANISM: Homo sapiens

<400> SEQUENCE: 267
tgccttgaat tatttacgtt catta                25

<210> SEQ ID NO 268
<211> LENGTH: 18
<212> TYPE: DNA
<213> ORGANISM: Homo sapiens

<400> SEQUENCE: 268
cacacatgtg cacacacg                        18

<210> SEQ ID NO 269
<211> LENGTH: 18
<212> TYPE: DNA
<213> ORGANISM: Homo sapiens
<220> FEATURE:
<221> NAME/KEY: modified_base
<222> LOCATION: (16)..(16)
<223> OTHER INFORMATION: 4-methylindole

<400> SEQUENCE: 269
cacacatgtg cacacacg                                                 18

<210> SEQ ID NO 270
<211> LENGTH: 19
<212> TYPE: DNA
<213> ORGANISM: Homo sapiens

<400> SEQUENCE: 270
tttgctgatg ggtgaccta                                                19

<210> SEQ ID NO 271
<211> LENGTH: 19
<212> TYPE: DNA
<213> ORGANISM: Homo sapiens
<220> FEATURE:
<221> NAME/KEY: modified_base
<222> LOCATION: (8)..(8)
<223> OTHER INFORMATION: 4-methylindole

<400> SEQUENCE: 271
tttgctgatg ggtgaccta                                                19

<210> SEQ ID NO 272
<211> LENGTH: 19
<212> TYPE: DNA
<213> ORGANISM: Homo sapiens
<220> FEATURE:
<221> NAME/KEY: modified_base
<222> LOCATION: (8)..(8)
<223> OTHER INFORMATION: 5-nitroindole

<400> SEQUENCE: 272
tttgctgatg ggtgaccta                                                19

<210> SEQ ID NO 273
<211> LENGTH: 19
<212> TYPE: DNA
<213> ORGANISM: Homo sapiens
<220> FEATURE:
<221> NAME/KEY: modified_base
<222> LOCATION: (8)..(8)
<223> OTHER INFORMATION: abasic nucleotide

<400> SEQUENCE: 273
tttgctgatg ggtgaccta                                                19

<210> SEQ ID NO 274
<211> LENGTH: 14
<212> TYPE: DNA
<213> ORGANISM: Homo sapiens

<400> SEQUENCE: 274
tacactgcca ggca                                                     14

<210> SEQ ID NO 275

-continued

```
<211> LENGTH: 50
<212> TYPE: DNA
<213> ORGANISM: Artificial sequence
<220> FEATURE:
<223> OTHER INFORMATION: primer sequence
<220> FEATURE:
<221> NAME/KEY: misc_feature
<222> LOCATION: (39)..(45)
<223> OTHER INFORMATION: "n" at positions 39-45 can be any base

<400> SEQUENCE: 275
ggccagtaat tgtaatacga ctcactatag ggaggcggnn nnnnncgaga            50

<210> SEQ ID NO 276
<211> LENGTH: 27
<212> TYPE: DNA
<213> ORGANISM: Homo sapiens

<400> SEQUENCE: 276
gttcttaatt cataggttgc aattta                                     27

<210> SEQ ID NO 277
<211> LENGTH: 22
<212> TYPE: DNA
<213> ORGANISM: Homo sapiens

<400> SEQUENCE: 277
gcttcgagta cgacgaccct cg                                         22
```